United States Patent
Brown et al.

(10) Patent No.: US 9,102,621 B2
(45) Date of Patent: Aug. 11, 2015

(54) ACYL SULFONAMIDE COMPOUNDS

(75) Inventors: Alan Daniel Brown, Sandwich (GB); David James Rawson, Sandwich (GB); Robert Ian Storer, Sandwich (GB); Nigel Alan Swain, Sandwich (GB)

(73) Assignee: Pfizer Limited, Sandwich (GB)

( * ) Notice: Subject to any disclaimer, the term of this patent is extended or adjusted under 35 U.S.C. 154(b) by 79 days.

(21) Appl. No.: 13/808,653

(22) PCT Filed: Jul. 4, 2011

(86) PCT No.: PCT/IB2011/052942
§ 371 (c)(1),
(2), (4) Date: Jan. 7, 2013

(87) PCT Pub. No.: WO2012/007869
PCT Pub. Date: Jan. 19, 2012

(65) Prior Publication Data
US 2013/0109708 A1     May 2, 2013

Related U.S. Application Data

(60) Provisional application No. 61/484,846, filed on May 11, 2011, provisional application No. 61/363,409, filed on Jul. 12, 2010.

(51) Int. Cl.
| | |
|---|---|
| C07D 213/24 | (2006.01) |
| C07D 311/04 | (2006.01) |
| A61K 31/44 | (2006.01) |
| A61K 31/18 | (2006.01) |
| C07D 213/69 | (2006.01) |
| C07D 213/30 | (2006.01) |
| C07D 213/64 | (2006.01) |
| C07D 213/65 | (2006.01) |
| C07D 217/24 | (2006.01) |
| C07D 471/04 | (2006.01) |
| A61K 31/437 | (2006.01) |
| A61K 31/472 | (2006.01) |
| A61K 31/505 | (2006.01) |
| A61K 45/06 | (2006.01) |
| C07D 217/02 | (2006.01) |
| C07D 239/34 | (2006.01) |

(52) U.S. Cl.
CPC ............ *C07D 213/69* (2013.01); *A61K 31/437* (2013.01); *A61K 31/44* (2013.01); *A61K 31/472* (2013.01); *A61K 31/505* (2013.01); *A61K 45/06* (2013.01); *C07D 213/30* (2013.01); *C07D 213/64* (2013.01); *C07D 213/65* (2013.01); *C07D 217/02* (2013.01); *C07D 217/24* (2013.01); *C07D 239/34* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,744,818 | A | 5/1988 | Heiba et al. |
| 5,543,279 | A | 8/1996 | Matsuda et al. |
| 5,565,429 | A | 10/1996 | Vincent et al. |
| 5,851,745 | A | 12/1998 | Takeuchi |
| 6,251,827 | B1 | 6/2001 | Ziemer et al. |
| 6,348,474 | B1 | 2/2002 | Kayakiri et al. |
| 6,376,512 | B1 | 4/2002 | Jayyosi et al. |
| 6,555,584 | B1 | 4/2003 | Ikawa et al. |
| 7,772,285 | B2 | 8/2010 | Chaki et al. |
| 8,314,240 | B2 | 11/2012 | Kubota et al. |
| 2002/0086887 | A1 | 7/2002 | Augeri et al. |
| 2008/0027096 | A1* | 1/2008 | Garg et al. .................... 514/311 |
| 2008/0188467 | A1 | 8/2008 | Wong et al. |
| 2009/0143358 | A1 | 6/2009 | Marron et al. |
| 2010/0179137 | A1 | 7/2010 | Kamikubo et al. |
| 2010/0210660 | A1 | 8/2010 | Kremoser et al. |
| 2012/0010182 | A1 | 1/2012 | Brown et al. |
| 2012/0010183 | A1 | 1/2012 | Bell et al. |
| 2012/0010207 | A1 | 1/2012 | Bell et al. |
| 2013/0109667 | A1 | 5/2013 | Markworth et al. |
| 2013/0109696 | A1 | 5/2013 | Greener et al. |
| 2013/0109701 | A1 | 5/2013 | Brown et al. |
| 2013/0116285 | A1 | 5/2013 | Bell et al. |

FOREIGN PATENT DOCUMENTS

| | | |
|---|---|---|
| EP | 0003416 | 8/1979 |
| EP | 0023100 | 1/1981 |
| EP | 0029742 | 6/1981 |
| EP | 0194599 | 9/1986 |
| EP | 0281103 | 9/1988 |
| EP | 0325245 | 7/1989 |
| EP | 0399732 | 11/1990 |

(Continued)

OTHER PUBLICATIONS

"Molecular Mechanisms of Cancer Pain" by Mantyh et al., Nature Rev. 2, 201-09 (2002).*

(Continued)

*Primary Examiner* — Theodore R West
(74) *Attorney, Agent, or Firm* — J. Michael Dixon

(57) ABSTRACT

The invention relates to sulfonamide derivatives, to their use in medicine, to 5 compositions containing them, to processes for their preparation and to intermediates used in such processes. More particularly the invention relates to a new sulfonamide Nav1.7 inhibitors of formula (I): 10 X NH O S O O R1 R2 R5 R4 R3 Het1 (I) or a pharmaceutically acceptable salt thereof, wherein X, Het1, R1, R2, R3, R4 and R5 are as defined in the description. 15 Nav 1.7 inhibitors are potentially useful in the treatment of a wide range of disorders, particularly pain.

18 Claims, No Drawings

(56) References Cited

FOREIGN PATENT DOCUMENTS

| | | |
|---|---|---|
| EP | 0412848 | 2/1991 |
| EP | 0453210 | 10/1991 |
| EP | 0570006 | 11/1993 |
| EP | 0684521 | 11/1995 |
| EP | 0753508 | 1/1997 |
| GB | 2266527 | 11/1993 |
| WO | 8801133 | 2/1988 |
| WO | 8904303 | 5/1989 |
| WO | 8904304 | 5/1989 |
| WO | 8904305 | 5/1989 |
| WO | 8912628 | 12/1989 |
| WO | 9104964 | 4/1991 |
| WO | 9300332 | 1/1993 |
| WO | 9413636 | 6/1994 |
| WO | 9421590 | 9/1994 |
| WO | 9604905 | 2/1996 |
| WO | 9609818 | 4/1996 |
| WO | 9920275 | 4/1999 |
| WO | 9947508 | 9/1999 |
| WO | 0039077 | 7/2000 |
| WO | 0064876 | 11/2000 |
| WO | 0066120 | 11/2000 |
| WO | 0136365 | 5/2001 |
| WO | 0166098 | 9/2001 |
| WO | 0224636 | 3/2002 |
| WO | 2004018386 | 3/2004 |
| WO | 2005013914 | 2/2005 |
| WO | 2005080346 | 9/2005 |
| WO | 2005094810 | 10/2005 |
| WO | 2006015158 | 2/2006 |
| WO | 2006045514 | 5/2006 |
| WO | 2006121097 | 11/2006 |
| WO | 2007072782 | 6/2007 |
| WO | 2008025539 | 3/2008 |
| WO | 2008092231 | 8/2008 |
| WO | 2008118758 | 10/2008 |
| WO | 2009012242 | 1/2009 |
| WO | 2009049181 | 4/2009 |
| WO | 2009064250 | 5/2009 |
| WO | 2009064251 | 5/2009 |
| WO | 2009067541 | 5/2009 |
| WO | 2009067621 | 5/2009 |
| WO | 2009080835 | 7/2009 |
| WO | 2010079443 | 7/2010 |

OTHER PUBLICATIONS

Naganawa et al., "Further optimization of sulfonamide analogs as EP1 receptor antagonists: Synthesis and evaluation of bioisosteres for the carboxylic acid group", Bioorganic & Medicinal Chemistry, vol. 14(21), pp. 7121-7137 (2006).

Pinkerton et al., "Allosteric potentiators of the metabotropic glutamate receptor 2 (mGlu2). Part 3: Identification and biological activity of indanone containing mGlu2 receptor potentiators", Bioorganic & Medicinal Chemistry Letters, vol. 15(6), pp. 1565-1571 (2005).

Ng et al., "Design, Synthesis, and Biological Activity of Novel Factor Xa Inhibitors: 4-Aryloxy Substituents of 2,6-Diphenoxypyridines", Bioorganic & Medicinal Chemistry, vol. 10(3), pp. 657-666 (2002).

Zakarya et al., "Substituent effects on the toxicity for a series of herbicides", Romanian Chemical Quarterly Reviews, vol. 7(2), pp. 127-137 (1999).

Hamill et al., "Development of [11C]L-159,884: A Radiolabelled, Nonpeptide Angiotensin II Antagonist that is Useful for Angiotensin II, AT1 Receptor Imaging", Applied Radiation and Isotopes, vol. 47(2), pp. 211-218 (1996).

Matassa et al., "Synthesis and in Vitro LTD4 Antagonist Activity of Bicyclic and Monocyclic Cyclopentylurethane and Cyclopentylacetamide N-Arylsulfonyl Amides", Journal of Medicinal Chemistry, vol. 33(9), pp. 2621-2629 (1990).

Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", Journal of Medicinal Chemistry, vol. 33(1), pp. 240-245 (1990).

Brown et al., "Hydroxyacetophenone-Derived Antagonists of the Peptidoleukotriens", Journal of Medicinal Chemistry, vol. 32(4), pp. 807-826 (1989).

Dubois et al., "Dihydrochalcone Sweeteners. A Study of the Atypical Temporal Phenomena", Journal of Medicinal Chemistry, vol. 24(4), pp. 408-428 (1981).

Silverman, Richard B. The Organic Chemistry of Drug Design and Drug Action. 2nd Ed., 2004, pp. 29-32, Elsevier, Burlington, MA.

\* cited by examiner

ACYL SULFONAMIDE COMPOUNDS

CROSS REFERENCE

This application is the National Stage Application of International Patent Application No. PCT/IB2011/052942, filed Jul. 4, 2011, which claims priority to U.S. Provisional Patent Application No. 61/484,836, filed on May 11, 2011 and U.S. Provisional Patent Application No. 61/363,409, filed on Jul. 12, 2010.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha subunits. Names for this family include SCNx, SCNAx, and $Na_v x.x$. The VGSC family has been phylogenetically divided into two subfamilies $Na_v 1.x$ (all but SCN6A) and $Na_v 2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The $Na_v 1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_v 1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v 1.7$ protein has been shown to accumulate in neuromas, particularly painful neuromas (Kretschmer et al., *Acta. Neurochir.* (Wien), 144(8): 803-10 (2002)). Gain of function mutations of $Na_v 1.7$, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7; 69(6): 505-7 (2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.*; 52(5):767-74 (2006). Further evidence of the role of Nav1.7 in pain is found in the phenotype of loss of function mutations of the SCN9A gene. Cox and colleagues (*Nature*, 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.*; 71(4): 311-9 (2007), Ahmad et al, *Hum Mol. Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including postsurgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new $Na_v 1.7$ inhibitors that are good drug candidates.

Preferably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound of formula (I)

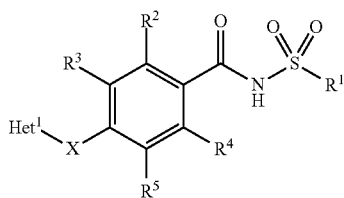

or a pharmaceutically acceptable salt thereof, wherein
X is —OCH$_2$— or —CH$_2$O—;
Het$^1$ is (i) a 9- or 10-membered heteroaryl comprising one to three nitrogen atoms; or (ii) a 6-, 9- or 10-membered heteroaryl comprising one to three nitrogen atoms which heteroaryl is independently substituted by one to three substituents selected from Y$^1$ and Y$^2$;
Y$^1$ and Y$^2$ are independently selected from F; Cl; CN; (C$_1$-C$_8$)alkyl, optionally substituted by (C$_3$-C$_8$)cycloalkyl or one to three F; (C$_3$-C$_8$)cycloalkyl, optionally substituted by one to three F; NR$^7$R$^8$; (C$_1$-C$_8$)alkyloxy, optionally independently substituted by one to three R$^9$; (C$_3$-C$_8$)cycloalkyloxy; phenyl, optionally independently substituted by one to three R$^{10}$; Het$^2$ and Het$^3$; wherein (C$_3$-C$_8$)cycloalkyloxy may be optionally fused to a phenyl ring or may be independently substituted by one to three R$^{10}$;
R$^1$ is (C$_1$-C$_6$)alkyl or (C$_3$-C$_8$)cycloalkyl, each of which is optionally substituted by one to three F;
R$^2$, R$^3$, R$^4$ are independently H, F, Cl or —OCH$_3$;
R$^5$ is H, CN, F, Cl or R$^6$;
R$^6$ is a group selected from (C$_1$-C$_6$)alkyl and (C$_1$-C$_6$)alkyloxy, wherein each group is optionally substituted, valency permitting, by one to five F;
R$^7$ and R$^8$ are independently H; (C$_1$-C$_8$)alkyl, optionally independently substituted by one to three R$^{11}$; (C$_3$-C$_8$)cycloalkyl; or 'C-linked' Het$^2$; wherein (C$_3$-C$_8$)cycloalkyl may be optionally fused to a phenyl ring or may be independently substituted by one to three R$^{10}$; or
R$^7$ and R$^8$, taken together with the nitrogen atom to which they are attached, form a saturated, bridged, 7- to 9-membered ring;
R$^9$ is F; (C$_1$-C$_6$)alkyloxy; (C$_3$-C$_8$)cycloalkyl, optionally substituted by one to three F; Het$^2$; or phenyl, optionally independently substituted by one to three R$^6$;
R$^{10}$ is F, Cl or R$^6$;
R$^{11}$ is F; (C$_1$-C$_6$)alkyloxy; (C$_3$-C$_8$)cycloalkyl, optionally substituted by one to three F; 'C-linked' Het$^2$; or phenyl, optionally independently substituted by one to three R$^6$;
Het$^2$ is a 3- to 8-membered saturated monoheterocycloalkyl comprising one or two ring members selected from —NR$^{12}$— and —O—, said monoheterocycloalkyl being optionally substituted on a ring carbon atom by one to three substituents independently selected from F, (C$_1$-C$_6$)alkyl, (C$_1$-C$_4$)alkyloxy(C$_0$-C$_4$)alkylene and (C$_3$-C$_8$)cycloalkyl;
Het$^3$ is a 5- or 6-membered heteroaryl comprising one to three nitrogen atoms, said heteroaryl being optionally substituted by one to three substituents selected from F, Cl, CN and R$^6$; and
R$^{12}$ is H, (C$_1$-C$_6$)alkyl or (C$_3$-C$_8$)cycloalkyl, wherein (C$_1$-C$_6$)alkyl and (C$_3$-C$_8$)cycloalkyl are optionally substituted by one to three F; or, when Het$^2$ is 'N-linked', is absent.

Described below are a number of embodiments (E) of this first aspect of the invention, where for convenience E1 is identical thereto.

E1 A compound of formula (I) as defined above or a pharmaceutically acceptable salt thereof.
E2 A compound according to E1 wherein X is —OCH$_2$—.
E3 A compound according to either E1 wherein X is —CH$_2$O—.
E4 A compound according to any of E1 to E3 wherein Het$^1$ is a 6-membered heteroaryl comprising one or two nitrogen atoms which heteroaryl is independently substituted by one to three substituents selected from Y$^1$ and Y$^2$.
E5 A compound according to any of E1 or E4 wherein Het$^1$ is a 6-membered heteroaryl comprising one or two nitrogen atoms which heteroaryl is independently substituted by one or two substituents selected from Y$^1$ and Y$^2$.
E6 A compound according to any of E1 to E5 wherein Het$^1$ is pyridyl independently substituted by one or two substituents selected from Y$^1$ and Y$^2$.
E7 A compound according to any of E1 to E6 wherein Het$^1$ is pyridyl independently substituted by one or two substituents selected from Y$^1$ and Y$^2$ and wherein said pyridyl is orientated as below:

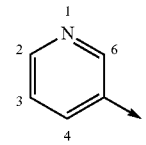

E8 A compound according to E7 wherein said pyridyl is 2-substituted by Y$^1$, 3-substituted by Y$^2$ or, where di-substituted, 2-substituted by Y$^1$ and 3-substituted by Y$^2$.
E9 A compound according to any of E1 to E8 wherein Y$^1$ is (C$_1$-C$_8$)alkyl, optionally substituted by (C$_3$-C$_8$)cycloalkyl or one to three F; (C$_3$-C$_8$)cycloalkyl, optionally substituted by one to three F; (C$_1$-C$_6$)alkyloxy, optionally substituted by one to three F; (C$_3$-C$_8$)cycloalkyloxy; or Het$^2$.
E10 A compound according to any of E1 to E9 wherein Y$^1$ is (C$_1$-C$_6$)alkyl, optionally substituted by (C$_3$-C$_6$)cycloalkyl or one to three F; (C$_3$-C$_6$)cycloalkyl, optionally substituted by one to three F; (C$_1$-C$_6$)alkyloxy, optionally substituted by one to three F; (C$_3$-C$_8$)cycloalkyloxy; 4- to 6-membered or Het$^2$.
E11 A compound according to any of E1 to E10 wherein Y$^2$ is F, Cl, CN, (C$_1$-C$_8$)alkyl, optionally substituted by (C$_3$-C$_8$)cycloalkyl or one to three F; (C$_3$-C$_8$)cycloalkyl, optionally substituted by one to three F; (C$_1$-C$_6$)alkyloxy, optionally substituted by one to three F; (C$_3$-C$_8$)cycloalkyloxy; or Het$^2$.
E12. A compound according to any of E1 to E11 wherein Y$^2$ is F, Cl, CN, (C$_1$-C$_4$)alkyl, optionally substituted by (C$_3$-C$_6$)cycloalkyl or one to three F; (C$_3$-C$_6$)cycloalkyl, optionally substituted by one to three F; (C$_1$-C$_6$)alkyloxy, optionally substituted by one to three F; (C$_3$-C$_6$)cycloalkyloxy; or 4- to 6-membered Het$^2$.
E13 A compound according to any of E1 to E12 wherein R$^1$ is (C$_1$-C$_4$)alkyl or (C$_3$-C$_6$)cycloalkyl.
E14 A compound according to any of E1 to E13 wherein R$^1$ is (C$_1$-C$_3$)alkyl or (C$_3$-C$_4$)cycloalkyl.
E15 A compound according to any of E1 to E14 wherein R$^1$ is methyl or cyclopropyl, such as methyl.
E16 A compound according to any of E1 to E15 wherein R$^2$, R$^3$ and R$^4$ are independently H or F.
E17 A compound according to any of E1 to E16 wherein R$^2$ is F; and R$^3$ and R$^4$ are independently H or F.

E18 A compound according to any of E1 to E17 wherein $R^5$ is H; CN; F; Cl; $(C_1-C_4)$alkyl, optionally substituted by one to three F; or $(C_1-C_4)$alkyloxy, optionally substituted by one to three F.

E19 A compound according to any of E1 to E18 wherein $R^5$ is H, CN, F, Cl, $CH_3$, $C_2H_5$, $CF_3$, —$OCH_3$, —$OC_2H_5$ or —$OCF_3$.

E20 A compound according to any of E1 to E19 wherein $R^5$ is F or Cl.

Alkyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

Examples of cycloalkyl include cyclopropyl, cyclobutyl, cyclopentyl, cyclohexyl, cycloheptyl and cyclooctyl.

Halo means fluoro, chloro, bromo or iodo.

The term 'C-linked' used in the definitions of formula (I) means that the group in question is joined via a ring carbon. The term 'N-linked' used in the definitions of formula (I) means that the group in question is joined via a ring nitrogen.

Specific examples of 5- or 6-membered heteroaryl used in the definitions of formula (I) include pyrrolyl, pyrazolyl, imidazoyl, thiazolyl, isothiazolyl, thiadiazolyl, pyridyl, pyridazinyl, pyrimidinyl and pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of 9- or 10-membered heteroaryl used in the definitions of formula (I) include indolyl, benzimidazolyl, indazolyl, benzotriazolyl, pyrrolo[2,3-b]pyridyl, pyrrolo[2,3-c]pyridyl, pyrrolo[3,2-c]pyridyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridyl, pyrazolo[3,4-b]pyridyl, isoindolyl, indazolyl, purinyl, indolizinyl, imidazo[1,2-a]pyridyl, imidazo[1,5-a]pyridyl, pyrazolo[1,5-a]pyridyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-d]pyrazinyl and pyrido[3,4-b]pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of $Het^2$ include oxiranyl, aziridinyl, oxetanyl, azetidinyl, tetrahydrofuranyl, pyrrolidinyl, tetrahydropyranyl, piperidinyl, morpholinyl, piperazinyl, azepanyl, oxepanyl, oxazepanyl and diazepinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (—Ph>—PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the following general methods, $R^1$, $R^2$, $R^3$, $R^4$, $R^5$ and $Het^1$ are as previously defined for a derivative of the formula (I) unless otherwise stated. Pg is a suitable carboxylic acid protecting group, such as tert butyl, methyl, ethyl, or tolyl. Lg is a suitable leaving group, such as halo (e.g. Br) or a sulphonate ester (e.g. mesylate, triflate or tosylate).

Where ratios of solvents are given, the ratios are by volume.

According to a first process, compounds of formula (I) wherein X is —CH$_2$O— may be prepared by the process illustrated in Scheme 1.

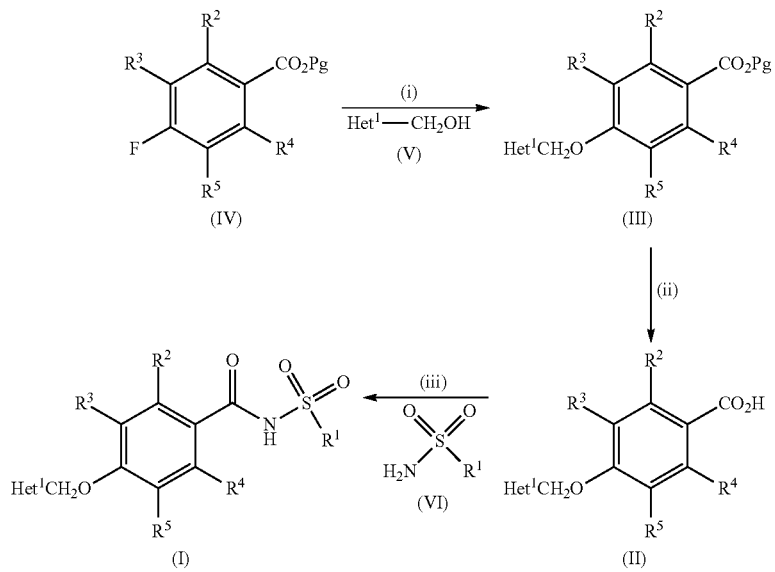

Scheme 1

Compounds of formula (I) can be prepared from compounds of formula (II) according to reaction step (iii) by activation of the acid group with reagents such as oxalyl chloride, propanephosphonic acid cyclic anhydride, carbonyl di-imidazole (CM), a uronium based peptide coupling agent or a carbodiimide reagent, followed by displacement with a sulphonamide of formula (VI) in the presence of a nucleophilic base, such as 4-dimethylaminopyridine. Typical conditions comprise N,N-dimethylaminopropyl-N'-ethylcarbodiimide and 4-dimethylaminopyridine in dichloromethane.

Compounds of formula (II) can be prepared by hydrolysis of the ester functional group in compounds of formula (III) by either acidic or basic methods according to step (ii). Preferred conditions are lithium hydroxide in THF/water at 60° C.

Compounds of formula (III) can be made from compounds of formula (IV) by a nucleophilic aromatic substitution reaction (SNAr) using an alcohol of formula (V) and base, according to step (i). Suitable conditions include, potassium carbonate in DMF or DMSO, sodium hydride in NMP or DMF, sodium hydroxide or potassium hydroxide in 1,4-dioxane and water or DMSO or potassium tert-butoxide in THF, between room temperature and 150° C. Preferred conditions comprise 1 equivalent of potassium tert-butoxide in THF/DMSO at 80° C. for 16 hours.

According to a second process, compounds of formula (I) wherein X is —CH$_2$O— may be prepared by the process illustrated in Scheme 2.

conditions comprise N,N-dimethylaminopropyl-N'-ethylcarbodiimide and 4-dimethylaminopyridine in dichloromethane.

Compounds of formula (II) can be prepared by hydrolysis of the ester functional group in compounds of formula (III) under conditions described in Scheme 1 step (ii). Preferred conditions are lithium hydroxide in tetrahydrofuran/water at 60° C.).

Compounds of formula (III) can be made from compounds of formula (VIII) according to step (i) by a nucleophilic displacement (SN2) reaction with compounds of formula (VII) in the presence of a base. Suitable conditions include potassium carbonate in DMF or DMSO, sodium hydride in NMP or DMF, sodium hydroxide or potassium hydroxide in 1,4-dioxane and water or DMSO or potassium tert-butoxide in tetrahydrofuran at from room temperature to 150° C. Preferred conditions comprise sodium hydride in tetrahydrofuran at room temperature for 48 hours.

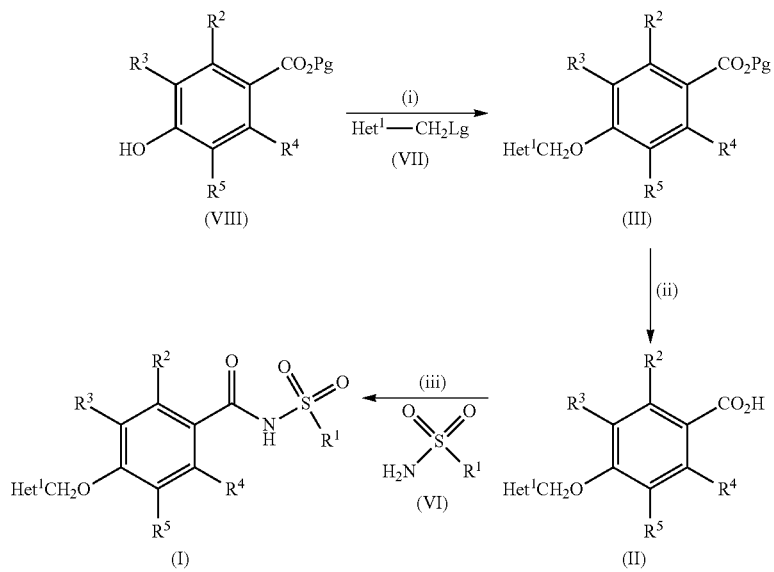

Scheme 2

Compounds of formula (I) can be prepared from compounds of formulae (II) and (VI) according to reaction step (iii) under conditions described in Scheme 1 step (iii). Typical According to a third process, compounds of formula (I) wherein X is —OCH$_2$— may be prepared by the process illustrated in Scheme 1.

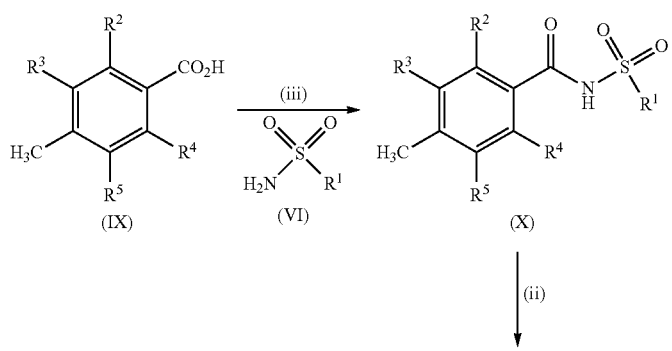

Scheme 3

-continued

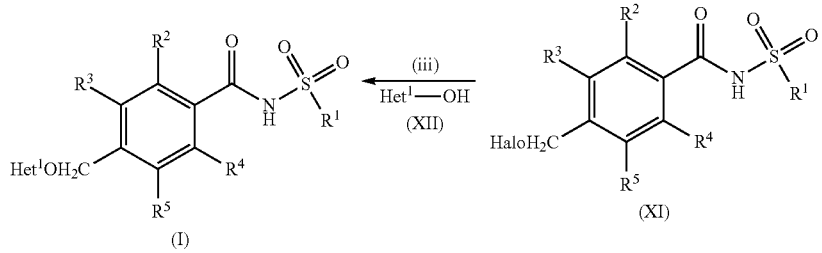

Compounds of formula (I) can be prepared from compounds of formula (XI) according to step (iii) by nucleophilic displacement of the halogen group by an alcohol of formula (XII). Conveniently the reaction is carried out in the presence of an auxiliary base such as triethylamine, diisopropylethylamine, potassium or sodium carbonate, sodium or potassium hydroxide in a variety of solvents such as NMP, 1,4-dioxane, DMSO or DMF from room temperature to 150° C. Preferred conditions are potassium carbonate in DMSO at room temperature.

nephosphonic acid cyclic anhydride, carbonyl di-imidazole (CM), a uronium based peptide coupling agent or a carbodiimide reagent, followed by displacement with a sulphonamide of formula (VI) in the presence of a nucleophilic base, such as 4-dimethylaminopyridine. Preferred conditions comprise propanephosphonic acid cyclic anhydride and diisopropylethylamine in tetrahydrofuran with methanesulphonamide.

According to a fourth process, compounds of formula (I) wherein X is —OCH$_2$— may be prepared by the process illustrated in Scheme 4.

Scheme 4

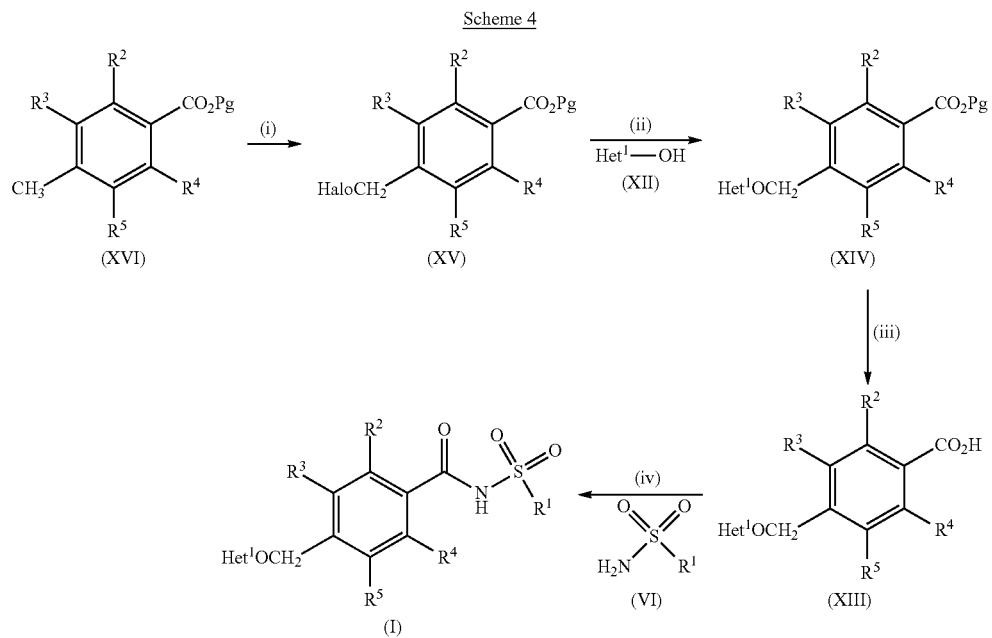

Compounds of formula (XI) can be prepared by halogenation of the methyl group in compounds of formula (X) according to step (ii) using a halogenating reagent. Conveniently halogenation is effected using a reagent such as N-bromosuccinimide, N-iodosuccinimide, bromine, iodine, sodium bromate in a variety of solvents such as carbon tetrachloride, 1,2-dichloroethane, chloroform, dichloromethane, ethyl acetate, acetic acid and water often in the presence of an initiator such as dibenzoyl peroxide or azobisisobutyronitrile. Preferred conditions are N-bromosuccinimide in the presence of azobisisobutyronitrile in 1,2-dichloroethane at reflux.

Compounds of formula (X) can be made from compounds of formula (IX) according to reaction step (i) by activation of the acid group with reagents such as oxalyl chloride, propa- Compounds of formula (I) can be prepared from compounds of formulae (VII) and (XIII) according to reaction step (iv) under conditions described in Scheme 1 step (i). Preferred conditions comprise O-(7-azabenzotriazol-1-yl)-N,N,N'N'-tetramethyluroniumhexafluorophosphate, and N,N-diisopropylethylamine in dichloromethane.

Compounds of formula (XIII) can be prepared by hydrolysis of the ester functional group in compounds of formula (XIV) according to step (iii) under acidic or basic conditions. Acidic conditions include trifluoroacetic acid or HCl gas in a solvent such as 1,4-dioxane or dichloromethane. Basic conditions include lithium, sodium or potassium hydroxides in solvents such as tetrahydrofuran, methanol or 1,4-dioxane. Preferred conditions are lithium hydroxide in tetrahydrofuran/water at room temperature.

Compounds of formula (XIII) can be prepared from compounds of formula (XV) according to step (ii) by displacement of the halogen group by an alcohol of formula (XII). Conveniently the reaction is carried out in the presence of an auxiliary base such as triethylamine, diisopropylethylamine, potassium or sodium carbonate, sodium or potassium hydroxide in a variety of solvents such as NMP, 1,4-dioxane, DMSO or DMF from room temperature to 150° C. Preferred conditions are potassium carbonate in DMSO at room temperature.

Compounds of formula (XV) (wherein halo is Br or I) can be prepared by halogenation of the methyl group in compounds of formula (XVI) according to step (i) using a halogenating reagent. Conveniently halogenation is effected using a reagent such as N-bromosuccinimide, N-iodosuccinimide, bromine, iodine, sodium bromate in a variety of solvents such as carbon tetrachloride, 1,2-dichloroethane, chloroform, dichloromethane, ethyl acetate, acetic acid and water often in the presence of an initiator such as dibenzoyl peroxide or azobisisobutyronitrile. Preferred conditions are N-bromosuccinimide and dibenzoyl peroxide in carbon tetrachloride at reflux.

Compounds of formulae (IV), (V), (VI), (VII), (VIII), (IX), (XII) and (XVI) are either commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™ Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of formula (I), or a pharmaceutically acceptable salt thereof, as defined above, may be administered in combination with one or more agents selected from:
an alternative Nav1.7 channel modulator, such as another compound of the present invention or a compound disclosed in WO 2009/012242;
an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;
a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene) piperidene-1-carboxamide);
an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5\text{-HT}_{1B/1D}$ agonist such as eletriptan, sumatriptan, naratriptan, zolmitriptan or rizatriptan;

a $5\text{-HT}_{2A}$ receptor antagonist such as R(+)-alpha-(2,3-dimethoxy-phenyl)-1-[2-(4-fluorophenylethyl)]-4-piperidinemethanol (MDL-100907);

a $5\text{-HT}_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-yrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870; and a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3, 5-trimethyl-6-(3-pyridylmethyl), 1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl) acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid,
$Cs_2CO_3$ is caesium carbonate;
$Cu(acac)_2$ is copper (II) acetylacetonate;
CuI is copper (I) iodide;
$Cu(OAc)_2$ is copper (II) acetate;
DAD is diode array detector;
DCM is dichloromethane; methylene chloride;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDCl is 1-(3-dimethylaminopropyl)-3-ethylcarbodiimide hydrochloride;
EDTA is ethylenediaminetetraacetic acid;
ELSD is evaporative light scattering detection;
$Et_2O$ is diethyl ether;
EtOAc is ethyl acetate;
EtOH is ethanol;
HCl is hydrochloric acid;
IPA is isopropanol;
$Ir_2(OMe)_2COD_2$ is bis(1,5-cyclooctadiene)di-μ-methoxydiiridium (I);
$K_2CO_3$ is potassium carbonate;
$KHSO_4$ is potassium hydrogen sulphate;
KOAc is potassium acetate;
KOH is potassium hydroxide;
$K_3PO_4$ is potassium phosphate tribasic;

LCMS is liquid chromatography mass spectrometry ($R_t$=retention time)
LiOH is lithium hydroxide;
MeOH is methanol;
$MgSO_4$ is magnesium sulphate;
NaH is sodium hydride;
$NaHCO_3$ is sodium hydrogencarbonate;
$Na_2CO_3$ is sodium carbonate;
$NaHSO_3$ is sodium bisulphate;
$NaHSO_4$ is sodium hydrogensulphate;
NaOH is sodium hydroxide;
$Na_2SO_4$ is sodium sulphate;
$NH_4Cl$ is ammonium chloride;
NMP is N-Methyl-2-pyrrolidone;
Pd/C is palladium on carbon;
$Pd(PPh_3)_4$ is palladium tetrakis;
$Pd(dppf)_2Cl_2$ is [1,1'-bis(diphenylphosphino)ferrocene]dichloropalladium(II), complex with dichloromethane;
TBME is tert-butyl methyl ether;
TFA is trifluoroacetic acid
THF is tetrahydrofuran;
THP is tetrahydropyran;
TLC is thin layer chromatography; and
WSCDI is 1-(3-dimethylaminopropyl)-3-ethylcarbodiimide hydrochloride.

$^1$H Nuclear magnetic resonance (NMR) spectra were in all cases consistent with the proposed structures. Characteristic chemical shifts (6) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: $CDCl_3$, deuterochloroform; $d_6$-DMSO, deuterodimethylsulphoxide; and $CD_3OD$, deuteromethanol.

Mass spectra, MS (m/z), were recorded using either electrospray ionisation (ESI) or atmospheric pressure chemical ionisation (APCI). When relevant, m/z data provided may include isotopes $^{35}Cl$, $^{37}Cl$, $^{79}Br$, $^{81}Br$ and combinations there of.

Automated Preparative High Performance Liquid Chromatography (Auto-HPLC)

Certain compounds of the Examples and Preparations were purified using Automated Preparative High Performance Liquid Chromatography (HPLC). Reversed-phase HPLC conditions were either on Fraction Lynx systems or on a Trilution system.

In the case of the FractionLynx system, Samples were submitted dissolved in 1 mL of DMSO. Depending on the nature of the compounds and the results of a pre-analysis, the purification was performed under either acidic ('A-HPLC'), or basic ('B-HPLC') conditions at ambient temperature. A-HPLC was carried out on a Sunfire Prep C18 OBD column (19×100 mm, 5 µm). B-HPLC was carried out on an Xterra Prep MS C18 (19×100 mm, 5 µm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

ES+ Cone voltage: 30 v Capillary: 3.20 kv
ES− Cone voltage: −30 v Capillary: −3.00 kv
Desolvation gas: 600 L/hr
Source Temp: 120° C.
Scan range 150-900 Da The fraction collection was triggered by both MS and ELSD.

Quality control (QC) analysis was performed using a LCMS method. Acidic runs were carried out on a Sunfire C18 (4.6×50 mm, 5 µm), basic runs were carried out on a Xterra C18 (4.6×50 mm, 5 µm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

ES+ Cone voltage: 25 v Capillary: 3.30 kv
ES− Cone voltage: −30 v Capillary: −2.50 kv
Desolvation gas: 800 L/hr
Source Temp: 150° C.
Scan range 160-900 Da Where the reversed-phase Trilution system was used (T-HPLC) the conditions were as follows:
Mobile phase A: 0.1% formic acid in water
Mobile phase B: 0.1% formic acid in acetonitrile
Column: Phenomenex C18 Luna 21.5 mm×15 cm with 5 micron particle size
Gradient: 95-5% A over 15 min, 15 min hold, 15 ml/min flow rate
UV: 200 nm-400 nm
Temperature: Room temperature
Liquid Chromatography Mass Spectrometry Unless carried out by Auto-HPLC (under conditions of A-HPLC or B-HPLC) as described just above, or as specifically set out in the Examples and Preparations that follow, LCMS conditions were run according to one of the conditions given below (where ratios of solvents are given, the ratios are by volume):
Acidic 2 Minute LCMS
Mobile phase A: 0.1% formic acid in water
Mobile phase B: 0.1% formic acid in 70% methanol: 30% isopropanol
Column: C18 phase Phenomenex 20×4.0 mm with 3 micron particle size
Gradient: 98-10% A over 1.5 min, 0.3 min hold, 0.2 re-equilibration, 2 ml/min flow rate
UV: 210 nm-450 nm DAD
Temperature: 75° C. Or
Mobile phase A: 0.1% formic acid in water
Mobile phase B: 0.1% formic acid in acetonitrile
Column: C18 phase Phenomenex 20×4.0 mm with 3 micron particle size
Gradient: 70-2% A over 1.5 min, 0.3 min hold, 0.2 re-equilibration, 1.8 ml/min flow rate
UV: 210 nm-450 nm DAD
Temperature: 75° C.
Acidic 4.5 minute LCMS
Mobile phase A: 0.05% formic acid in water
Mobile phase B: acetonitrile
Column: Phenomenex Gemini C18 45×45 mm with 5 micron particle size Gradient: 80-50% A over 0.5 min, 50-2% A over 3 min, 1 min hold, 0.2 min re-equilibration, 2.0 ml/min flow rate
UV: 220 nm-254 nm DAD
Temperature: 40° C.
Acidic 8 Minute LCMS
Mobile phase A: 0.05% formic acid in water
Mobile phase B: acetonitrile
Column: Phenomenex Gemini C18 45×45 mm with 5 micron particle size
Gradient: 80-50% A over 0.5 min, 50-2% A over 3 min, 4.5 min hold, 0.2 min re-equilibration, 2.0 ml/min flow rate
UV: 220 nm-254 nm DAD
Temperature: 40° C.
Acidic 6 Minute LCMS
Mobile phase A: 0.1% formic acid in water
Mobile phase B: 0.1% formic acid in acetonitrile
Column: C18 phase Waters Sunfire 50×4.6 mm with 5 micron particle size
Gradient: 95-5% A over 3 min, 1 min hold, 2 min re-equilibration, 1.5 ml/min flow rate
UV: 210 nm-450 nm DAD
Temperature: 50° C.
Basic 6 Minute LCMS
Mobile phase A: 0.1% ammonium hydroxide in water
Mobile phase B: 0.1% ammonium hydroxide in acetonitrile
Column: C18 phase Fortis 50×4.6 mm with 5 micron particle size
Gradient: 95-5% A over 3 min, 1 min hold, 2 min re-equilibration, 1 ml/min flow rate
UV: 210 nm-450 nm DAD
Temperature: 50° C.
Acidic 30 Minute LCMS
Mobile phase A: 0.1% formic acid in water
Mobile phase B: 0.1% formic acid in acetonitrile
Column: Phenomenex C18 phase Gemini 150×4.6 mm with 5 micron particle size
Gradient: 98-2% A over 18 min, 2 min hold, 1 ml/min flow rate
UV: 210 nm-450 nm DAD
Temperature: 50° C.
Basic 30 Minute LCMS
Mobile phase A: 10 mM ammonium acetate in water
Mobile phase B: 10 mM ammonium acetate in methanol
Column: Phenomenex Phenyl Hexyl 150×4.6 mm with 5 micron particle size
Gradient: 98-2% A over 18 min, 2 min hold, 1 ml/min flow rate
UV: 210 nm-450 nm DAD
Temperature: 50° C.

In the tabulated experimental details that follow, the Examples and Preparations were prepared according to the corresponding reference method (i.e. Method A, Method B, Preparation 34, and so on). The skilled person will appreciate that, in the synthesis of any specific Example or Preparation, it may be desirable to make minor variations to the reaction conditions of the reference method (e.g. with regard to solvent, temperature and so on).

EXAMPLE 1

Illustrates Method A

4-{[(5-Chloro-6-isobutoxypyridin-3-yl)oxy]methy}-2,5-difluoro-N-(methylsulfonyl)benzamide diethylamine salt

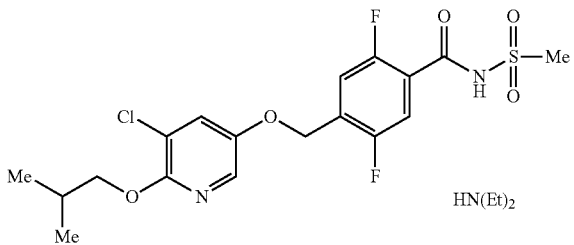 [SMILES: CC(C)COc1ncc(OCc2cc(F)c(C(=O)NS(C)(=O)=O)cc2F)cc1Cl ; "HN(Et)2"]

To 4-((5-chloro-6-isobutoxypyridin-3-yloxy)methyl)-2,5-difluorobenzoic acid (Preparation 5, 113 mg, 0.30 mmol) in dichloromethane (10 mL) was added O-(7-azabenzotriazol-1-yl)-N,N,N',N'-tetramethyluronium hexafluorophosphate (127 mg, 0.30 mmol), methyl sulphonamide (87 mg, 0.91 mmol) and N,N-diisopropylethylamine (0.17 ml, 0.92 mmol) and the mixture stirred at 40° C. overnight under nitrogen. The solvent was evaporated under reduced pressure and the residue dissolved in ethyl acetate (10 mL) and washed with saturated aqueous ammonium chloride solution (2×10 mL). The solution was dried over magnesium sulphate and filtered. The solvent was removed under reduced pressure to give an oil (210 mg). The crude residue was dissolved in dimethylsulphoxide (50 mg/mL) and purified by B-HPLC to afford the title compound (88.8 mg, 66%) as the diethylamine salt.

LCMS Rt=4.23 minutes LCMS Rt=4.23 minutes MS m/z 449 [MH]+,

The following examples were prepared according to Method A, as described for Example 1 above, using the corresponding benzoic acid.

| Ex | Name | Data |
|---|---|---|
| 29 | 4-((5-Chloro-6-isopropoxypyridin-3-yl)methoxy)-2,5-difluoro-N-(methylsulfonyl)benzamide diethylamine salt | 1H NMR (400 MHz, d6-DMSO): δ 1.26 (d, 6H), 3.33 (s, 3H), 5.19 (m, 1H), 5.21 (s, 2H), 7.59 (m, 2H), 7.80 (m, 1H), 7.93 (m, 1H). LCMS Rt = 4.15 min. MS m/z 433 [MH]− |
| 3 | 4-{[(5-Chloro-6-isobutoxypyridin-3-yl)oxy]methyl}-N-(methylsulfonyl)benzamide diethylamine salt | LCMS Rt = 3.97 min. MS m/z 413 [MH]+ |
| 4 | 4-((5-Chloro-6-methoxypyridin-3-yloxy)methyl)-N-(cyclopropylsulfonyl)-2,5-difluorobenzamide | LCMS Rt = 3.09 min. MS m/z 433 [MH]+, |
| 5 | 4-((5-Chloro-6-isobutoxypyridin-3-yloxy)methyl)-3-methoxy-N-(methylsulfonyl)benzamide diethylamine salt | LCMS Rt = 2.64 min. MS m/z 441 [MH]− |

-continued

| Ex | Name | Data |
|---|---|---|
| 6 | 4-((5-Chloro-6-methoxypyridin-3-yloxy)methyl)-N-(methylsulfonyl)benzamide | $^1$H NMR (400 MHz, CD$_3$OD): δ 3.37 (s, 3H), 3.96 (s, 3H), 5.22 (s, 2H), 7.34 (m, 1H), 7.61 (m, 2H), 7.69 (m, 1H), 7.94 (m, 2H). LCMS Rt = 1.56 min. MS m/z 371[MH]$^+$ |

EXAMPLE 7

Illustrates Method B

4-{[(6-Methoxypyridin-3-yl)oxy]methyl}-N-(methylsulfonyl)benzamide

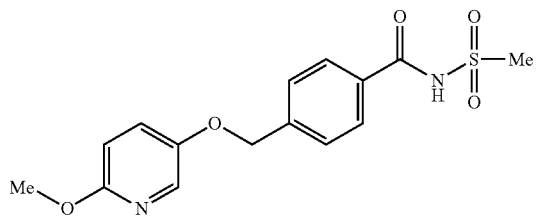 [SMILES: COc1ccc(OCc2ccc(C(=O)NS(C)(=O)=O)cc2)cn1]

Potassium carbonate (138 mg, 1.0 mmol), a solution of methyl 4-(bromomethyl)benzoate in DMF (0.476 M, 1.05 mL, 0.5 mmol) and 6-methoxypyridin-3-ol (62.5 mg, 0.5 mmol) in DMF (1.5 mL) was added into an ArQule™ vial. The reaction vessel was sealed and heated at 65° C. for 6 hours. After cooling, the residue was partitioned between EtOAc and water (2.5 mL). The organic layer was separated and concentrated in vacuo. The resulting residue was dissolved in THF (2.5 mL) and aqueous lithium hydroxide (5 M, 0.5 mL) was added. The reaction mixture was stirred at 55° C. for 18 hours. Water (3 mL) was then added and the resulting mixture was washed with diethyl ether (1 mL), acidified with aqueous hydrochloric acid (2 M, 2 mL) and extracted with EtOAc. The organic layer was evaporated and to the remaining residue N,N-dimethylpyridin-4-amine in DCM (1 M, 1 mL), N-[3-(dimethylamino)propyl]-N'-ethylcarbodiimide hydrochloride in DCM (1 M, 1 mL) and methanesulphonamide in DCM (1 M, 1 mL) was added. The reaction vessel was sealed and stirred at room temperature for 18 hours. The resulting mixture was partitioned between DCM (2 mL) and aqueous hydrochloric acid (2 M, 2 mL). The organic layer was passed through a phase separation Cartridge™ and evaporated to dryness. The crude residue was dissolved in DMSO (50 mg/mL) and purified by preparative HPLC to afford the title compound (21.4 mg, 15%).

LCMS Rt=3.00 minutes MS m/z 337 [MH]$^+$, 335 [M-H]$^-$,
Preparative Acidic Conditions
Column: SunFire C18, 5 um 19×100 mm
Temperature: Ambient
Detection: ELSD-MS
Fractionlynx 1
Injection Volume: 1000 uL
Flow Rate: 18 mL/min
Mobile Phase: A: H$_2$O+0.1% formic acid, B: acetonitrile+ 0.1% formic acid
Gradient (Time/mins, % B)-(0-1, 5),(1-7, 5-98),(7-9, 98),(9-9.1, 98-5),(9.1-10, 5)
Acidic Analytical (QC)
Column: SunFire C18, 5 um 4.6×50 mm
Temperature: Ambient
Detection: UV 225 nm-ELSD-MS
System/Data file: CTC-MUX1 Injection volume: 5 uL
Flow rate: 1.5 mL/min
Mobile phase: A: H$_2$O+0.1% formic acid, B: acetonitrile+ 0.1% formic acid
Gradient (Time/mins, % B)-(0,5),(3,95),(4,95),(4.1,5),(5,5)

EXAMPLE 8

4-{[(2-Ethoxypyridin-3-yl)oxy]methyl}-N-(methylsulfonyl)benzamide

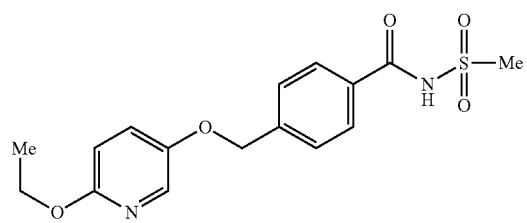 [SMILES: CCOc1ccc(OCc2ccc(C(=O)NS(C)(=O)=O)cc2)cn1]

This was prepared using the same procedure as in Example 7 above, using 2-ethoxypyridin-3-ol to afford the title compound (41.2 mg, 23%).

LCMS Rt=3.06 minutes MS m/z 351 [MH]$^+$

EXAMPLE 9

Illustrates Method C

N-(methylsulfonyl)-4-{[6-(trifluoromethyl)pyridin-3-yl]methoxy}benzamide formate salt

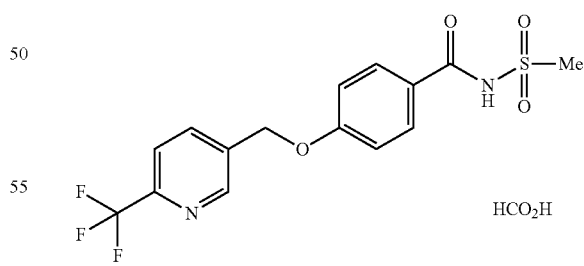

To methyl 4-hydroxybenzoate (22.8 mg, 0.15 mmol) and [6-(trifluoromethyl)pyridin-3-yl]methanol (22.1 mg, 0.125 mmol) in DCM (1 mL) was added N,N,N'N'-tetramethylazodicarboxylate (43 mg) and polymer supported triphenylphosphine (3 mmol/g, 125 mg, 0.375 mmol). The reaction was shaken at 30° C. for 16 hours, filtered, diluted with aqueous citric acid solution (2.5%, 1 mL) and extracted with DCM (3×1 mL). The combined organics were concentrated in vacuo. The resulting crude residue was dissolved in THF (0.625 mL), treated with aqueous lithium hydroxide solution (2 M, 0.625 mL, 1.25 mmol) and the mixture shaken at 50° C. for 16 hours. The solvent was removed in vacuo, the residue dissolved in aqueous citric acid solution (4 M, 0.4 mL, 1.6 mmol) and extracted with EtOAc (3×1 mL), dried over sodium sulfate, filtered and the solvent removed in vacuo. To the resulting crude residue DCM (1 mL), methanesulphonamide (12 mg, 0.126 mmol), 1-[3-(dimethylamino)propyl]-3-ethylcarbodiimide hydrochloride (EDCI) (72 mg, 0.377 mmol) and DMAP (23 mg, 0.188 mmol) was added and the mixture was shaken at 30° C. for 16 hours. The solvent was removed under reduced pressure and the resulting crude product was purified by preparative HPLC to afford the title compound.

LCMS Rt=3.00 minutes MS m/z 375 [MH]$^+$
LCMS Conditions

| Column | Xbridge C18 2.1 × 50 mm 5 μm |
|---|---|
| Temperature | 50° C. |
| Mobile Phase A | 0.0375% TFA in water |
| Mobile Phase B | 0.01875% TFA in acetonitrile |
| Gradient - Initial | 1% B |
| Time 0.00 mins | 1% B |
| Time 0.60 mins | 5% B |
| Time 4.00 mins | 100% B |
| Time 4.30 mins | 1% B |
| Time 4.70 mins | 1% B |
| Flow rate | 0.8 mL/min |
| Injection volume | 2 μl |
| Agilent 1200 HPLC/1956 MSD/SEDEX 75 ELSD | |
| Ionization Mode | API-ES |
| Polarity | Positive |
| HPLC conditions | |
| Column: | Kromasil Eternity-5-C18 150*30 mm*5 um |
| Detection: | UV |
| Flow rate | 30 mL/min |
| Mobile phase: | A water + 0.225% formic acid; B acetonitrile |
| Gradient (Time/mins, % B) - (0-10, 10-60), (10-11, 100) | |

EXAMPLE 10

Illustrates Method D 4-((5-Chloropyridin-3-yloxy)methyl)-N-(methylsulfonyl)benzamide

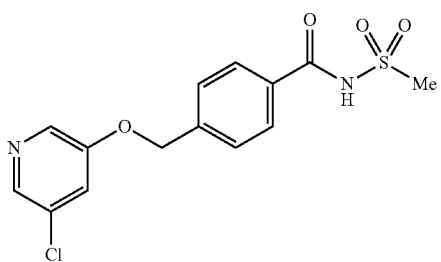 [SMILES: CS(=O)(=O)NC(=O)c1ccc(COc2cncc(Cl)c2)cc1]

To a suspension of 4-{[(5-chloropyridin-3-yl)oxy]methyl}benzoic acid (Preparation 17, 0.16 g, 0.60 mmol) in THF (6 mL) was added WSCDI (0.1 g, 0.62 mmol) and the reaction was heated at reflux for 30 minutes. The reaction mixture was cooled to room temperature and methanesulphonamide (0.060 g, 0.64 mmol) and DBU (0.09 g, 0.060 mmol) were added. The reaction mixture was stirred at room temperature for 1 hour and then partitioned between DCM (30 mL) and aqueous hydrochloric acid (1 M, 8 mL). The organic layer was separated and dried over magnesium sulfate and evaporated in vacuo. The resulting crude was triturated with diethyl ether (4 mL) and methanol (1 mL) to afford the title compound as a beige solid (0.053 g, 51%).

$^1$H NMR (400 MHz, d$_6$-DMSO): δ 3.38 (s, 3H), 5.15 (s, 2H), 7.78 (d, 2H), 7.83 (s, 1H), 7.95 (d, 2H), 8.12 (s, 1H), 8.18 (s, 1H).

LCMS Rt=2.11 minutes MS m/z 341 [MH]$^+$

EXAMPLE 11

Illustrates Method E 4-({[5-Chloro-6-(3,3,3-trifluoropropoxy)pyridin-3-yl]oxy}methyl)-2,5-difluoro-N-(methylsulfonyl)benzamide

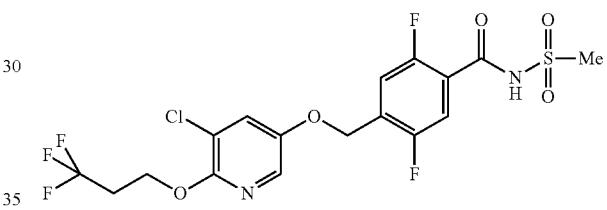

Potassium carbonate (61 mg, 0.229 mmol) was added to a solution of 5-chloro-6-(3,3,3-trifluoropropoxy)pyridin-3-ol (Preparation 67, 45 mg, 0.19 mmol) in DMSO (2 mL) and the reaction mixture was stirred under a nitrogen atmosphere at room temperature for 5 minutes. 4-(Bromomethyl)-2,5-difluoro-N-(methylsulfonyl)benzamide (Preparation 10, 63 mg, 0.19 mmol) was then added and the resulting mixture stirred under nitrogen at room temperature for 120 hours. The reaction mixture was diluted with aqueous hydrochloric acid solution (2 M, 15 mL), extracted with EtOAc (20 mL). The organic layer was washed with aqueous hydrochloric acid solution (2 M, 2×10 mL), dried over magnesium sulfate, filtered and evaporated in vacuo. The resulting crude solid was triturated with TBME/heptane (2:1), washed with heptane and dried in vacuo to yield the title compound as an off-white solid (73 mg, 74%):

$^1$H NMR (400 MHz, d$_6$-DMSO): δ 2.70-2.88 (m, 2H), 3.36 (s, 3H), 4.49 (t, 2H), 5.24 (s, 2H), 7.59 (m, 2H), 7.86 (d, 1H), 7.97 (d, 1H).

LCMS Rt=1.62 minutes MS m/z 487 [M-H]$^-$

The following examples were prepared according to Method E, as described for Example 11 above, using the corresponding pyridinol and benzyl bromide.

| Ex | Name | Data |
|---|---|---|
| 12 | 4-({[5-Chloro-6-(trifluoromethyl)pyridin-3-yl]oxy}methyl)-2,5-difluoro-N-(methylsulfonyl)benzamide | $^1$H NMR (400 MHz, d$_6$-DMSO): δ 3.37 (s, 3H), 5.42 (s, 2H), 7.61 (m, 2H), 8.13 (s, 1H), 8.52 (s, 1H). LCMS Rt = 1.79 min. MS m/z 443[MH]$^-$ |

| Ex | Name | Data |
|---|---|---|
| 13 | 4-((5-Chloro-6-(2-fluoro-2-methylpropoxy)pyridin-3-yloxy)methyl)-2,5-difluoro-N-(methylsulfonyl)benzamide | $^1$H NMR (400 MHz, d$^6$-DMSO): δ 1.42 (d, 6H), 3.35 (s, 3H), 4.32 (d, 2H), 5.25 (s, 2H), 7.56-7.63 (m, 2H), 7.87 (d, 1H), 7.96 (d, 1H).<br>LCMS Rt = 3.67 min. MS m/z 467[MH]$^+$ |
| 14 | 4-((5-Chloro-6-((1-methylcyclopropyl)methoxy)pyridin-3-yloxy)methyl)-2,5-difluoro-N-(methylsulfonyl)benzamide | LCMS Rt = 3.97 min.<br>MS m/z 459[MH]$^-$ |
| 15 | 4-{[6-d9-tert-Butoxy-5-chloropyridin-3-yl)oxy]methyl}-2,5-difluoro-N-(methylsulfonyl)benzamide | 1H NMR (400 MHz, CDCl$_3$): δ 3.41 (s, 3H), 5.13 (s, 2H), 7.38 (s, 1H), 7.42 (s, 1H), 7.78 (m, 1H), 7.82 (m, 1H), 8.81 (br, 1H).<br>LCMS Rt = 2.68 min.<br>MS m/z 456 [MH]$^-$ |
| 16 | 4-((5-Chloro-6-(2,2,2-trifluoroethoxy)pyridin-3-yloxy)methyl)-2,5-difluoro-N-(methylsulfonyl)benzamide | $^1$H NMR (400 MHz, d$_6$-DMSO): δ 3.35 (s, 3H), 5.02 (q, 2H), 5.27 (s, 2H), 7.57-7.64 (m, 2H), 7.95 (d, 1H), 8.02 (d, 1H), 12.39 (br s, 1H).<br>LCMS Rt = 3.67 min. MS m/z 473[MH]$^-$ |
| 17 | 4-((5-Chloro-6-(cyclopropylmethoxy)pyridin-3-yloxy)methyl)-2,5-difluoro-N-(methylsulfonyl)benzamide | $^1$H NMR (400 MHz, d$_6$-DMSO): δ 0.31-0.35 (m, 2H), 0.53-0.57 (m, 2H), 1.19-1.28 (m, 1H), 3.28 (s, 3H), 4.12 (d, 2H), 5.22 (s, 2H), 7.52-7.60 (m, 2H), 7.83 (d, 1H), 7.94 (d, 1H).<br>LCMS Rt = 3.81 min. MS m/z 447[MH]$^+$ |
| 18 | 4-((6-tert-Butoxy-5-chloropyridin-3-yloxy)methyl)-2,5-difluoro-N-(methylsulfonyl)benzamide | $^1$H NMR (400 MHz, d$_6$-DMSO): δ 1.52 (s, 9H), 3.30 (s, 3H), 5.22 (s, 2H), 7.53-7.62 (m, 2H), 7.77 (d, 1H), 7.95 (d, 1H).<br>LCMS Rt = 4.02 min. MS m/z 447[MH]$^-$ |
| 19 | 4-((5-Chloro-6-((3,3-difluorocyclobutyl)methoxy)pyridin-3-yloxy)methyl)-2,5-difluoro-N-(methylsulfonyl)benzamide | LCMS Rt = 3.78 min.<br>MS m/z 495[MH]$^-$ |
| 20 | 4-{[(5-Chloropyridin-3-yl)oxy]methyl}-2,5-difluoro-N-(methylsulfonyl)benzamide | LCMS Rt = 1.99 min.<br>MS m/z 377[MH]$^+$ |
| 21 | 4-{[(5-Chloro-6-d7-isopropoxypyridin-3-yl)oxy]methyl}-2,5-difluoro-N-(methylsulfonyl)benzamide | $^1$H NMR (400 MHz, d$_6$-DMSO): δ 3.42 (s, 3H), 5.15 (s, 2H), 7.35-7.48 (m, 1.5H), 7.75-7.88 (m, 2H), 9.7-9.9 (br, 1H).<br>LCMS Rt = 3.33 min.<br>MS m/z 440[MH]$^-$ |
| 22 | 4-({[5-Chloro-6-(2,2,3,3-tetrafluoropropoxy)pyridin-3-yl]oxy}methyl)-2,5-difluoro-N-(methylsulfonyl)benzamide | $^1$H NMR (400 MHz, CDCl$_3$): δ 3.44 (s, 3H), 4.69-4.76 (m, 1H), 5.17 (d, 2H), 5.92-6.21 (m, 1H), 7.40-7.44 (q, 1H), 7.44-7.45 (d, 1H), 7.78-7.79 (d, 1H), 7.84-7.87 (d, 1H), 8.81-8.84 (br, 1H).<br>LCMS Rt = 1.50 min. MS m/z 507[MH]$^+$ |

| Ex | Name | Data |
|---|---|---|
| 23 | 4-{[(5-Chloro-6-fluoropyridin-3-yl)oxy]methyl}-2,5-difluoro-N-(methylsulfonyl)benzamide | $^1$H NMR (400 MHz, CDCl$_3$): δ 3.45 (s, 3H), 5.20 (s, 2H), 7.40-7.45 (m, 1H), 7.49-7.51 (m, 1H), 7.83-7.84 (m, 1H), 7.85-7.89 (m, 1H), 8.81-8.85 (m, 1H). LCMS Rt = 1.30 min. MS m/z 395[MH]$^+$ |
| 24 | 4-{[(5-Chloro-6-d1-isopropoxypyridin-3-yl)oxy]methyl}-2,5-difluoro-N-(methylsulfonyl)benzamide | $^1$H NMR (400 MHz, CDCl$_3$): δ 1.37 (s, 6H), 3.45 (s, 3H), 5.15 (s, 2H), 7.39-7.40 (m, 1H), 7.42-7.46 (m, 1H), 7.78-7.79 (m, 1H), 7.83-7.87 (m, 1H), 8.83 (m, 1H). LCMS Rt = 1.85 min. MZ m/z 436 [MH]$^+$ |
| 25 | 4-({[5-Chloro-6-(2,2,3,3,3-pentafluoropropoxy)pyridin-3-yl]oxy}methyl)-2,5-difluoro-N-(methylsulfonyl)benzamide | $^1$H NMR (400 MHz, CDCl$_3$): δ 3.45 (s, 3 H), 4.85 (m, 2 H), 5.18 (s, 2 H), 7.41-7.45 (m, 1 H), 7.46 (d, 1 H), 7.79 (d, 1 H), 7.87 (d, 1 H), 8.82 (d, 1 H). LCMS Rt = 1.76 min. MS m/z 525 [MH]$^+$ |
| 26 | 2,5-Difluoro-N-(methylsulfonyl)-4-({[6-(trifluoromethyl)pyridin-3-yl]oxy}methyl)benzamide | $^1$H NMR (400 MHz, d$_6$-DMSO): δ 3.36 (s, 3H), 5.38 (s, 2H), 7.63 (m, 2H), 7.74 (m, 1H), 7.88 (d, 1H), 8.56 (d, 1H). LCMS Rt = 1.47 min. MS m/z 411 [MH]$^+$. |
| 27 | 4-((5-Chloro-6-(1,1,1-trifluoropropan-2-yloxy)pyridin-3-yloxy)methyl)-2,5-difluoro-N-(methylsulfonyl)benzamide | $^1$H NMR (400 MHz, CDCl$_3$): δ 1.52 (m, 3H), 3.44 (s, 3H), 5.17 (s, 2H), 5.68 (m, 1H), 7.43 (m, 2H), 7.76 (m, 1H), 7.85 (m, 1H), 8.83 (s, 1H) LCMS Rt = 3.59 min. MS m/z 487 [MH]$^-$ |
| 28 | 4-((5-Chloro-6-methoxypyridin-3-yloxy)methyl)-2,5-difluoro-N-(methylsulfonyl)benzamide | $^1$H NMR (400 MHz, d$_6$-DMSO): δ 3.38 (s, 3H), 3.85 (s, 3H), 5.25 (s, 2H), 7.56 (m, 1H), 7.62 (m, 2H), 7.80 (m, 1H) LCMS Rt = 3.23 min. MS m/z 405[MH]$^-$ |
| 2 | 4-((5-Chloro-6-isopropoxypyridin-3-yloxy)methyl)-2,5-difluoro-N-(methylsulfonyl)benzamide | $^1$H NMR (400 MHz, d$_6$-DMSO): δ 1.25 (m, 6H), 3.33 (s, 3H), 5.19 (m, 1H), 5.21 (s, 2H), 7.59 (m, 2H), 7.80 (m, 1H), 7.93 (m, 1H). LCMS Rt = 4.15 min. MS m/z 433[MH]$^-$ |
| 30 | 5-Chloro-4-((5-chloro-6-(1,1,1,3,3,3-hexafluoropropan-2-yloxy)pyridin-3-yloxy)methyl)-2-fluoro-N-(methylsulfonyl)benzamide | $^1$H NMR (400 MHz, CDCl$_3$): δ 3.45 (s, 3H), 5.18 (s, 2H), 6.36 (m, 1H), 7.52 (m, 1H), 7.80 (m, 1H), 8.16 (m, 1H), 8.78 (s, 1H), LCMS Rt = 3.89 min. MS m/z 557 [MH]– |
| 31 | 5-Chloro-4-((5-chloro-6-(1,1,1-trifluoropropan-2-yloxy)pyridin-3-yloxy)methyl)-2-fluoro-N-(methylsulfonyl)benzamide | $^1$H NMR (400 MHz, CDCl$_3$): 1.52 (m, 3H), 3.44 (s, 3 H), 5.15 (s, 2H), 5.68 (m, 1H), 7.45 (m, 1H), 7.48 (m, 1H), 7.78 (m, 1H), 8.15 (m, 1H), 8.80 (s, 1H). LCMS Rt = 3.75 min. MS m/z = 503 [MH]$^-$ |
| 32 | 4-{[(6-d9-tert-Butoxy-5-chloropyridin-3-yl)oxy]methyl}-5-chloro-2-fluoro-N-(methylsulfonyl)benzamide | $^1$H NMR (400 MHZ, CDCl$_3$): δ 3.42 (s, 3H), 5.15 (s, 2H), 7.38 (s, 1H), 7.48 (s, 1H), 7.79 (s, 1H), 8.15 (s, 1H), 8.80 (br, 1H). LCMS Rt = 2.64 min. MS m/z 472 [MH]$^-$ |

-continued

| Ex | Name | Data |
|---|---|---|
| 33 | 5-Chloro-4-{[(5-chloro-6-methoxypyridin-3-yl)oxy]methyl}-2-fluoro-N-(methylsulfonyl)benzamide | $^1$H NMR (400 MHz, d$_6$-DMSO): δ 3.35 (s, 3H), 3.89 (s, 3H), 5.24 (s, 2H), 7.63 (d, 1H), 7.83 (d, 1H), 7.86 (d, 1H), 7.99 (d, 1H). LCMS Rt = 2.50 min. MS m/z 424[MH]$^+$ |
| 34 | 5-Chloro-4-{[(5-chloro-6-d1-isopropoxypyridin-3-yl)oxy]methyl}-2-fluoro-N-(methylsulfonyl)benzamide | $^1$H NMR (400 MHz, CDCl$_3$): δ 1.39 (s, 6H), 3.42 (s, 3H), 5.17 (s, 2H), 7.38 (s, 1H), 7.49 (m, 1H), 7.79 (s, 1H), 8.16 (m, 1H), 8.80 (br, 1H) LCMS Rt = 1.95 min. MS m/z 452 [MH]$^+$ |
| 35 | 5-Chloro-4-((5-chloro-6-isopropoxypyridin-3-yloxy)methyl)-2-fluoro-N-(methylsulfonyl)benzamide | $^1$H NMR (400 MHz, CDCl$_3$): δ 1.35 (s, 6H), 3.45 (s, 3H), 5.20 (s, 2H), 5.25 (m, 1H), 7.40 (d, 1H), 7.50 (m, 1H), 7.80 (d, 1H), 8.15 (d, 1H), 8.80 (br, 1H). LCMS Rt = 3.79 min. MS m/z 449 [MH]$^-$ |
| 36 | 5-Chloro-4-({[5-chloro-6-(1,1-difluoro-2-methylpropyl)pyridin-3-yl]oxy}methyl)-2-fluoro-N-(methylsulfonyl)benzamide | $^1$H NMR (400 MHz, CDCl$_3$): δ 1.06-1.07 (d, 6H), 2.73-2.88 (m, 1H), 3.44 (s, 3H), 5.24 (s, 2H), 7.39-7.40 (d, 1H), 7.48-7.51 (d, 1H), 8.16-8.18 (d, 1H), 8.34-8.35 (d, 1H), 8.80-8.84 (m, 1H). LCMS Rt = 1.67 min. MS m/z 485[MH]$^+$ |
| 37 | 5-Chloro-4-({[5-chloro-6-(2,2,3,3-tetrafluoropropoxy)pyridin-3-yl]oxy}methyl)-2-fluoro-N-(methylsulfonyl)benzamide | $^1$H NMR (400 MHz, CDCl$_3$): δ 3.44 (s, 3H), 4.70-4.77 (m, 1H), 5.16 (d, 2H), 5.93-6.22 (m, 1H), 7.46-7.47 (d, 1H), 7.47-7.50 (d, 1H), 7.80 (d, 1H), 8.15-8.17 (d, 1H), 8.77-8.80 (m, 1H) LCMS Rt = 1.52 min. MS m/z 523[MH]$^+$ |
| 38 | 4-{[(6-tert-Butyl-5-chloropyridin-3-yl)oxy]methyl}-5-chloro-2-fluoro-N-(methylsulfonyl)benzamide | $^1$H NMR (d$_6$-DMSO): δ 1.45 (s, 9H), 3.40 (s, 3H), 5.30 (s, 2H), 7.65 (m, 2H), 7.8 (m, 1H), 8.30 (m, 1H). LCMS Rt = 1.79 min. MS m/z 447 [MH]$^-$ |
| 39 | 5-Chloro-4-{[(5-chloro-6-d7-isopropoxypyridin-3-yl)oxy]methyl}-2-fluoro-N-(methylsulfonyl)benzamide | $^1$H NMR (400 MHz, CDCl$_3$): δ 3.45 (s, 3H), 5.14 (d, 2H), 7.40-7.41 (m, 1H), 7.49-7.52 (m, 1H), 7.79-7.80 (m, 1H), 8.14-8.16(m, 1H), 8.80 (m, 1H). LCMS Rt = 1.53 min. MS m/z 458 [MH]$^+$ |
| 40 | 5-Chloro-4-{[(5-chloro-6-fluoropyridin-3-yl)oxy]methyl}-2-fluoro-N-(methylsulfonyl)benzamide | $^1$H NMR (400 MHz, CDCl$_3$): δ 3.45 (s, 3H), 5.20 (d, 2H), 7.46-7.55 (m, 2H), 7.86 (d, 1H), 8.17 (d, 1H), 8.89 (d, 1H). LCMS Rt = 1.57 min. MS m/z 411 [MH]$^+$ |
| 41 | 5-Chloro-4-({[5-chloro-6-(difluoromethoxy)pyridin-3-yl]oxy}methyl)-2-fluoro-N-(methylsulfonyl)benzamide | $^1$H NMR (400 MHz, CDCl$_3$): δ 3.45 (s, 3H), 5.19 (d, 2H), 7.37 (t, 1H), 7.49 (d, 1H), 7.51 (d, 1H), 7.85 (d, 1H), 8.17 (d, 1H), 8.78 (d, 1H). LCMS Rt = 1.72 min. MS m/z 459 [MH]$^+$ |

-continued

| Ex | Name | Data |
|---|---|---|
| 42 | 5-Chloro-4-{[(5-chloro-6-cyclopropylpyridin-3-yl)oxy]methyl}-2-fluoro-N-(methylsulfonyl)benzamide | $^1$H NMR (400 MHz, d$^6$-DMSO): δ 0.87-0.92 (m, 2H), 0.93-1.00 (m, 2H), 2.34-2.43 (m, 1H), 3.37 (s, 3H), 5.27 (s, 2H), 7.64 (d, 1H), 7.71 (d, 1H), 7.84 (d, 1H), 8.26 (d, 1H). LCMS Rt = 1.74 min. MS m/z 433 [MH]$^+$ |
| 43 | 5-Chloro-4-({[5-chloro-6-(2,2,2-trifluoroethoxy)pyridin-3-yl]oxy}methyl)-2-fluoro-N-(methylsulfonyl)benzamide | $^1$H NMR (400 MHz, d$_6$-DMSO): δ 3.34 (s, 3H), 5.09 (m, 2H), 5.25 (s, 2H), 7.63 (d, 1H), 7.82 (d, 1H), 7.96 (d, 1H), 8.02 (d, 1H). |
| 44 | 5-Chloro-4-({[5-chloro-6-(3,3,3-trifluoropropoxy)pyridin-3-yl]oxy}methyl)-2-fluoro-N-(methylsulfonyl)benzamide | $^1$H NMR (400 MHz, d$_6$-DMSO): δ 2.70-2.89 (m, 2H), 3.35 (s, 3H), 4.50 (t, 2H), 5.23 (s, 2H), 7.63 (d, 1H), 7.83 (d, 1H), 7.88 (d, 1H), 7.99 (d, 1H). LCMS Rt = 3.68 min. MS m/z 503 [MH]$^-$ |
| 45 | 5-Chloro-4-({[5-chloro-6-(2-fluoro-2-methylpropoxy)pyridin-3-yl]oxy}methyl)-2-fluoro-N-(methylsulfonyl)benzamide | $^1$H NMR (400 MHz, d$_6$-DMSO): δ 1.41 (d, 6H), 3.35 (s, 3H), 4.31 (d, 2H), 5.23 (s, 2H), 7.62 (d, 1H), 7.82 (d, 1H), 7.87 (d, 1H), 7.96 (d, 1H). LCMS Rt = 3.50 min. MS m/z 483 [MH]$^+$ |
| 46 | 5-Chloro-4-({[5-chloro-6-(2,2,3,3,3-pentafluoropropoxy)pyridin-3-yl]oxy}methyl)-2-fluoro-N-(methylsulfonyl)benzamide | $^1$H NMR (400 MHz, d$_6$-DMSO): δ 3.34 (s, 3H), 5.09 (m, 2H), 5.25 (s, 2H), 7.63 (d, 1H), 7.82 (d, 1H), 7.96 (d, 1H), 8.02 (d, 1H). LCMS Rt = 3.81 min. MS m/z 541 [MH]$^+$ |
| 47 | 4-{[(5-Chloro-6-isobutoxypyridin-3-yl)oxy]methyl}-2-methoxy-N-(methylsulfonyl)benzamide | LCMS Rt = 2.44 min. MS m/z 443 [MH]$^+$ |
| 48 | 4-{[(5-Chloro-6-isopropoxypyridin-3-yl)oxy]methyl}-2-methoxy-N-(methylsulfonyl)benzamide | LCMS Rt 2.33 minutes. MS m/z 429 [MH]$^+$. |

EXAMPLE 49

Illustrates Method F 4-({[5-Chloro-6-(2,2,2-trifluoro-1,1-dimethylethoxy)pyridin-3-yl]oxy}methyl)-2,5-difluoro-N-(methylsulfonyl)benzamide

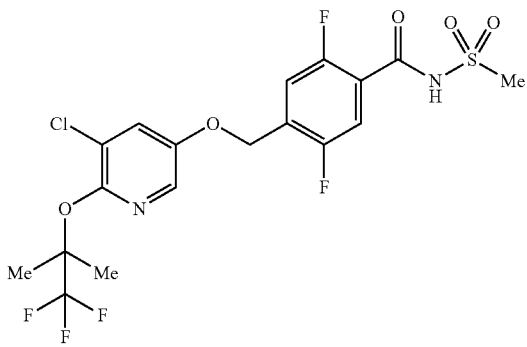 [SMILES: CC(C)(Oc1ncc(OCc2cc(F)c(C(=O)NS(C)(=O)=O)cc2F)cc1Cl)C(F)(F)F]

To a solution of 4-{[(5-chloro-6-fluoropyridin-3-yl)oxy]methyl}-2,5-difluoro-N-(methylsulfonyl)benzamide (Example 23, 0.092 g, 0.233 mmol) in DMSO (1.0 mL) were added 1,1,1-trifluoro-2-methylpropan-2-ol (0.120 g, 0.937 mmol) and caesium carbonate (0.305 g, 0.936 mmol). The mixture was stirred at 100° C. in a pressure vial for 16 hours. Then 1,1,1-trifluoro-2-methylpropan-2-ol (0.120 g, 0.937 mmol) was added to the mixture and heated at 125° C. for another 24 hours. The reaction mixture was diluted with EtOAc (15.0 mL), washed with water (10.0 mL), aqueous citric solution (10%, 10.0 mL) and water (2×10.0 mL). The organic layer was dried over sodium sulfate, filtered and concentrated in vacuo. The resulting residue was suspended in a mixture of heptane and acetone (8:2, 5.0 mL) and sonicated for 2 minutes. The mixture was filtered to yield the title compound as an off-white solid (0.023 g, 20%).

$^1$H NMR (400 MHz, CDCl$_3$): δ 1.76 (m, 6H), 3.44 (s, 3H), 5.16 (s, 2H), 7.40-7.41 (d, 1H), 7.41-7.45 (q, 1H), 7.79 (d, 1H), 7.83-7.87 (q, 1H), 8.81-8.85 (br, 1H).

LCMS Rt=2.79 minutes MS m/z 503 [MH]$^+$

EXAMPLE 50

Illustrates Method G

5-Chloro-2-fluoro-4-[(3-isopropylimidazo[1,5-a]pyridin-6-yl)methoxy]-N-ethylsulfonyl)benzamide

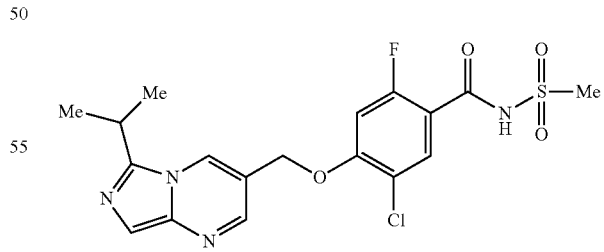

To a stirred solution 3-isopropylimidazo[1,5-a]pyridin-6-yl)methanol (Preparation 28, 116 mg, 0.61 mmol) in THF (3 mL) was added a 60% dispersion of sodium hydride (25.6 mg, 0.64 mmol). When the initial effervescence had subsided the mixture was heated to 55° C. for 30 minutes. The mixture was cooled to room temperature and evaporated to dryness. The residue was treated with a solution of the 5-chloro-2,4-difluoro-N-(methylsulfonyl)benzamide (Preparation 29, 75 mg, 0.278, mmol) in DMSO (2 mL). The resulting solution was stirred at room temperature for 18 hours, diluted with water (7 mL) and extracted with DCM (3×5 mL). The aqueous layer was acidified to ~pH 6 with aqueous hydrochloric acid (2M) and the resulting emulsion was extracted with DCM (2×5 mL). The combined organic extracts were dried over magnesium sulfate, filtered and evaporated. The remaining residue was purified by silica gel chromatography eluting with 1 to 100% of EtOAc/pentane, followed by 0.1% of acetic acid in EtOAc to yield the title compound as a solid (25 mg, 20%). LCMS Rt=1.60 minutes MS m/z 440 [MH]$^+$ $^1$H NMR (400 MHz, CDCl$_3$): δ 1.22 (d, 6H), 3.05-3.12 (m, 4H), 4.90 (s, 2H), 6.50 (d, 1H), 6.75 (d, 1H), 7.15 (s, 1H), 7.20-7.28 (m, 1H), 7.68 (d, 1H), 7.80 (s, 1H).

EXAMPLE 51

Illustrates Method H

3-Chloro-4-[(5-chloro-6-methoxypyridin-3-yl)methoxy]-Nethylsulfonyl)benzamide

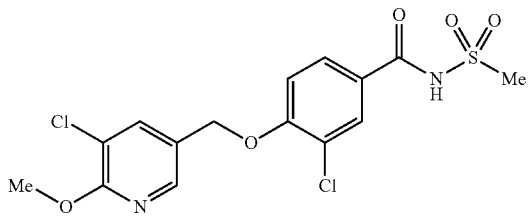 [SMILES: COc1ncc(COc2ccc(C(=O)NS(C)(=O)=O)cc2Cl)cc1Cl]

To a solution of 3-chloro-4-[(5-chloro-6-methoxypyridin-3-yl)methoxy]benzamide (Preparation 31, 27 mg, 0.082 mmol) in THF (5 mL) was added lithium hexamethyldisilazide (0.205 mL, 0.205 mmol) and the mixture stirred for 20 minutes. Methanesulfonyl chloride (15.9 μL, 0.205 mmol) was then added and the reaction mixture was stirred at room temperature for 18 hours, then quenched with aqueous citric acid (10 mL) and extracted with EtOAc (10 mL). The organic layer was dried over sodium sulfate and concentrated in vacuo. The resulting residue was dissolved in DMSO (1 mL) and purified by preparative HPLC to afford the title compound.

LCMS Rt=3.4 minutes MS m/z 405 [MH]$^+$

EXAMPLE 52

4-[(Isoquinolin-5-yloxy)methyl]-Nethylsulfonyl) benzamide

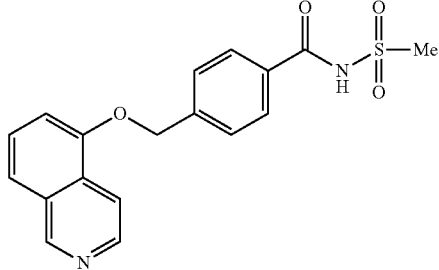 [SMILES: CS(=O)(=O)NC(=O)c1ccc(COc2cccc3cnccc23)cc1]

A solution of 4-[(isoquinolin-5-yloxy)methyl]benzoic acid (140 mg, 0.50 mmol), 2-(1H-7-azabenzotriazol-1-yl)-1, 1,3,3-tetramethyluronium hexafluorophosphate (209 mg, 0.55 mmol) and diisopropylethylamine (0.28 mL; 1.6 mmol) in dichloromethane (3 mL) was stirred at room temperature for 10 minutes under nitrogen. To the clear solution, methane sulphonamide (143 mg, 1.50 mmol) was added and the reaction mixture left to stir at room temperature under nitrogen for 18 hours. The mixture was evaporated to dryness and a portion was purified by preparative HPLC to yield the title compound.

LCMS (acidic 2 min) Rt=0.97 minutes MS m/z 357 [MH]+, 355 [MH]−

EXAMPLE 53

4-[(Isoquinolin-7-yloxy)methyl]-Nethylsulfonyl) benzamide

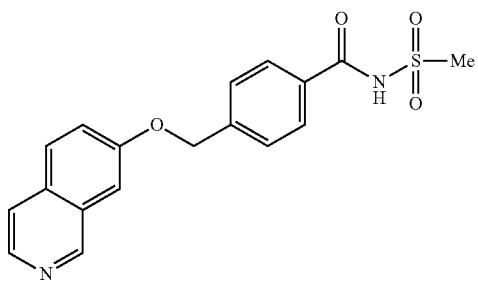 [SMILES: CS(=O)(=O)NC(=O)c1ccc(COc2ccc3ccncc3c2)cc1]

A solution of 4-[(isoquinolin-7-yloxy)methyl]benzoic acid (140 mg, 0.50 mmol), 2-(1H-7-azabenzotriazol-1-yl)-1, 1,3,3-tetramethyluronium hexafluorophosphate (209 mg, 0.55 mmol) and diisopropylethylamine (0.28 mL; 1.6 mmol) in dichloromethane (3 mL) was stirred at room temperature for 10 minutes under nitrogen. To the clear solution, methane sulphonamide (143 mg, 1.50 mmol) was added and the reaction mixture left to stir at room temperature under nitrogen for 18 hours. The mixture was evaporated to dryness and a portion was purified by preparative HPLC to yield the title compound.

LCMS (acidic 2 min) Rt=0.91 minutes MS m/z 357 [MH]+, 355 [MH]−

EXAMPLE 54

N-(Methylsulfonyl)-4-({[2-(2,2,2-trifluoroethoxy) pyridin-3-yl]oxy}methyl)benzamide

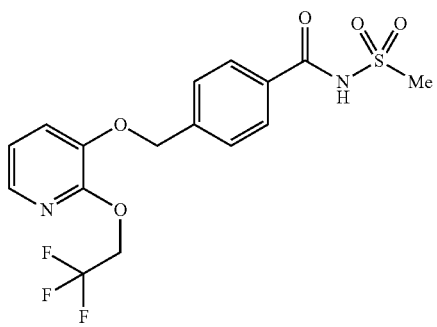 [SMILES: CS(=O)(=O)NC(=O)c1ccc(COc2cccnc2OCC(F)(F)F)cc1]

This was prepared using the same procedure as in Example 7 (Method B) above, using 2-(2,2,2-trifluoroethoxy)pyridin-3-ol (WO2001/074823, Reference Example 98, page 200), to afford the title compound (44 mg, 22%).

LCMS Rt=2.55 minutes MS m/z 405 [MH]+, 403 [M-H]−,
Preparative Acidic Conditions
Column: SunFire C18, 5 um 19×100 mm
Temperature: Ambient
Detection: ELSD-MS
Fractionlynx 1
Injection Volume: 1000 uL
Flow Rate: 18 mL/min
Mobile Phase: A: H2O+0.1% formic acid, B: acetonitrile+ 0.1% formic acid
Gradient (Time/mins, % B)-(0-1, 5),(1-7, 5-98),(7-9, 98),(9-9.1, 98-5),(9.1-10, 5)
Acidic Analytical (QC)
Column: SunFire C18, 5 um 4.6×50 mm
Temperature: Ambient
Detection: UV 225 nm-ELSD-MS
System/Data file: CTC-MUX1 Injection volume: 5 uL
Flow rate: 1.5 mL/min
Mobile phase: A: H2O+0.1% formic acid, B: acetonitrile+ 0.1% formic acid
Gradient (Time/mins, % B)-(0,5),(3,95),(4,95),(4.1,5),(5,5)

The following examples were prepared according to Method E, as described for Example 11 above, using the corresponding pyridinol and benzyl bromide.

EXAMPLE 62

4-({[5-Chloro-4-(trifluoromethyl)pyridin-2-yl]oxy}methyl)-N-(methylsulfonyl)benzamide

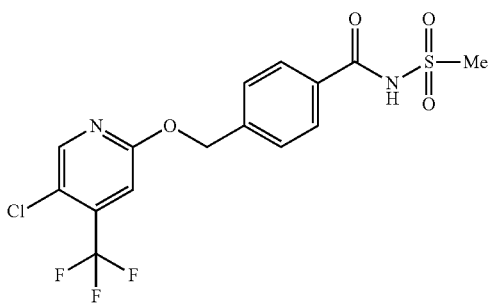 [SMILES: CS(=O)(=O)NC(=O)c1ccc(COc2cc(C(F)(F)F)c(Cl)cn2)cc1]

A solution of 2-(4-bromobenzyloxy)-5-chloro-4-(trifluoromethyl)pyridine (Preparation 106, 0.2 g, 0.54 mmol), methanesulfonamide (0.13 g, 0.162 mmol), tri-tert-butylphosphonium tetrafluoroborate (26 mg, 0.027 mmol), Herrmann's palladacycle (26 mg, 0.027 mmol) and molybdenehexacarbonyl (142 mg, 0.54 mmol) was stirred in dioxane (2 mL). 1,8-Diazabicyclo[5.4.0]undec-7-ene (0.25 mL, 0.162 mmol) was added in one portion, and the vial was sealed and heated in a microwave for 15 minutes at 150° C. The solvent was evaporated in vacuo. The residue was extracted with dichloromethane (30 mL) and washed with water (10 mL). The organic layer was dried over magnesium sulfate, filtered and evaporated in vacuo. The resulting solid was purified on a 10

| Ex | Name | Data |
|---|---|---|
| 55 | 4-({[5-Chloro-4-(trifluoromethyl)pyridin-2-yl]oxy}methyl)-2,5-difluoro-N-(methylsulfonyl)benzamide | LCMS Rt = 2.13 min. MS m/z 462 [M + NH3]+, |
| 56 | 2,5-Difluoro-N-(methylsulfonyl)-4-({[5-(trifluoromethyl)pyridin-2-yl]oxy}methyl)benzamide | 1HNMR (400 MHz, DMSO-d6): δ 3.33 (s, 3H), 5.21 (s, 2H), 6.55 (d, 1H), 7.13-7.22 (m, 1H), 7.56 (dd, 1H), 7.72 (dd, 1H), 8.52 (m, 1H). LCMS Rt = 1.27 minutes MS m/z 411 [MH]+, 409 [M − H]− |
| 57 | 5-Chloro-4-{[(5,6-dicyclopropylpyridin-3-yl)oxy]methyl}-2-fluoro-N-(methylsulfonyl)benzamide diethylamine salt. | LCMS Rt = 2.36 min. MS m/z 439 [MH]+ |
| 58 | 5-Chloro-2-fluoro-4-{[(2-isopropoxypyrimidin-5-yl)oxy]methyl}-N-(methylsulfonyl)benzamide | 1H NMR (400 MHz, DMSO-d6): δ 1.29 (d, 6H), 3.37 (s, 3H), 5.10 (m, 1H), 5.27 (s, 2H), 7.65 (d, 1H), 7.84 (d, 1H), 8.48 (s, 2H). LCMS Rt = 2.84 minutes. MS m/z 418 [MH]+ |
| 59 | 5-Chloro-4-({[6-cyclopropyl-5-(difluoromethoxy)pyridin-3-yl]oxy}methyl)-2-fluoro-N-(methylsulfonyl)benzamide diethylamine salt | Rt = 2.32 minutes MS m/z 465 [MH]+ |
| 60 | 4-{[(3,5-dichloropyridin-2-yl)oxy]methyl}-2,5-difluoro-N-(methylsulfonyl)benzamide | LCMS Rt = 2.35 minutes MS m/z 409[MH]− 1H NMR (400 MHz, MeOD-d4): δ 3.34 (s, 3H), 5.26 (s, 2H), 7.21 (dd, 1H), 7.50 (dd, 1H), 7.86 (m, 1H), 7.95 (dd, 1H). |
| 61 | 4-({[2,6-bis(trifluoromethyl)pyridin-4-yl]oxy}methyl)-2,5-difluoro-N-(methylsulfonyl)benzamide | LCMS Rt = 4.02 minutes MS m/z 477 [M − H]− 1H NMR (400 MHz, MeOD-d4): δ 3.45 (s, 3H), 5.33 (s, 2H), 7.41-7.45 (m, 3H), 7.91 (dd, 1H). | g silica cartridge (eluent:dichloromethane, followed by 3% methanol in dichloromethane) to afford the title compound (55 mg, 25%) as a beige solid.

$^1$H NMR (400 MHz, MeOD-d$_4$): δ 3.88 (s, 3H), 5.45 (s, 2H), 7.22 (s, 1H), 7.80 (d, 2H), 7.90 (d, 2H), 8.18 (s, 1H).

LCMS Rt=3.50 minutes MS m/z 409 [MH]+

EXAMPLE 63

4-{[(5-Chloropyridin-2-yl)oxy]methyl}-N-(methylsulfonyl)benzamide

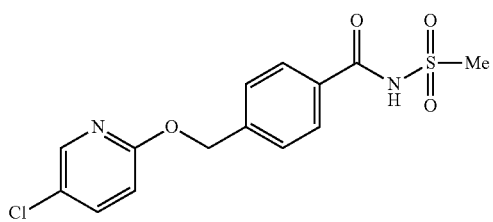 [SMILES: CS(=O)(=O)NC(=O)c1ccc(COc2ccc(Cl)cn2)cc1]

A solution of 2-(4-bromobenzyloxy)-5-chloropyridine (Preparation 107, 0.12 g, 0.40 mmol), methanesulfonamide (0.10 g, 0.12 mmol), tri-tert-butylphosphonium tetrafluoroborate (12 mg, 0.04 mmol), Herrmann's palladacycle (18 mg, 0.02 mmol) and molybdenehexacarbonyl (105 mg, 0.40 mmol) was stirred in dioxane (2 mL). 1,8-diazabicyclo[5.4.0]undec-7-ene (0.18 mL, 0.12 mmol) was added in one portion, then the vial was sealed and heated in a microwave for 15 minutes at 140° C. The solvent was evaporated in vacuo. The residue was extracted with dichloromethane (30 mL) and washed with water (10 mL). The organic layer was dried over magnesium sulfate, filtered and evaporated. The resulting solid was purified on a 10 g silica cartridge (eluent:dichloromethane, followed by 3% methanol in dichloromethane) to afford the title compound (51 mg, 37%) as a beige solid. This was purified further by preparative HPLC.

LCMS Rt=2.75 minutes MS m/z 341 [MH]+

EXAMPLE 64

4-[(5-Chloropyridin-2-yl)methoxy]-2,5-difluoro-N-(methylsulfonyl)benzamide diethylamine salt

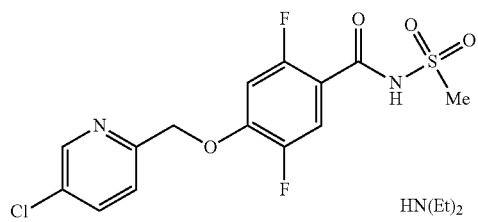 [SMILES: CS(=O)(=O)NC(=O)c1cc(F)c(OCc2ccc(Cl)cn2)cc1F ; "HN(Et)2"]

To a solution of (5-chloropyridin-2-yl)methanol (15 mg, 0.105 mmol), in dichloromethane (5 mL) and triethylamine (0.02 mL, 0.157 mmol) was added methanesulfonyl chloride (0.01 mL, 0.115 mmol). The reaction was stirred at room temperature for 2 hours. The solvent was removed in vacuo to afford a residue, which was taken up in DMSO (5 mL). Potassium carbonate (43 mg, 0.315 mmol) was added, followed by 2,5-difluoro-4-hydroxy-N-(methylsulfonyl)benzamide (Preparation 110, 29 mg, 0.115 mmol) and the reaction was heated to 50° C. overnight. The reaction mixture was cooled to room temperature, diluted with water (10 mL) and extracted with ethyl acetate (3×10 mL). The combined organic layers were dried over sodium sulphate, filtered and concentrated in vacuo. The resulting residue was purified by preparative HPLC to afford the title compound.

LCMS (acidic, 4.5 min) Rt=2.88 minutes MS m/z 377 [MH]+

The skilled person will appreciate that where in the above Examples the compound of formula (I) was prepared in the form of a salt, the same may be converted into the corresponding free base or free acid under conventional conditions (or, in the case of a salt arising from purification by the Auto-HPLC conditions described above in the preamble to the Examples, by use of appropriate alternative preparative HPLC conditions).

In particular, the following compounds of formula (I) may be prepared:

4-{[(5-Chloro-6-isobutoxypyridin-3-yl)oxy]methyl}-2,5-difluoro-N-(methylsulfonyl)benzamide;
4-((5-Chloro-6-isopropoxypyridin-3-yl)methoxy)-2,5-difluoro-N-(methylsulfonyl)benzamide;
4-{[(5-Chloro-6-isobutoxypyridin-3-yl)oxy]methyl}-N-(methylsulfonyl)benzamide;
4-((5-Chloro-6-isobutoxypyridin-3-yloxy)methyl)-3-methoxy-N-(methylsulfonyl)benzamide;
N-(methylsulfonyl)-4-{[6-(trifluoromethyl)pyridin-3-yl]methoxy}benzamide;
5-Chloro-4-{[(5,6-dicyclopropylpyridin-3-yl)oxy]methyl}-2-fluoro-N-(methylsulfonyl)benzamide;
5-Chloro-4-({[6-cyclopropyl-5-(difluoromethoxy)pyridin-3-yl]oxy}methyl)-2-fluoro-N-(methylsulfonyl)benzamide; and
4-[(5-Chloropyridin-2-yl)methoxy]-2,5-difluoro-N-(methylsulfonyl)benzamide.

Preparation 1

5-Chloro-6-isobutoxypyridin-3-ol

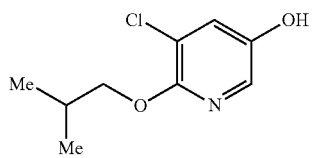 [SMILES: CC(C)COc1ncc(O)cc1Cl]

To a suspension of 5-chloro-6-isobutoxypyridin-3-ylboronic acid (3.02 g, 13.1 mmol) in acetic acid/water (1:1 20 mL) cooled to 0° C. was slowly added peracetic acid (3.9 mL, 20.0 mmol) and the reaction mixture was maintained at 0° C. for 1.5 hours and then at room temperature for 1 hour. Additional peracetic acid (3.9 mL, 20.0 mmol) was added and the reaction stirred at room temperature for 40 minutes after which time the suspension dissolved. The reaction mixture was quenched with sodium thiosulphate solution (15 mL) and stirred for 5 minutes. The mixture was extracted with ethyl acetate (2×30 mL) and the combined organic extracts washed with brine (30 mL), dried over magnesium sulphate and filtered. The solvent was removed under reduced pressure to give a yellow oil (3.66 g). Purification by flash column chromatography (Biotage™ 50 g silica cartridge) eluting with a gradient of dichloromethane/methanol (100% to 90% to 80%) gave the title compound (1.94 g, 73%) as a white solid.

¹H NMR (400 MHz, CDCl₃): δ 1.02 (d, 6H), 2.11 (m, 1H), 4.05 (d, 2H), 6.03 (br s, 1H), 7.31 (d, 1H), 7.65 (d, 1H)

LCMS Rt=2.51 minutes MS m/z 200 [M-H]−

Preparation 2

Methyl 2,5-difluoro-4-methylbenzoate

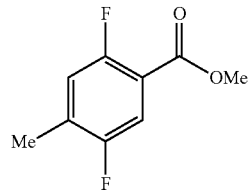 [SMILES: COC(=O)c1cc(F)c(C)cc1F]

Methanol (10 mL) was added to 2,5-difluoro-4-methylbenzoyl chloride (500 mg, 2.6 mmol) and the solution evaporated to give an oil. The oil was dissolved in ethyl acetate and extracted with saturated aqueous sodium carbonate solution (20 mL) and brine (2×20 mL). The organic layer was separated, dried over sodium sulphate, filtered and concentrated in vacuo to afford the title compound as clear colourless solid (300 mg, 62%).

¹H NMR (400 MHz, CDCl₃): δ 2.32 (s, 3H), 3.93 (s, 3H), 6.96-7.00 (m, 1H), 7.55-7.59 (m, 1H).

LCMS Rt=1.32 minutes MS m/z 187 [MH]+.

Preparation 3

Methyl 4-(bromomethyl)-2,5-difluorobenzoate

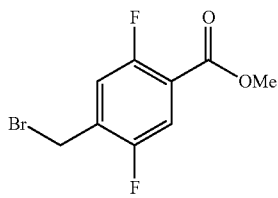 [SMILES: COC(=O)c1cc(F)c(CBr)cc1F]

A solution of methyl 2,5-difluoro-4-methylbenzoate (Preparation 2, 500 mg, 2.69 mmol), N-bromosuccinimide (526 mg, 2.96 mmol) and dibenzoyl peroxide (20 mg, 0.08 mmol) dissolved in carbon tetrachloride (10 mL) was heated to reflux at 85° C. for 18 hours. The mixture was cooled to room temperature, dichloromethane (20 mL) added and the mixture poured into a separating funnel. The resulting organic layer was separated and washed successively with water (20 mL) and aqueous sodium thiosulphate solution (20 mL). The organic layer was dried over magnesium sulphate and filtered. The solvent was removed under reduced pressure to give an oil (748 mg). The crude product was purified by flash column chromatography (Biotage™ 50 g silica cartridge) eluting with 10% ethyl acetate in heptane to give the title compound (479 mg, 67%) as an oil.

¹H NMR (400 MHz, CDCl₃): δ 3.93 (s, 3H), 4.45 (s, 2H), 7.20 (dd, 1H), 7.63 (dd, 1H)

LCMS Rt=2.66 minutes MS m/z 265, 267 [MH]+

Preparation 4

Methyl 4-{[(5-chloro-6-isobutoxypyridin-3-yl)oxy]methyl}-2,5-difluorobenzoate

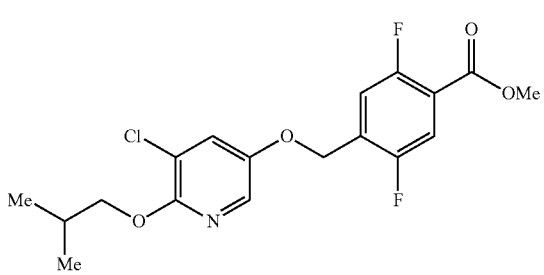 [SMILES: COC(=O)c1cc(F)c(COc2cnc(OCC(C)C)c(Cl)c2)cc1F]

To 5-chloro-6-isobutoxy-pyridin-3-ol (Preparation 1, 364 mg, 1.8 mmol) in DMSO (15 mL) was added methyl 4-(bromomethyl)-2,5-difluorobenzoate (Preparation 3, 479 mg, 1.8 mmol) followed by potassium carbonate (500 mg, 3.6 mmol) and the resulting mixture stirred at room temperature for 18 hours under nitrogen. The mixture was poured onto water (20 mL) and extracted with ethyl acetate (3×40 mL). The combined extracts were washed with water (20 mL), dried over magnesium sulphate, filtered and the solvent removed under reduced pressure to give the title compound (623 mg, 89%) as a light brown oil.

LCMS Rt=4.11 minutes. MS m/z 386 [MH]+

Preparation 5

4-{[(5-Chloro-6-isobutoxypyridin-3-yl)oxy]methyl}-2,5-difluorobenzoic acid

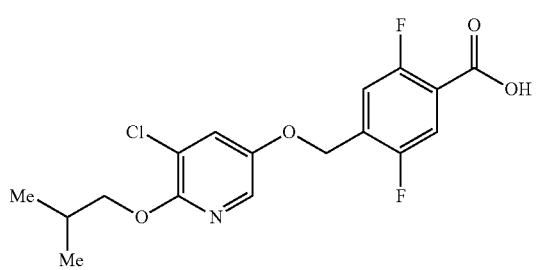 [SMILES: CC(C)COc1ncc(OCc2cc(F)c(C(=O)O)cc2F)cc1Cl]

To a solution of methyl 4-((5-chloro-6-isobutoxypyridin-3-yloxy)methyl)-2,5-difluorobenzoate (Preparation 4, 623 mg, 1.6 mmol) in THF (10 mL) was added lithium hydroxide (1.8 mL of a 1 M solution in water) and the mixture stirred at room temperature under nitrogen for 18 hours. The solvent was evaporated in vacuo to give the title compound (352 mg, 59%) as a pale yellow solid and was used directly in the next step.

LCMS Rt=3.97 minutes. MS m/z 372 [M-H]−

Preparation 6

3-Chloro-2-isopropoxypyridine

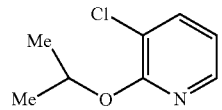

To a 3-necked flask equipped with a dropping funnel, thermometer and a condenser was added sodium hydride (64.10 g, 60% w/w dispersion in oil, 1.07 mol) followed by THF (1.65 L). The suspension was cooled to 5° C. and iso-propanol (128 mL, 1.07 mol) was added dropwise over 50 minutes. Upon complete addition the ice bath was removed and the mixture was brought to room temperature and left to stir for 1 hour. Then 2,3-dichloropyridine (154.6 g, 1.11 mol) was added and the reaction mixture brought to a gentle reflux and left to stir for 18 hours. The reaction mixture was cooled to 5-10° C. and was carefully quenched with brine:water mixture (50:50; 100 mL) followed by water (300 mL). The aqueous layer was extracted with ethyl acetate (3×600 mL), the organic layers combined and washed with brine, dried over magnesium sulphate, filtered and evaporated in vacuo to give the title compound as a dark red oil (164 g, 89%).

$^1$H NMR (400 MHz, CDCl$_3$): δ 1.40 (6H, d), 5.36 (1H, m), 6.80 (1H, m), 7.6 (1H, m), 8.05 (1H, m).

LCMS Rt=3.09 minutes MS m/z 130 [M−iPr]+

Preparation 7

3-chloro-2-isopropoxy-5-(4,4,5,5-tetramethyl-1,3,2-dioxaborolan-2-yl)pyridine

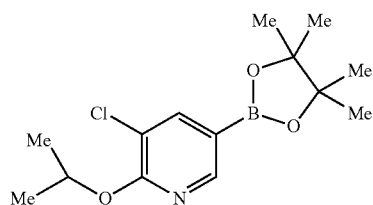 [SMILES: CC(C)Oc1ncc(B2OC(C)(C)C(C)(C)O2)cc1Cl]

A round bottom flask was charged with 3-chloro-2-isopropoxypyridine (Preparation 6, 154 g, 898 mmol), bispinacolatodiboron (274 g, 1.08 mol) and 4,4-di-tert-butyl-2,2-dipyridyl (2.45 g, 8.97 mmol) in heptane (1.55 L). The reaction mixture was cycled between vacuum and nitrogen 6 times over 15 minutes. Di-mu-methanolatodiiridium(Ir—Ir)-cycloocta-1,5-diene (1:2) (2.45 g, 4.49 mmol) was added and the reaction left to stir for 18 hours under nitrogen. Once all starting materials have been consumed the reaction mixture was cooled to 5° C. and quenched with methanol (70 mL). After complete addition the reaction mixture was evaporated in vacuo and the resulting red viscous oil was used in the next step without further purification.

$^1$H NMR (400 MHz, CDCl$_3$): δ 1.20 (6H, d), 1.32-1.35 (12H, s), 4.40 (1H, m), 7.96 (1H, m), 8.38 (1H, m).

LCMS Rt=4.55 minutes

Preparation 8

5-chloro-6-isopropoxypyridin-3-ol

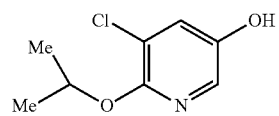 [SMILES: CC(C)Oc1ncc(O)cc1Cl]

To a solution of 3-chloro-2-isopropoxy-5-(4,4,5,5-tetramethyl-1,3,2-dioxaborolan-2-yl)pyridine (Preparation 7, 297.6 g, 897.9 mmol) in acetic acid:water (2.2 L:1.0 L) at 0° C. was added peracetic acid (191 mL, 1.077 mol) and the reaction was allowed to warm gradually to room temperature. After 4 hours the reaction was complete and was quenched with 0.5 M solution of sodium thiosulfate (225 mL). The resulting dark solution was evaporated to dryness and the residue was passed through a plug of silica (flushed with neat heptane follow by a gradient up to 10% ethyl acetate:heptane) to remove base line boronate salts. The filtrate was evaporated in vacuo to give a pale yellow viscous oil before further flash column chromatography was performed (1.5 kg for 80 g of material) using 30% ethylacetate in heptane as eluent) to provide a pale yellow solid which was triturated with heptane, dried under suction to give the title compound as a white solid.

$^1$H NMR (400 MHz, CDCl$_3$): δ 1.38 (6H, d), 4.20 (1H, m), 7.25 (1H, m), 7.70 (1H, m)

LCMS Rt=2.15 minutes MS m/z 186 [M-H]−

Preparation 9

2,5-Difluoro-4-methyl-N-(methylsulfonyl)benzamide

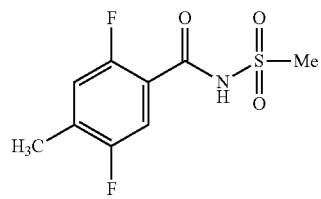 [SMILES: Cc1cc(F)c(C(=O)NS(C)(=O)=O)cc1F]

A mixture of 2-5-difluoro-4-methylbenzoic acid (6.0 g, 34.9 mmol), diisopropylethylamine (13.5 g, 105.0 mmol), propanephosphonic acid cyclic anhydride (50 mL, 50% w/w solution in ethyl acetate, 84.0 mmol) and methyl sulphonamide (6.6 g, 69.7 mmol) in THF (200 mL) was heated under reflux with stirring under N$_2$ for 18 hours. After cooling, the solution was evaporated in vacuo and the residue suspended in water. The mixture was extracted with ethyl acetate (300 mL) and the organic extract then washed with brine (2×80 mL). The organic solution was then dried over sodium sulphate and evaporated in vacuo to give a solid. Trituration with hexane gave the title compound (7.6 g, 87%) as an off white solid after drying.

¹H NMR (400 MHz, DMSO-d6): δ 2.26 (s, 3H), 3.34 (s, 3H), 7.33 (m, 1H), 7.44 (m, 1H).
LCMS Rt=1.24 minutes. MS m/z 248 [M-H]−

Preparation 10

4-(Bromomethyl)-2,5-difluoro-N-(methylsulfonyl)benzamide

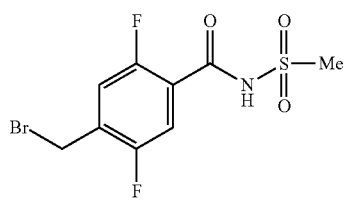 [SMILES: CS(=O)(=O)NC(=O)c1cc(F)c(CBr)cc1F]

A mixture of 2,5-difluoro-4-methyl-N-(methylsulfonyl)benzamide (Preparation 9, 5.07 g, 20.3 mmol), N-bromosuccinimide (freshly recrystallised and dried, 4.7 g, 26.4 mmol) and azobisisobutyronitrile (0.05 g, 0.30 mmol) in 1,2-dichloroethane (100 mL) was heated at reflux under nitrogen whilst being irradiated with light from a lamp. After 2 hours, additional azobisisobutyronitrile (0.05 g, 0.30 mmol) was added and the reaction heated under reflux for a further 2 hours. The reaction mixture was cooled to room temperature and evaporated in vacuo. The residue was partitioned between brine (200 mL) and ethyl acetate (2×150 mL). The combined extracts were dried over magnesium sulphate and evaporated in vacuo to give a pale yellow oil which solidified on standing (7.88 g). Purification by flash column chromatography using the ISCO™ system (120 g cartridge), loading in dichloromethane (20 mL) with an eluant of heptane to 20% ethylacetate/heptane to 30% ethylacetate/heptane gave the title compound (3.71 g, 56%) as a white solid.
¹H NMR (400 MHz, DMSO-d6): δ 3.34 (s, 3H), 4.69 (s, 2H), 7.58 (m, 2H).
LCMS Rt=1.37 minutes MS m/z 328 [M-H]−

Preparation 11

Methyl 4-{[(5-chloro-6-isobutoxypyridin-3-yl)oxy]methyl}benzoate

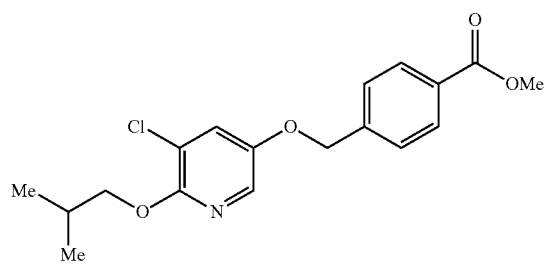 [SMILES: COC(=O)c1ccc(COc2cnc(OCC(C)C)c(Cl)c2)cc1]

To a solution of methyl 4-(bromomethyl)benzoate (250 mg, 1.09 mmol) in acetone (20 mL) were added potassium carbonate (302 mg, 2.18 mmol) and 5-chloro-6-isobutoxypyridin-3-ol (Preparation 1, 220 mg, 1.09 mmol) and the reaction heated at reflux overnight. The reaction was allowed to cool to room temperature, the solvent removed under reduced pressure and the resulting yellow solid dissolved in ethyl acetate (30 mL). The solution was transferred to a separating funnel containing water (50 mL), the organic layer separated and the aqueous extracted with ethyl acetate (2×30 mL). The combined organic extracts were washed with sodium hydroxide (1.0 M aqueous solution, 30 mL), then brine (50 mL), dried over sodium sulphate and filtered to give the title compound as pale yellow solid (369 mg, 97%).
¹H NMR (400 MHz, CDCl₃): δ 1.03 (d, 6H), 2.05-2.17 (m, 1H), 3.93 (s, 3H), 4.07 (d, 2H), 5.10 (s, 2H), 7.37 (d, 1H), 7.48 (d, 2H), 7.75 (d, 1H), 8.07 (d, 2H).
LCMS Rt=4.00 minutes MS m/z 350 [MH]+

Preparation 12

4-{[(5-Chloro-6-isobutoxypyridin-3-yl)oxy]methyl}benzoic acid lithium salt

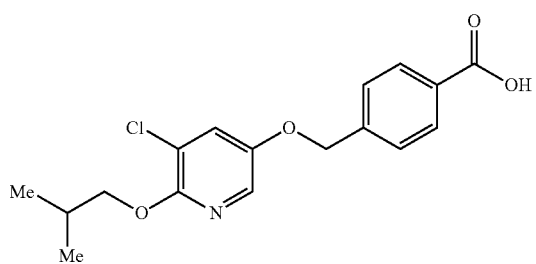 [SMILES: CC(C)COc1ncc(OCc2ccc(C(=O)O)cc2)cc1Cl]

To a suspension of methyl 4-{(5-chloro-6-isobutoxypyridin-3-yloxy)methyl)}benzoate (Preparation 11, 369 mg, 1.06 mmol) in methanol (30 mL) was added aqueous lithium hydroxide (1.0 M, 1.16 mL, 1.16 mmol) and the reaction stirred at 60° C. for 16 hours. After this time the reaction showed remaining starting material. Lithium hydroxide (1.0 M aqueous solution, 0.21 mL, 0.21 mmol) was added and the reaction stirred at reflux for an additional 5.5 hours. The reaction was allowed to cool to room temperature and the solvent was removed under reduced pressure to give the title compound as a pale yellow solid (362 mg, 94%).
¹H NMR (400 MHz, DMSO-d6): δ 0.96 (d, 6H), 2.01 (m, 1H), 4.03 (d, 2H), 5.11 (s, 2H), 7.31 (d, 2H), 7.85 (m, 1H), 7.79-7.91 (m, 3H).
LCMS Rt=3.58 minutes MS m/z 334 [M-H]−

Preparation 13 tert-Butyl 4-((5,6-dichloropyridin-3-yl)methoxy)-2,5-difluorobenzoate

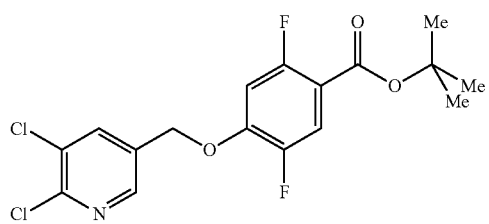 [SMILES: CC(C)(C)OC(=O)c1cc(F)c(OCc2cnc(Cl)c(Cl)c2)cc1F]

To a solution of (5,6-dichloropyridin-3-yl)methanol (275 mg, 1.55 mmol) in DMSO (5 mL) were added tert-butyl 2,4,5-trifluorobenzoate (Preparation 97, 300 mg, 1.30 mmol), and potassium carbonate (535 mg, 3.88 mmol) and the mixture stirred for 18 hours at room temperature under a nitrogen atmosphere. Water (10 mL) was added and the mixture extracted with EtOAc (3×20 mL). The combined organics were washed with water (20 mL) and concentrated in vacuo to yield the title compound (490 mg, 96%).

$^1$H NMR (400 MHz, CDCl$_3$): δ 1.50 (s, 9H), 5.30 (s, 2H), 7.35 (m, 1H), 7.60 (m, 1H), 8.25 (s, 1H), 8.50 (s, 1H).

LCMS Rt=3.95 minutes MS m/z Molecular ion not observed.

Preparation 14

4-((5,6-Dichloropyridin-3-yl)methoxy)-2,5-difluorobenzoic acid

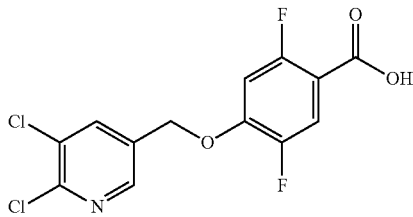 [SMILES: O=C(O)c1cc(F)c(OCc2cnc(Cl)c(Cl)c2)cc1F]

To a solution of tert-butyl 4-((5,6-dichloropyridin-3-yl) methoxy)-2,5-difluorobenzoate (Preparation 13, 490 mg, 1.27 mmol) in DCM (5 mL) was added TFA (5 mL). After 30 minutes the reaction mixture was concentrated in vacuo and the resulting residue was purified by reverse phase chromatography eluting with H$_2$O/MeCN/HCOOH (95/5/0.1 to 5/95/0.1, Biotage™ 40 g C18-silica gel) to yield the title compound (210 mg, 50%).

$^1$H NMR (400 MHz, CDCl$_3$): δ 5.30 (s, 2H), 7.40 (m, 1H), 7.65 (m, 1H), 8.25 (s, 1H), 8.50 (s, 1H)

LCMS Rt=2.78 minutes MS m/z 332 [M-H]$^{31}$

Preparation 15

4-((5-Chloro-6-isopropoxypyridin-3-yl)methoxy)-2,5-difluorobenzoic acid

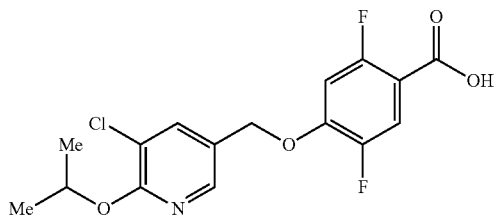 [SMILES: CC(C)Oc1ncc(COc2cc(F)c(C(=O)O)cc2F)cc1Cl]

To a solution of 4-((5,6-dichloropyridin-3-yl)methoxy)-2, 5-difluorobenzoic acid (Preparation 14, 210 mg, 0.67 mmol) in THF (5 mL) was added an oil dispersion of NaH (60%, 157 mg, 3.93 mmol) followed by iso-propanol (5 mL) and the reaction mixture was warmed to 80° C. and stirred for 18 hours under a nitrogen atmosphere. Aqueous hydrogen chloride solution (1 M, 20 mL) was added and the mixture extracted with EtOAc (3×30 mL). The combined organics were dried over magnesium sulfate and the solvent was removed in vacuo. The resulting crude was purified by reverse phase chromatography eluting with H$_2$O/MeCN/HCOOH (95/5/0.1 to 5/95/0.1, Biotage™ 40 g C18-silica gel) to yield the title compound (105 mg, 46%).

$^1$H NMR (400 MHz, CDCl$_3$): δ 1.35 (m, 6H), 5.20 (s, 2H), 5.30 (m, 1H), 7.40 (m, 1H), 7.60 (m, 1H), 8.00 (s, 1H), 8.25 (s, 1H).

LCMS Rt=3.77 minutes MS m/z 356 [M-H]$^{31}$

Preparation 16

4-{[(5-Chloro-6-methoxypyridin-3-yl)oxy] methyl}benzoic acid

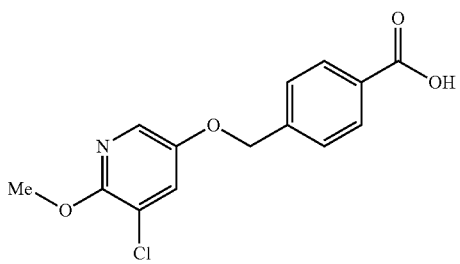 [SMILES: COc1ncc(OCc2ccc(C(=O)O)cc2)cc1Cl]

To a solution of 4-(bromomethyl)benzoic acid (270 mg, 1.25 mmol) in acetone (15 mL) were added potassium carbonate (520 mg, 3.76 mmol) and 5-chloro-6-methoxypyridin-3-ol (Preparation 56, 200 mg, 1.25 mmol). The reaction mixture was heated at reflux under nitrogen for 18 hours. The reaction mixture was cooled to room temperature and partitioned between EtOAc (20 mL) and water (20 mL). The aqueous phase was further extracted with EtOAc (20 mL). The combined organics were dried over sodium sulfate and concentrated in vacuo to yield the title compound as a pink solid (400 mg), which was used in the next step without further purification.

LCMS Rt=1.47 minutes MS m/z 293 [MH]$^+$

Preparation 17

4-{[(5-chloropyridin-3-yl)oxy]methyl}benzoic acid

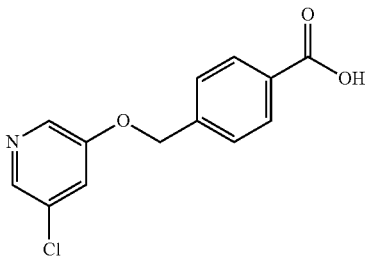 [SMILES: O=C(O)c1ccc(COc2cncc(Cl)c2)cc1]

To a suspension of 5-chloro-3-hydroxypyridine (0.6 g, 4.6 mmol) and potassium carbonate (1.27 g, 9.2 mmol) in acetone (10 mL) was added 4-carboxybenzylbromide (1.0 g, 4.6 mmol). The reaction was heated at reflux for 18 hours. After cooling, the reaction mixture was partitioned between EtOAc (80 mL) and saturated aqueous ammonium chloride solution (140 mL). The organic layer was dried over magnesium sulfate and evaporated in vacuo to afford the title compound (0.65 g, 53%), which was used in the next step without further purification.

¹H NMR (400 MHz, CDCl₃): δ 5.2 (s, 2H), 7.65 (m, 2H), 7.90 (m, 3H), 8.05 (s, 1H), 8.20 (s, 1H).
LCMS Rt=2.15 minutes MS m/z 264 [MH]⁺

Preparation 18

Ethyl 2,5-difluoro-4-methylbenzoate

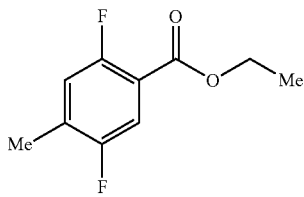 [SMILES: CCOC(=O)c1cc(F)c(C)cc1F]

To a solution of 2,5-difluoro-4-methylbenzoic acid (5 g, 2.904 mmol) in ethanol (100 mL) was added concentrated sulfuric acid (1 mL). The reaction mixture was stirred at reflux for 18 hours. LCMS showed complete consumption of starting material, so the solvents were removed in vacuo and the resulting residue redissolved in EtOAc (50 mL), and washed with saturated aqueous sodium bicarbonate. The organic layer was separated, and the aqueous layer extracted with EtOAc (2×50 mL). The combined organics were dried over sodium sulfate and evaporated to yield the title compound as a pale yellow oil (5.502 g, 95%).
¹H NMR (CDCl₃, 400 MHz): δ 1.38 (t, 3H), 2.30 (d, 3H), 4.37 (q, 2H), 6.95 (dd, 1H), 7.55 (dd, 1H).
LCMS Rt=3.06 minutes. MS m/z molecular ion not observed.

Preparation 19

Ethyl 4-(bromomethyl)-2,5-difluorobenzoate

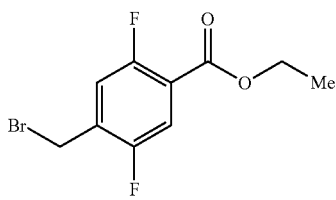 [SMILES: CCOC(=O)c1cc(F)c(CBr)cc1F]

To a solution of ethyl 2,5-difluoro-4-methylbenzoate (Preparation 18, 4.674 g, 23.35 mmol) in 1,2-dichloroethane (70 mL) were added N-bromosuccinimide (4.57 g, 25.68 mmol) and benzoyl peroxide (56 mg, 0.23 mmol) and the mixture was heated to 70° C. for 2 days. The reaction mixture was allowed to cool, quenched with saturated aqueous sodium thiosulfate (20 mL) and diluted with water (50 mL). The organic layer was separated and the aqueous layer extracted with DCM (2×80 mL). The combined organics were washed with saturated aqueous sodium hydrogen carbonate, followed by brine, then filtered through a phase separator and concentrated in vacuo. The resulting yellow oil was redissolved in EtOAc (70 mL), and N,N-diisopropylethylamine (4.04 mL, 23.35 mmol) was added. The mixture was cooled to 0° C., and diethyl phosphate (2.29 mL, 23.35 mmol) was added. After stirring at 0° C. for 90 minutes, LCMS indicated complete conversion of the dibromomethyl impurity to the desired mono-bromomethyl product. The reaction was quenched at 0° C. with water (70 mL), followed by aqueous hydrochloric acid (2N, 10 mL). The organic layer was separated, washed with brine (100 mL), dried over sodium sulfate and concentrated in vacuo to yield a yellow residue. The residue was purified by silica gel chromatography eluting with 0 to 3% EtOAc in heptane to afford the title compound as a clear oil (5.78 g, 89%):
¹H NMR (CDCl₃, 400 MHz): δ 1.39 (t, 3H), 4.39 (q, 2H), 4.44 (d, 2H), 7.20 (m, 1H), 7.60 (m, 1H).
LCMS Rt=3.08 minutes. MS m/z molecular ion not observed.

Preparation 20

Methyl 5-chloro-2-fluoro-4-methyl benzoate

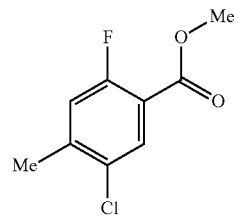 [SMILES: COC(=O)c1cc(Cl)c(C)cc1F]

To a solution of 1-bromo-5-chloro-2-fluoro-4-methylbenzene (10 g, 44.7 mmol) in 200 mL of methanol were added 1,1'-binaphthalene-2,2'-diylbis(diphenylphosphine)-dichloropalladium (1:1) (358 mg, 0.447 mmol) and N,N-diethylethanamine (8.11 mL, 58.2 mmol). The resulting reaction mixture was placed in a bomb, pressurised to 80 psi of carbon monoxide and heated at 80° C. for 18 hours. The reaction mixture was concentrated in vacuo to yield a semi-solid which was dissolved in EtOAc (300 mL) and washed with water (200 mL). The organic layer was separated, dried over magnesium sulfate, filtered and evaporated in vacuo. The resulting crude product was purified by silica gel chromatography eluting with 0 to 20% EtOAc in heptane to afford the title compound as a white crystalline solid (8.47 g, 93%).
¹H NMR (400 MHz, CDCl₃): δ 2.40 (s, 3H), 3.92 (s, 3H), 7.03 (d, 1H), 7.91 (d, 1H).
LCMS Rt=1.64 minutes MS m/z Molecular ion not observed.

Preparation 21

5-Chloro-2-fluoro-4-methylbenzoic acid

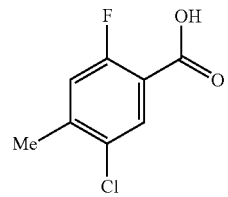 [SMILES: Cc1cc(F)c(C(=O)O)cc1Cl]

To a stirred solution of methyl 5-chloro-2-fluoro-4-methylbenzoate (Preparation 20, 340 mg, 1.68 mmol) in 12 mL of dioxane/water (5:1) was added aqueous sodium hydroxide (5 M, 1.63 mL, 8.39 mmol). The reaction mixture was stirred at room temperature for 18 hours and then evaporated in vacuo. The resulting residue was suspended in water and extracted with diethyl ether (3×20 mL). The aqueous layer was cooled in an ice bath, acidified with aqueous hydrochloric acid (6 M) and extracted with EtOAc (30 mL). The organic layer was separated, washed with brine (2×20 mL), dried over sodium sulfate, filtered and evaporated in vacuo to yield the title compound as a white solid (266 mg, 84%).

$^1$HNMR (400 MHz, d$_6$-DMSO): δ 2.36 (s, 3H), 7.38 (m, 1H), 7.80 (d, 1H).

LCMS Rt=1.39 minutes MS m/z 187 [M-H]$^-$

Preparation 22

5-Chloro-2-fluoro-4-methyl-N-(methylsulfonyl)benzamide

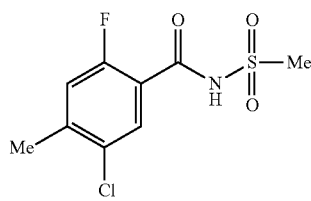 [SMILES: Cc1cc(F)c(C(=O)NS(C)(=O)=O)cc1Cl]

To a solution of 5-chloro-2-fluoro-4-methylbenzoic acid (Preparation 21, 200 g, 1.06 mol) in DCM (1.4 L) were added methanesulphonamide (152 g, 1.6 mol), 4-(dimethylamino)pyridine (183 g 1.6 mol) and N-(3-dimethylaminopropyl)-N'-ethylcarbodiimide hydrochloride (306 g, 1.6 mol). An exotherm of 30° C. was observed in the first 30 minutes, then the mixture was stirred at room temperature for 18 hours under a nitrogen atmosphere. The reaction mixture was washed with aqueous hydrochloric acid (4 M, 0.8 L). The organic layer was separated, washed with water (500 mL) and dried over sodium sulfate to yield a tan solid, which was recrystallised from hot EtOAc (0.9 L) by addition of n-heptane (100 mL) and cooling to afford the title compound (118 g, 45%).

$^1$H NMR (400 MHz, CDCl$_3$): δ 2.42 (s, 3H), 3.42 (s, 3H), 7.10 (d, 1H), 8.05 (d, 1H), 8.78 (br, 1H).

Preparation 23

4-(Bromomethyl)-5-chloro-2-fluoro-N-(methylsulfonyl)benzamide

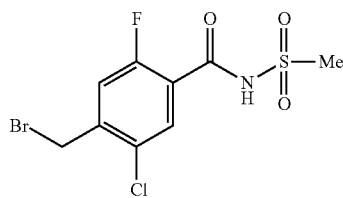

To a suspension of 5-chloro-2-fluoro-4-methyl-N-(methylsulfonyl)benzamide (Preparation 22, 118 g, 0.45 mol) in 1,2-dichloroethane (1.25 L) were added N-bromosuccinimide (91 g, 0.51 mol) and benzoyl peroxide (5 g, 20 mmol) and the mixture was heated at reflux for 18 hours. N-bromosuccinimide (30 g, 0.17 mol) was added and the mixture was heated for further 24 hours. N-bromosuccinimide (20 g, 0.11 mol) was then added and the mixture heated for another 3 hours, then cooled and washed with water (1 L) and aqueous sodium thiosulphate (0.5 M, 200 mL). The organic layer was washed with water (500 mL), dried over sodium sulfate and evaporated. The resulting crude tan solid was dissolved in EtOAc (1 L), diisopropylethylamine (130 mL, 0.75 mol) and diethyl phosphite (27.6 g, 0.2 mol) were added and the mixture was stirred for 5 hours under a nitrogen atmosphere. The reaction mixture was then washed with aqueous hydrochloric acid (2 M, 1 L), dried over magnesium sulfate and evaporated to yield a dark solid, which was triturated with diethyl ether (200 mL) to afford the title compound as a tan solid (68 g). The filtrate was purified by silica gel chromatography eluting with 10% EtOAc and 1% acetic acid in DCM, followed by recrystallization with MeCN (130 mL) to afford a second crop of the title compound.

$^1$H NMR (400 MHz, CDCl$_3$): δ 3.41 (s, 3H), 4.54 (s, 2H), 7.38 (d, 1H), 8.14 (d, 1H), 8.78 (br, 1H).

Preparation 24

2-Methoxy-4-methyl-N-(methylsulfonyl)benzamide

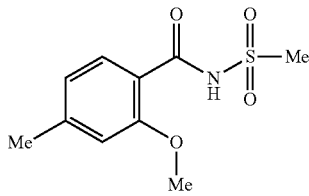 [SMILES: COc1cc(C)ccc1C(=O)NS(C)(=O)=O]

2-Methoxy-4-methyl-benzoic acid (1.0 g. 6 mmol), methanesulphonamide (1.14 g. 12 mmol), 1-(3-dimethylaminopropyl)-3-ethylcarbodiimide hydrochloride (2.31 g. 12 mmol), 4-dimethylaminopyridine (1.47 g. 12 mmol) and DCM (50 mL) were combined and stirred at room temperature under nitrogen for 18 hours. The reaction mixture was concentrated in vacuo and the residue suspended in water and acidified with aqueous potassium hydrogen sulphate (0.5 M). The mixture was extracted with EtOAc (1×30 mL). The organic layer was separated, washed with brine (2×20 mL), dried over sodium sulfate, filtered and evaporated to give a solid, which was triturated with hexane: diethyl ether (4:1) to yield the title compound as a white solid (0.92 g, 63%).

$^1$H NMR (400 MHz, CDCl$_3$): δ 2.43 (s, 3H), 3.41 (s, 3H), 4.03 (s, 3H), 6.83 (s, 1H), 6.95 (d, 1H), 8.08 (d, 1H), 10.18 (br, 1H).

LCMS Rt=1.01 minutes. MS m/z 244 [MH]$^+$

Preparation 25

2-Methoxy-4-(bromomethyl)-N-(methylsulfonyl)benzamide

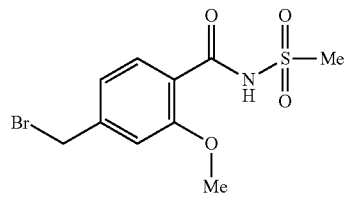 [SMILES: COc1cc(CBr)ccc1C(=O)NS(C)(=O)=O]

2-Methoxy-4-methyl-N-(methylsulfonyl)benzamide (Preparation 24, 500 mg, 2.06 mmol), N-bromosuccinimide (402 mg, 2.36 mmol), azobisisobutyronitrile (10 mg, 0.06 mmol) and carbon tetrachloride (20 mL) were combined and stirred at reflux under nitrogen, whilst being irradiated with light from a lamp for 1 hour. After cooling, the mixture was evaporated, the residue suspended in water (30 mL) and extracted with EtOAc (1×30 mL). The organic layer was separated, washed with saturated brine (2×20 mL), dried over sodium sulfate, filtered and evaporated to give a solid, which was triturated with diethyl ether:hexane (1:4) to yield the title compound as a white solid (375 mg, 57%).

LCMS Rt=1.07 minutes. MS m/z 322 [MH]+

Preparation 26

Methyl 6-[(isobutyrylamino)methyl]nicotinate

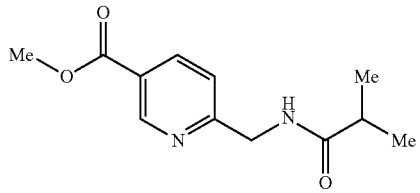 [SMILES: COC(=O)c1ccc(CNC(=O)C(C)C)nc1]

To an ice-cold suspension of methyl 6-(aminomethyl)nicotinate hydrochloride (1.00 g, 4.18 mmol) and N-ethyl-N-isopropylpropan-2-amine (1.89 g, 2.55 mL, 14.6 mmol) in DCM (10 mL) was added dropwise a solution of isobutyryl chloride (535 mg, 526 μL, 5.02 mmol) in DCM (3 mL). The reaction mixture was allowed to warm to room temperature, washed with water (5 mL), 10% aqueous citric acid solution (5 mL), saturated aqueous sodium bicarbonate solution (5 mL), brine (5 mL), dried over magnesium sulfate, filtered and evaporated to yield the title compound as a pale orange solid (0.988 g, 100%):

$^1$H NMR (400 MHz, CDCl$_3$): δ 1.22 (d, 6H), 2.45-2.55 (m, 1H), 3.95 (s, 3H), 4.62 (d, 2H), 6.67-6.68 (br, 1H), 7.32-7.36 (m, 1H), 8.26-8.30 (m, 1H), 9.15 (s, 1H).

LCMS Rt=1.72 minutes MS m/z 237 [MH]+

Preparation 27

Methyl 3-isopropylimidazo[1,5-a]pyridine-6-carboxylate

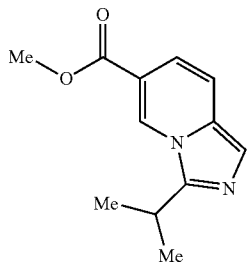 [SMILES: COC(=O)c1ccc2cnc(C(C)C)n2c1]

To a suspension of methyl 6-[(isobutyrylamino)methyl]nicotinate (Preparation 26, 935 mg, 3.96 mmol) in toluene (10 mL) was added phosphoryl chloride (3.03 g, 1.84 mL, 19.8 mmol) and the mixture refluxed under nitrogen for 3 hours. The resulting dark solution was cooled at room temperature and concentrated in vacuo to give an oil. The oil was then dissolved in toluene (10 mL) and concentrated in vacuo again. The resulting residue was partitioned between EtOAc (20 mL) and saturated aqueous sodium hydrogen carbonate solution (2×5 mL). The organic layer was washed with brine (5 mL), dried over magnesium sulfate, filtered and evaporated to yield a dark oil, which was dissolved in methanol (10 mL), treated with charcoal and refluxed for 5 minutes. The mixture was filtered through Celite and the filtrate concentrated in vacuo to yield the title compound as a pale yellow oil (830 mg, 82%), which was used directly in the next stage without further purification.

$^1$H NMR (400 MHz, CDCl$_3$): δ 1.45 (d, 6H), 3.32-3.46 (m, 1H), 3.93 (s, 3H), 7.15 (d, 1H), 7.35-7.43 (m, 2H), 8.58 (s, 1H).

LCMS Rt=1.44 minutes MS m/z 219 [MH]+

Preparation 28

(3-Isopropylimidazo[1,5-a]pyridin-6-yl)methanol

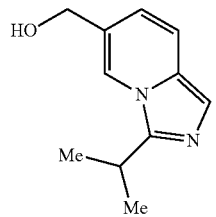 [SMILES: CC(C)c1ncc2ccc(CO)cn12]

To an ice-cold solution of methyl 3-isopropylimidazo[1,5-a]pyridine-6-carboxylate (Preparation 27, 234 mg, 1.07 mmol) in THF (4 mL) was added lithium aluminium hydride solution in THF (2 M, 61 mg, 804 μL, 1.61 mmol). The mixture was allowed to warm to room temperature. After 3 hours the reaction was cooled again in an ice bath and quenched with a saturated solution of sodium sulfate (1 mL). The mixture was stirred for 30 minutes and then filtered through Celite. The filtrate was evaporated to low volume and the aqueous residue extracted with DCM (3×5 mL). The combined organic extracts were washed with brine, dried over magnesium sulfate, filtered and evaporated. The resulting residue was purified by silica gel chromatography eluting with 10 to 100% EtOAc in pentane to yield the title compound as a yellow gum (120 mg, 59%).

$^1$H NMR (400 MHz, CDCl$_3$): δ 1.40 (d, 6H), 3.25-3.35 (m, 1H), 4.63 (s, 2H), 6.63 (d, 1H), 7.32 (s, 1H), 7.38 (d, 1H), 7.78 (s, 1H).

LCMS Rt=0.56 minutes MS m/z 191 [MH]+

Preparation 29

5-Chloro-2,4-difluoro-N-(methylsulfonyl)benzamide

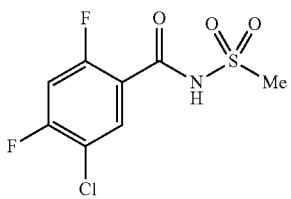

5-Chloro-2,4-dilfluorobenzoic acid (0.291 g, 1.511 mmol), N-Ethyl-N'-(3-dimethylaminopropyl)carbodiimide hydrochloride (0.438 g, 2.285 mmol) and 4-dimethylaminopyridine (0.420 g, 3.438 mmol) were suspended in DCM (5 mL). methanesulphonamide (0.222 g, 2.334 mmol) was added and the mixture was stirred at room temperature for 18 hours. The reaction mixture was diluted with DCM (10 mL) and washed with aqueous hydrochloric acid solution (2 M, 2×15 mL). The organic layer was dried with a phase separating cartridge and concentrated in vacuo to yield the title compound as a white solid (0.388 g).

$^1$H NMR (400 MHz, d$_6$-DMSO): δ 3.38 (s, 3H), 7.65 (t, 1H), 7.95 (t, 1H).

LCMS Rt=1.43 minutes MS m/z 268 [MH]$^-$

Preparation 30

3-Chloro-4-[(5-chloro-6-methoxypyridin-3-yl)methoxy]benzonitrile

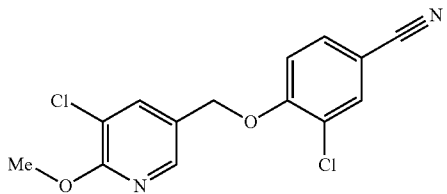 [SMILES: COc1ncc(COc2ccc(C#N)cc2Cl)cc1Cl]

To a solution of 5-chloro-3-hydroxymethyl-6-methoxypyridine (50 mg, 0.29 mmol) in DMF (3 mL) was added sodium hydride dispersion in oil (60%, 13.8 mg, 0.576 mmol) and the reaction stirred at 0° C. for 30 minutes. 3-Chloro-4-fluorobenzonitrile (45 mg, 0.288 mmol) was then added and the reaction stirred, warming to room temperature for 2 hours. The reaction was poured onto water (10 mL) and extracted with EtOAc (10 mL), dried over sodium sulfate and concentrated in vacuo to afford the title compound (89 mg, 72%).

LCMS Rt=1.75 minutes MS m/z 309 [MH]$^+$ $^1$H NMR (d$_6$-DMSO): δ 3.95 (s, 3H), 4.25 (s, 2H), 7.45 (d, 1H), 7.85 (m, 1H), 8.05 (m, 2H), 8.25 (s, 1H).

Preparation 31

3-Chloro-4-[(5-chloro-6-methoxypyridin-3-yl)methoxy]benzamide

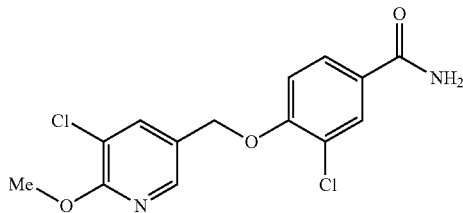 [SMILES: COc1ncc(COc2ccc(C(N)=O)cc2Cl)cc1Cl]

To a suspension of 3-chloro-4-[(5-chloro-6-methoxypyridin-3-yl)methoxy]benzonitrile (Preparation 30, 64 mg, 0.21 mmol) and potassium carbonate (57 mg, 0.414 mmol) in DMSO (5 mL) was added hydrogen peroxide (141 mL, 4.14 mmol) and the reaction stirred at room temperature for 1 hour. The reaction was quenched with water (10 mL) and extracted with EtOAc (10 mL). The organic layer was washed with water (2×10 mL), dried over sodium sulfate and concentrated in vacuo to afford a white solid, which was triturated with EtOAc to yield the title compound (30 mg, 44%).

LCMS Rt=1.53 minutes MS m/z 327 [MH]$^+$ $^1$H NMR (d$_6$-DMSO): δ 3.95 (s, 3H), 5.20 (s, 2H), 7.35 (m, 2H), 7.85 (m, 1H), 7.95 (m, 2H), 8.0 (s, 1H), 8.25 (s, 1H).

Preparation 32

Ethyl 4-((5-chloro-6-methoxypyridin-3-yloxy)methyl)-2,5-difluorobenzoate

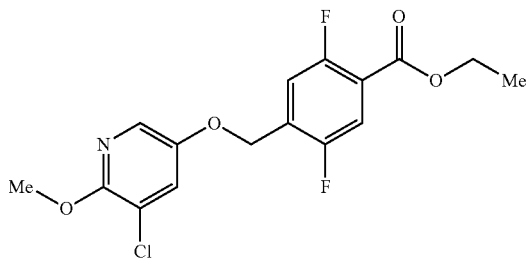 [SMILES: CCOC(=O)c1cc(F)c(COc2cnc(OC)c(Cl)c2)cc1F]

To a solution of 5-chloro-6-methoxypyridin-3-ol (Preparation 56, 98 mg, 0.612 mmol) in acetone (10 mL) were added ethyl 4-(bromomethyl)-2,5-difluorobenzoate (Preparation 19, 171 mg, 0.612 mmol) and potassium carbonate (170 mg, 1.224 mmol). The mixture was stirred for 18 hours at room temperature under a nitrogen atmosphere. The reaction mixture was diluted with water (20 mL), and extracted with DCM (2×30 mL). Combined organic extracts were dried over sodium sulphate, and evaporated to a yellow solid. The solid was purified by silica gel chromatography eluting with DCM/heptanes (3:2) to afford the title compound as a white solid (112 mg, 51%).

1H NMR (400 MHz, CDCl$_3$): δ 1.40 (t, 3H), 4.00 (s, 3H), 4.40 (q, 2H), 5.10 (s, 2H), 7.30-7.35 (m, 1H), 7.40 (s, 1H), 7.60-7.70 (m, 1H), 7.80 (s, 1H).

LCMS Rt=3.95 minutes MS m/z 358 [MH]$^+$

Preparation 33

4-((5-Chloro-6-methoxypyridin-3-yloxy)methyl)-2,5-difluorobenzoic acid

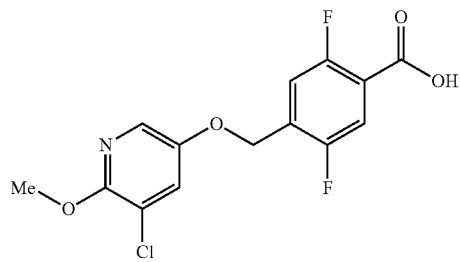 [SMILES: COc1ncc(OCc2cc(F)c(C(=O)O)cc2F)cc1Cl]

A solution of ethyl 4-((5-chloro-6-methoxypyridin-3-yloxy)methyl)-2,5-difluorobenzoate (Preparation 32, 112 mg, 0.313 mmol) in THF (3 mL) was treated with aqueous lithium hydroxide (1 M, 1.6 mL, 1.60 mmol) and stirred at room temperature. After 2½ hours the reaction mixture was acidified with aqueous hydrochloric acid solution (2 N, 15 mL) and extracted with EtOAc (2×25 mL). The combined organic extracts were dried over magnesium sulfate and evaporated to afford the title compound as a white solid (100 mg, 97%).

1H NMR (400 MHz, CDCl₃): δ 3.90 (s, 3H), 5.20 (s, 2H), 7.49 (m, 1H), 7.65 (m, 1H), 7.82 (s, 1H), 7.95 (s, 1H).

LCMS Rt=2.94 minutes MS m/z 330, [MH]⁺

Preparation 34

Methyl 4-((5-chloro-6-isobutoxypyridin-3-yloxy)methyl)-3-methoxybenzoate

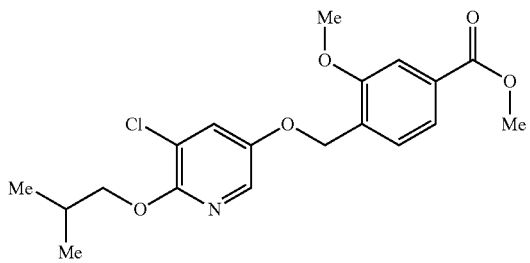 [SMILES: COC(=O)c1ccc(COc2cnc(OCC(C)C)c(Cl)c2)c(OC)c1]

To a solution of methyl 4-(bromomethyl)-3-methoxybenzoate (250 mg, 0.965 mmol) in acetone (20.0 mL) were added potassium carbonate (267 mg, 1.93 mmol) and 5-chloro-6-isobutoxypyridin-3-ol (Preparation 1, 195 mg, 0.965 mmol) and the reaction mixture was heated at reflux for 16 hours, then allowed to cool to room temperature. The solvent was removed in vacuo to yield a yellow solid, which was partitioned between EtOAc (30.0 mL) and water (50.0 mL). The aqueous was further extracted with EtOAc (2×30 mL). The combined organics were washed with sodium hydroxide solution (1 M, 30 mL) then brine (50 mL), dried over sodium sulfate and the solvent was removed in vacuo to yield the title compound as a pale yellow solid.

¹H NMR (400 MHz, CDCl₃): δ 1.03 (d, 6H), 2.06-2.19 (m, 1H), 3.93 (s, 6H), 4.08 (d, 2H), 5.12 (s, 2H), 7.39 (d, 1H), 7.50 (d, 1H), 7.57 (s, 1H), 7.67 (d, 1H), 7.77 (d, 1H).

LCMS Rt=4.10 minutes MS m/z 380 [MH]⁺

Preparation 35

4-((5-Chloro-6-isobutoxypyridin-3-yloxy)methyl)-3-methoxybenzoic acid

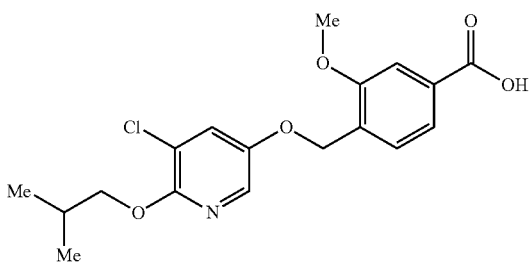 [SMILES: COc1cc(C(=O)O)ccc1COc1cnc(OCC(C)C)c(Cl)c1]

To a suspension of in 4-((5-chloro-6-isobutoxypyridin-3-yloxy)methyl)-3-methoxybenzoate (Preparation 34, 405 mg, 1.07 mmol) in methanol (30.0 mL) was added aqueous lithium hydroxide (1 M, 1.17 mmol, 1.17 mL) and heated at 60° C. for 16 hours. Aqueous lithium hydroxide (1 M, 0.212 mmol, 0.212 mL) was then added and the reaction mixture was heated at 60° C. for 5.5 hours. The reaction mixture was allowed to cool to room temperature and the solvent was removed under reduced pressure to yield the title compound as pale yellow solid:

¹H NMR (400 MHz, CDCl₃): δ 0.96 (d, 6H), 2.02 (m, 1H), 3.81 (s, 3H), 4.03 (d, 2H), 5.06 (s, 2H), 7.27 (d, 1H), 7.46 (m, 1H), 7.55 (d, 1H), 7.70 (d, 1H), 7.86 (d, 1H).

LCMS Rt=3.66 minutes MS m/z 364 [M-H]–

Preparation 36

(3,3-Difluorocyclobutyl)methanol

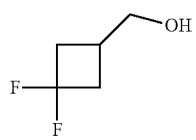

3,3-Difluorocyclobutanecarboxylic acid (5.0 g, 36.7 mmol) was dissolved in THF (50.0 mL) and the reaction was cooled to 0° C. under nitrogen with an ice bath. Then thiodimethane-borane (1:1) (5.23 mL, 61.4 mmol) was added dropwise and the mixture stirred at 0° C. for 4 hours. An aqueous solution of HCl (1 M, 75 mL) and EtOAc (100 mL) were added and the organic layer was then collected and further washed with water (30 mL). The organic layer was then dried over sodium sulfate, filtered, and concentrated in vacuo to afford title compound (3.25 g, 73%).

¹H NMR (400 MHz, d₆-DMSO): δ 2.15-2.40 (m, 3H), 2.40-2.60 (m, 2H), 3.40 (m, 2H), 4.75 (m, 1H).

Preparation 37

3-Chloro-2-[(3,3-difluorocyclobutyl)methoxy]pyridine

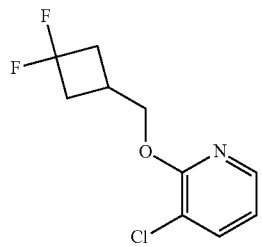 [SMILES: FC1(F)CC(COc2ncccc2Cl)C1]

Sodium hydride (60% dispersion in mineral oil, 1.017 g, 70.6 mmol) was suspended in THF (30.0 mL) and the reaction was cooled to 0° C. under nitrogen with an ice bath. (3,3-Difluorocyclobutyl)methanol (Preparation 36, 2.95 g, 24.2 mmol) in THF (30 mL) was added dropwise to the mixture maintaining the temperature at 0° C. After stirring for 30 minutes, 2,3-dichloropyridine (3.25 g, 22.0 mmol) was added and the suspension was heated to reflux for 16 hours. An aqueous solution of HCl (1 M, 20 mL) was added and the reaction was extracted with EtOAc (2×100 mL). The combined organics were then dried over sodium sulfate, filtered, and concentrated in vacuo. The residue was purified by silica gel chromatography (Biotage®, gradient of 0-50% EtOAc in heptane,) to afford the title compound (4.82 g, 85%).

¹H NMR (400 MHz, d₆-DMSO): δ 2.40-2.50 (m, 2H), 2.60-2.80 (m, 3H), 4.40 (m, 2H), 7.00 (m, 1H), 7.90 (m, 1H), 8.10 (m, 1H).

LCMS Rt=3.11 minutes MS m/z 234 [MH]⁺

Preparation 38

3-Chloro-2-[(3,3-difluorocyclobutyl)methoxy]-5-(4,4,5,5-tetramethyl-1,3,2-dioxaborolan-2-yl)pyridine

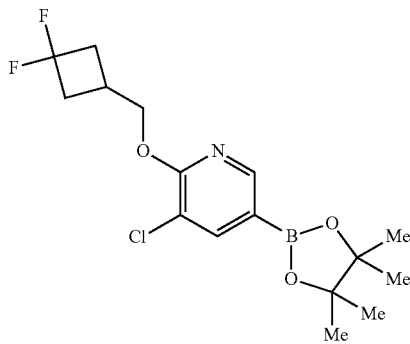 [SMILES: CC1(C)OB(c2cnc(OCC3CC(F)(F)C3)c(Cl)c2)OC1(C)C]

3-Chloro-2-[(3,3-difluorocyclobutyl)methoxy]pyridine (Preparation 37, 4.82 g, 20.6 mmol) was dissolved in 1,4-dioxane (50 mL) and 4,4,4',4',5,5,5',5'-octamethyl-2,2'-bi-1,3,2-dioxaborolane (10.48 g, 41.2 mmol) was added. The reaction mixture was degassed and di-μ-methanolatodiiridium (Ir—Ir)-cycloocta-1,5-diene (1:2) (0.41 g, 0.62 mmol) and 4,4'-di-tert-butyl-2,2'-bipyridine (0.33 g, 1.23 mmol) were also added. The reaction mixture was then stirred at room temperature under nitrogen for 60 hours. Methanol (20 mL) was added and bubbling was observed. When the bubbling stopped, the mixture was concentrated in vacuo and the residue purified by silica gel chromatography (Biotage®, gradient of 0-40% EtOAc in heptane) to afford the title compound (6.4 g, 86%).

¹H NMR (400 MHz, d₆-DMSO): δ 1.30 (s, 12H), 2.50 (m, 2H), 2.60-2.80 (m, 3H), 4.40 (m, 2H), 7.90 (s, 1H), 8.30 (s, 1H).

LCMS Rt=5.24 minutes

Preparation 39

5-Chloro-6-[(3,3-difluorocyclobutyl)methoxy]pyridin-3-ol

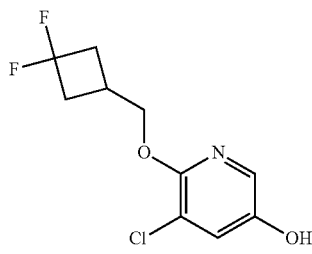 [SMILES: Oc1cnc(OCC2CC(F)(F)C2)c(Cl)c1]

3-Chloro-2-[(3,3-difluorocyclobutyl)methoxy]-5-(4,4,5,5-tetramethyl-1,3,2-dioxaborolan-2-yl)pyridine (Preparation 38, 4.5 g, 12.5 mmol) was suspended in methanol (30 mL). Hydrogen peroxide (1.6 mL, 21.3 mmol) was added and the mixture stirred at room temperature under nitrogen for 16 hours. An aqueous solution of thiosulfite (10%, 10 mL) was added and the mixture was extracted with EtOAc (2×200 mL). The combined organics were dried over sodium sulfate, filtered, and concentrated in vacuo. The residue was purified by silica gel chromatography (Biotage®, gradient of 0-50% EtOAc in heptane) to afford the title compound (2.53 g, 81%).

¹H NMR (400 MHz, d₆-DMSO): δ 2.50 (m, 2H), 2.60-2.80 (m, 3H), 4.25 (m, 2H), 7.35 (s, 1H), 7.60 (s, 1H), 9.75 (s, 1H).

LCMS Rt=2.50 minutes MS m/z 248 [M-H]⁻

Preparation 40

3-Chloro-2-cyclopropylpyridine

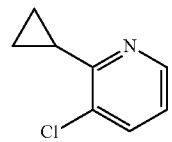

3-Chloro-2-bromopyridine (5.0 g, 26 mmol) and potassium phosphate tribasic (19.3 g, 90.9 mmol) were suspended in toluene (40.0 mL) and water (2.0 mL). The mixture was sonicated for 10 minutes, then cyclopropylboronic acid (1.12 g, 13.0 mmol), palladium diacetate (0.093 g, 0.414 mmol) and tricyclohexylphosphine (0.243 g, 0.867 mmol) were added to the reaction mixture, which was heated into a pre heated DrySyn® at 100° C., under a nitrogen atmosphere for 2 hours. Then cyclopropylboronic acid (1.12 g, 13.0 mmol), palladium diacetate (0.093 g, 0.414 mmol) and tricyclohexylphosphine (0.243 g, 0.867 mmol) were added to the reaction mixture and the mixture was stirred for 2 hours. Then cyclopropylboronic acid (1.12 g, 13.0 mmol), palladium diacetate (0.093 g, 0.414 mmol) and tricyclohexylphosphine (0.243 g, 0.867 mmol) were added to the reaction mixture and the mixture was stirred for 2 hours more. The reaction mixture was stirred at room temperature for 16 hours, diluted with EtOAc (40.0 mL) and water (40.0 mL) and filtered on a pad of Arbocel® under a stream of nitrogen. The organic layer was separated and washed with aqueous citric acid (10%, 3×25.0 mL), followed by aqueous hydrochloric acid (1 M, 3×20.0 mL). The organic layer was discarded and the aqueous layer basified again with careful addition of a saturated aqueous solution of sodium hydrogen carbonate (100.0 mL). The product was extracted with TBME (3×20.0 mL). The combined organics were washed once more with aqueous citric acid (10%, 25.0 mL). The organic layer was then dried over sodium sulfate, filtered, and concentrated in vacuo to yield the title compound as a pale brown oil (2.45 g, 16.02 mmol, 62%).

¹H NMR (400 MHz, d₆-DMSO): δ 0.94-1.01 (m, 4H), 2.40-2.48 (m, 1H), 7.13-7.16 (m, 1H), 7.78-7.81 (m, 1H), 8.33-8.34 (m, 1H).

LCMS Rt=2.27 minutes MS m/z 154 [MH]⁺

Preparation 41

3-Chloro-2-cyclopropyl-5-(4,4,5,5-tetramethyl-1,3,2-dioxaborolan-2-yl)pyridine

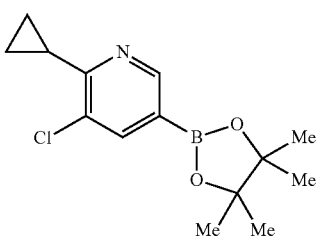 [SMILES: CC1(C)OB(c2cnc(C3CC3)c(Cl)c2)OC1(C)C]

A round bottom flask was charged with 3-chloro-2-cyclopropylpyridine (Preparation 40, 0.475 g, 3.092 mmol), bis(pinacolato)diboron (0.980 g, 3.859 mmol) and 4,4-di-tert-butyl-2,2-dipyridyl (0.025 g, 0.093 mmol) in hexane (10 mL). The reaction mixture was cycled between vacuum and nitrogen 6 times over 15 minutes. Di-µ-methanolatodiiridium(Ir—Ir)-cycloocta-1,5-diene (1:2) (0.063 g, 0.093 mmol) was then added and the reaction stirred for 18 hours under nitrogen atmosphere at room temperature. The reaction mixture was evaporated to dryness to afford the title compound as a red viscous oil, which was used in the next step without further purification.

Preparation 42

5-Chloro-6-cyclopropylpyridin-3-ol

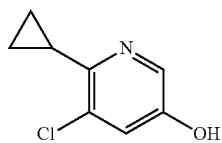 [SMILES: Oc1cnc(C2CC2)c(Cl)c1]

3-Chloro-2-cyclopropyl-5-(4,4,5,5-tetramethyl-1,3,2-dioxaborolan-2-yl)pyridine (Preparation 41, 3.092 mmol assuming 100% in previous step) was dissolved in acetone (10.0 mL) and cooled to 0° C. with an ice bath. Then potassium peroxymonosulfate (2.55 g, 4.15 mmol) in water (10.0 mL) was added dropwise to the mixture and stirred at this temperature for 1 hour. The reaction was then diluted in TBME (25.0 mL) and washed with brine (3×25.0 mL). The organic layer was then dried over sodium sulfate, filtered, and concentrated in vacuo. The resulting crude product was purified with silica gel chromatography eluting with 0 to 30% EtOAc in heptane to yield the title compound as a pale yellow solid (0.220 g, 1.28 mmol, 42% over 2 steps).

$^1$H NMR (400 MHz, d$_6$-DMSO): δ 0.81-0.85 (m, 2H), 0.86-0.91 (m, 2H), 2.26-2.32 (m, 1H), 7.19 (d, 1H), 7.94-7.95 (d, 1H), 10.05 (s, 1H).

LCMS Rt=1.85 minutes MS m/z 170 [MH]$^+$

Preparation 43

2-tert-Butyl-3-chloropyridine

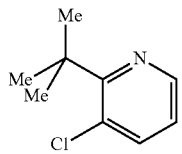 [SMILES: CC(C)(C)c1ncccc1Cl]

2,3-Dichloropyridine (1.0 g, 6.8 mmol) and copper iodide (0.065 g, 0.341 mmol) were dissolved in THF (6 mL). The mixture was degassed three times then cooled to 0° C. with an ice bath. Then tert-butyl(chloro)magnesium in diethylether (5.10 mL, 10.2 mmol) was added dropwise to the reaction mixture under a nitrogen atmosphere keeping the temperature at 0° C. with an ice bath. When the addition was complete, it was left to warm up to room temperature for 16 hours. Brine was slowly added to the reaction mixture (20 mL) and the product extracted with TBME (20 mL). The organic layer was then dried over sodium sulfate, filtered, and concentrated in vacuo. The resulting crude was purified by silica gel chromatography eluting with 0 to 5% EtOAc in heptane to yield the title compound as a yellow oil (0.108 g, 0.6392 mmol).

$^1$H NMR (400 MHz, CDCl$_3$): δ 1.51 (s, 9H), 7.07-7.10 (m, 1H), 7.61-7.63 (m, 1H), 8.42-8.44 (m, 1H).

LCMS Rt=1.55 minutes MS m/z 170 [MH]$^+$

Preparation 44

3-Chloro-2-(1,1-difluoro-2-methylpropyl)pyridine

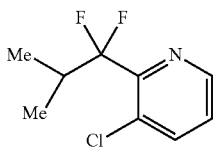 [SMILES: CC(C)C(F)(F)c1ncccc1Cl]

N-Ethyl-N-(trifluoro-lambda~4~-sulfanyl)ethanamine (5.29 mL, 0.040 mol) was added dropwise to a solution of 1-(3-chloropyridin-2-yl)-2-methylpropan-1-one (0.74 g, 0.4 mmol) in DCM (20 mL) under a nitrogen atmosphere. The reaction mixture was stirred at room temperature for 240 hours. DCM was added to the reaction mixture (10 mL), followed by an aqueous solution of saturated brine (3 mL) and water (5 mL). The aqueous layer was further extracted with DCM (2×15 mL). The organics were combined, dried over sodium sulfate, filtered, and concentrated in vacuo. The resulting crude was purified by silica gel chromatography eluting with 0 to 10% EtOAc in heptane to yield the title compound as a brown oil (0.803 g, 1.95 mmol).

$^1$H NMR (400 MHz, CDCl$_3$): δ 1.06-1.07 (d, 6H), 2.74-2.90 (m, 1H), 7.32-7.35 (m, 1H), 7.77-7.80 (m, 1H), 8.50-8.53 (m, 1H).

Preparation 45

3-Chloro-2-(difluoromethoxy)pyridine

2-Hydroxy pyridine (1.0 g, 7.7 mmol) was added slowly to a suspension of NaH (0.34 g, 8.5 mmol) in dry acetonitrile under a nitrogen atmosphere at room temperature and stirred for 10 minutes. Caesium fluoride (0.12 g, 0.77 mmol) was then added followed by slow addition of trimethylsilyl difluoro(fluorosulfonyl)acetate (1.7 mL, 2.1 g, 8.5 mmol). The reaction mixture was quenched with water and most of the solvent removed in vacuo. The residue was partitioned between water and EtOAc. The combined organics were washed with brine, dried over sodium sulfate, filtered, and concentrated in vacuo to yield the title compound as a pale yellow oil (1.3 g).

$^1$H NMR (400 MHz, CDCl$_3$): δ 7.09 (d, 1H), 7.48 (t, 1H), 7.78 (d, 1H), 8.10 (d, 1H).

LCMS Rt=1.37 minutes MS m/z 180 [MH]$^+$

Preparation 46

6-d9-tert-Butoxy-5-chloropyridin-3-ol

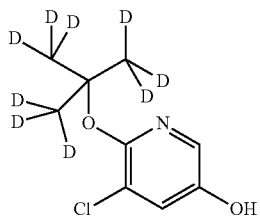 [SMILES: [2H]C([2H])([2H])C(Oc1ncc(O)cc1Cl)(C([2H])([2H])[2H])C([2H])([2H])[2H]]

Hydrogen peroxide solution (30%, 0.462 mL, 4.52 mmol) was added in five portions to a solution of 2-tert-d9-butoxy-3-chloro-5-(4,4,5,5-tetramethyl-1,3,2-dioxaborolan-2-yl)pyridine (Preparation 76, 1.21 g, 3.773 mmol) in MeOH/H$_2$O (30 mL: 10 mL) at 0° C. The reaction mixture was stirred at room temperature for 3.5 hours. Aqueous sodium thiosulfate (0.1 M, 20 mL) was added, then stirred at room temperature for 5 minutes and extracted with EtOAc (50 mL). Organics were washed with brine (2×30 mL), dried over magnesium sulfate and evaporated in vacuo to afford the crude material as a yellow oil. The crude material was purified by silica gel chromatography eluting with 0 to 60% EtOAc in heptane to afford the title compound as a waxy white solid.

$^1$H NMR (400 MHz, CDCl$_3$): δ 4.73 (s, OH), 7.24 (d, 1H), 7.69 (d, 1H).

LCMS Rt=1.27 minutes MS m/z 209 [M-H]$^-$

Preparation 47

3-Chloro-2-d7-isopropoxypyridine

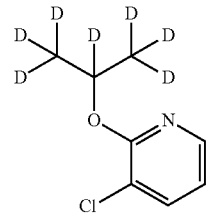 [SMILES: [2H]C([2H])([2H])C([2H])(Oc1ncccc1Cl)C([2H])([2H])[2H]]

A solution of d$^8$-isopropyl alcohol (4.71 mL, 61.5 mmol) in anhydrous THF (10 mL) was added over 1 minute to a suspension of NaH (60% in mineral oil) (2.46 g, 61.5 mmol) in anhydrous THF (50 mL). After 10 minutes, a solution of 2-fluoro-3-chloropyridine (5.05 g, 38.4 mmol) in THF (10 mL) was added over 5 minutes at 5° C. (ice bath). The reaction was then warmed to room temperature stirred for 18 hours. The reaction was diluted with THF (20 mL), cooled to 5° C. (ice bath) and quenched with water (50 mL). The mixture was extracted with EtOAc (50 mL). Brine was added to aid the separation. The organics were dried over magnesium sulfate, filtered, and concentrated in vacuo to afford a crude oil which was purified by silica gel chromatography eluting with 0 to 30% EtOAc in heptane to yield the title compound as a colourless oil (5.37 g).

$^1$H NMR (400 MHz, CDCl$_3$): δ 6.78-6.81 (m, 1H), 7.60-7.62 (m, 1H), 8.03-8.04 (m, 1H).

LCMS Rt=1.41 minutes. Molecular ion not observed.

Preparation 48

5-Chloro-6-(2,2,3,3-tetrafluoropropoxy)pyridin-3-ol

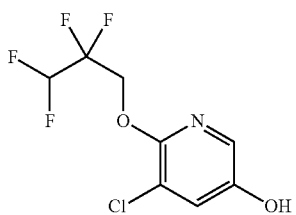 [SMILES: Oc1cnc(OCC(F)(F)C(F)F)c(Cl)c1]

Hydrogen peroxide solution (30% aq. solution, 30.2 mL, 0.26 mol) was added to a solution of 3-chloro-2-(2,2,3,3-tetrafluoropropoxy)-5-(4,4,5,5-tetramethyl-1,3,2-dioxaborolan-2-yl)pyridine (Preparation 49, 81.0 g, 0.22 mol) in methanol (500 mL) at 0° C. and the reaction was allowed to warm up to room temperature for 4 hours. The reaction mixture was quenched with aqueous sodium thiosulphate (10%, 100 mL) and the methanol removed in vacuo. The resulting mixture was extracted with EtOAc (2×250 mL). The combined organics swere dried over magnesium sulfate, filtered and evaporated to yield a yellow oil, which was purified by silica gel chromatogrpahy eluting with 10% EtOAc in heptane to afford the title compound as a viscous colourless oil (46.7 g, 82%).

¹H NMR (400 MHz, CDCl₃): δ 4.60 (t, 2H), 5.60 (br, 1H), 5.95-6.20 (m, 1H), 7.36 (s, 1H), 7.70 (s, 1H).
LCMS Rt=2.43 minutes MS m/z 257 [MH]⁻

Preparation 49

3-Chloro-2-(2,2,3,3-tetrafluoropropoxy)-5-(4,4,5,5-tetramethyl-1,3,2-dioxaborolan-2-yl)pyridine

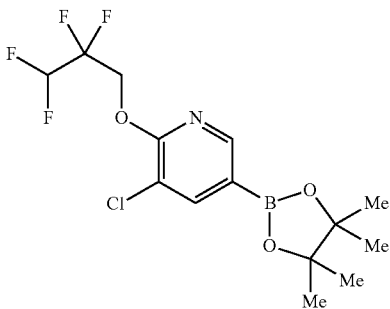 [SMILES: CC1(C)OB(c2cnc(OCC(F)(F)C(F)F)c(Cl)c2)OC1(C)C]

A 3-necked flask was charged with 3-chloro-2-(2,2,3,3-tetrafluoropropoxy)pyridine (Preparation 50, 71.0 g, 0.3 mol) and heptane (350 mL). The mixture was cycled three times between nitrogen and vacuum. Bispinacolatodiboron (74.0 g, 0.3 mol) and di-tert-butyl dipyridyl (4.70 g, 17.5 mmol) were then added and the mixture was degassed again and kept under a nitrogen atmosphere. Then di-μ-methanolatodiiridium(Ir—Ir)-cycloocta-1,5-diene (1:2) (6.00 g, 9.05 mmol) was added and the resulting mixture stirred at room temperature for 16 hours. The reaction mixture was then cooled to 0° C. and MeOH (70 mL) was added dropwise, then concentrated in vacuo and the resulting mixture partitioned between EtOAc (500 mL) and water (300 mL). The organic layer was separated, dried over magnesium sulfate, filtered and evaporated to yield a brown oil. This oil was purified by silica gel chromatography eluting with 0 to 10% EtOAc in heptane to afford the title compound as a colourless oil (81 g, 75%).
¹H NMR (400 MHz, CDCl₃): δ 1.36 (s, 12H), 4.82 (t, 2H), 5.95-6.23 (m, 1H), 8.05 (s, 1H), 8.40 (s, 1H).
MS m/z 370 [M]⁺

Preparation 50

3-Chloro-2-(2,2,3,3-tetrafluoropropoxy)pyridine

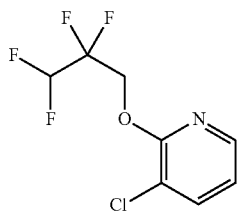 [SMILES: FC(F)C(F)(F)COc1ncccc1Cl]

2,2,3,3-Tetrafluoropropan-1-ol (60.0 g, 0.45 mol) was added to a slurry of NaH (60% dispersion in oil, 15.20 g, 0.63 mol) in anhydrous THF (450 mL) at 0° C. and the reaction mixture allowed to warm up to room temperature, then stirred for 1 hour. 2,3-dichloropyridine (45.0 g, 0.30 mol) was added and the reaction heated to a gentle reflux for 16 hours. The reaction mixture was cooled to room temperature and the solvent removed in vacuo. The residue was partitioned between EtOAc (300 mL) and brine (200 mL). The organic layer was dried over magnesium sulfate, filtered and evaporated to afford the title compound as a yellow oil (71 g, 96%).
¹H NMR (400 MHz, CDCl₃): δ 4.75 (t, 2H), 5.95-6.2 (m, 1H), 6.95 (m, 1H), 7.65 (m, 1H), 8.12 (m, 1H).
LCMS Rt=3.07 minutes Molecular ion not visible Preparation 51

3-Chloro-2-(1,1,1,3,3,3-hexafluoropropan-2-yloxy)-5-nitropyridine

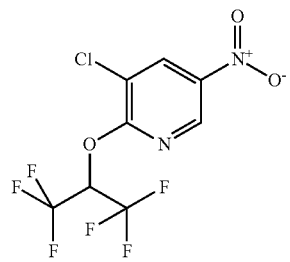 [SMILES: O=[N+]([O-])c1cnc(OC(C(F)(F)F)C(F)(F)F)c(Cl)c1]

1,1,1,3,3,3-Hexafluoropropan-2-ol (1.74 g, 10.35 mmol) was added to a suspension of sodium hydride in mineral oil (60%, 450 mg, 11.25 mmol) in anhydrous THF (10 mL) at 0° C. and over 15 minutes. The resulting suspension was stirred for 30 minutes and 2,3-dichloro-5-nitropyridine (1.50 g, 7.77 mmol) was added portionwise. The mixture was stirred at room temperature for 18 hours and then concentrated in vacuo. The resulting crude was partitioned between EtOAc (50 mL) and water (50 mL). The aqueous layer was extracted with EtOAc (2×25 mL). Combined organics were dried over magnesium sulfate and concentrated in vacuo to afford the title compound as an orange oil (2.55 g, 100%).
¹H NMR (400 MHz, CDCl₃): δ 6.48 (m, 1H), 8.58 (m, 1H), 9.00 (m, 1H).
¹⁹F NMR (400 MHz, CDCl₃): δ -73.0
LCMS Rt=3.48 minutes MS Molecular ion not observed Preparation 52

5-Chloro-6-(1,1,1,3,3,3-hexafluoropropan-2-yloxy)pyridin-3-amine

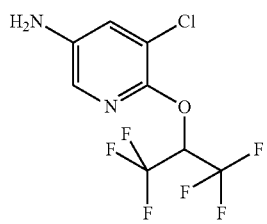 [SMILES: Nc1cnc(OC(C(F)(F)F)C(F)(F)F)c(Cl)c1]

3-Chloro-2-(1,1,1,3,3,3-hexafluoropropan-2-yloxy)-5-nitropyridine (Preparation 51, 2.55 g, 7.9 mmol), ammonium chloride (2.50 g, 46.7 mmol) and iron powder (1.70 g, 30.4 mmol) were suspended in a mixture of ethanol (10 mL) and water (3 mL). The suspension was heated for 3 hours under reflux then allowed to cool to room temperature. The reaction mixture was filtered on a celite pad and washed with ethanol. The filtrate was concentrated in vacuo and the residue partitioned between water and EtOAc. The aqueous layer was further extracted with EtOAc (2×25 mL). The combined organics were dried over magnesium sulfate and concentrated in vacuo. The resulting crude was purified by silica gel chromatography eluting with 50% diethyl ether in heptane to afford the title compound as a light yellow oil (2.0 g, 87%).

$^1$H NMR (400 MHz, CDCl$_3$): δ 3.60 (s, 2H), 6.30 (m, 1H), 7.15 (m, 1H), 7.50 (m, 1H).
$^{19}$F NMR (400 MHz, CDCl$_3$): δ −73.5
LCMS Rt=3.24 minutes MS m/z 295 [MH]$^+$ Preparation 53

5-Chloro-6-(1,1,1,3,3,3-hexafluoropropan-2-yloxy)pyridine-3-diazonium tetrafluoroborate

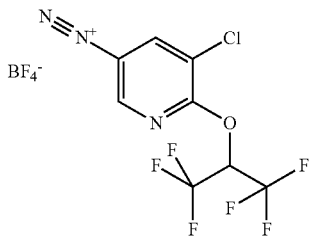

An aqueous solution of tetrafluoroboric acid (48% weight, 1.86 mL, 14.2 mmol) was added to a solution of 5-chloro-6-(1,1,1,3,3,3-hexafluoropropan-2-yloxy)pyridin-3-amine (Preparation 52, 2.0 g, 6.79 mmol) in ethanol (3 mL) at −5° C. Isopentyl nitrite (960 μL, 7.0 mmol) was added dropwise and the reaction mixture was stirred for 30 minutes at −5° C. The suspension was filtered and the solid was washed with cold ethanol and diethyl ether to afford the title compound as a pink solid (728 mg, 27%).

$^1$H NMR (400 MHz, CD$_3$OD): δ 7.30 (m, 1H), 9.20 (m, 1H), 9.50 (m, 1H).

Preparation 54

3-Chloro-2-(1,1,1,3,3,3-hexafluoropropan-2-yloxy)-5-iodopyridine

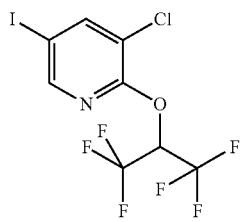 [SMILES: FC(F)(F)C(Oc1ncc(I)cc1Cl)C(F)(F)F]

Potassium iodide (421 mg, 2.53 mmol) was added to a solution of 5-chloro-6-(1,1,1,3,3,3-hexafluoropropan-2-yloxy)pyridine-3-diazonium tetra fluoroborate (Preparation 53, 200 mg, 0.51 mmol) in acetone (10 mL). The mixture was stirred for 15 minutes at room temperature then concentrated in vacuo. The resulting crude residue was partitioned between EtOAc and water. The aqueous layer was further extracted with EtOAc. The combined organics were dried over magnesium sulfate and concentrated in vacuo. The crude material was purified by silica gel chromatography eluting with 10% diethyl ether in heptane to afford the title compound as an orange oil.

$^1$H NMR (400 MHz, CDCl$_3$): δ 6.30 (m, 1H), 7.95 (m, 1H), 8.19 (m, 1H).
LCMS Rt=3.84 minutes Molecular ion not observed Preparation 55

3-Chloro-2-(1,1,1,3,3,3-hexafluoropropan-2-yloxy)-5-(4,4,5,5-tetramethyl-1,3,2-dioxaborolan-2-yl)pyridine

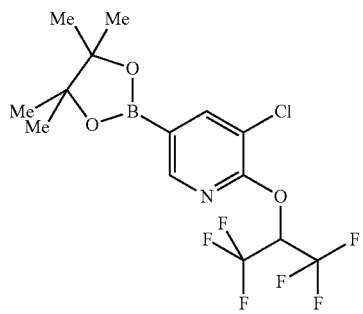 [SMILES: CC1(C)OB(c2cnc(OC(C(F)(F)F)C(F)(F)F)c(Cl)c2)OC1(C)C]

3-Chloro-2-(1,1,1,3,3,3-hexafluoropropan-2-yloxy)-5-iodopyridine (Preparation 54, 300 mg, 0.74 mmol), 1,1'-Bis(diphenylphosphino)ferrocene]dichloropalladium(II) (27 mg, 0.07 mmol), bis(pinacolato)diboron (225 mg, 0.89 mmol), and potassium acetate (218 mg, 2.22 mmol) were suspended in dioxane (10 mL) and degassed for 30 minutes with nitrogen then heated for 18 hours at 90° C. The reaction mixture was recharged with 1,1'-Bis(diphenylphosphino)ferrocene]dichloropalladium(II) (27 mg, 0.07 mmol), bis(pinacolato)diboron (225 mg, 0.89 mmol) and potassium acetate (218 mg, 2.22 mmol) and heated for another 18 hours at 90° C. The reaction mixture was allowed to cool to room temperature and filtered on a pad of arbocel. The pad was washed with EtOAc and MTBE. The filtrate was concentrated in vacuo to afford the title compound as a dark brown solid, which was used without further purification in the next step.

The following examples were prepared according to the method described for Preparation 8, using the corresponding boronic acid or boronic acid ester.

| Prep | Name | Data |
| --- | --- | --- |
| 56 | 5-Chloro-6-methoxypyridin-3-ol | $^1$H NMR (400 MHz, CDCl$_3$): δ 3.96 (s, 3 H), 7.29 (d, 1 H), 7.70 (d, 1 H). LCMS Rt = 1.00 min. MS m/z 160[MH]$^+$, 158[M − H]$^-$ |
| 57 | 5-Chloro-6-(2,2,2-trifluoroethoxy)pyridin-3-ol | LCMS Rt = 2.61 min. MS m/z 228[MH]$^+$ |

| Prep | Name | Data |
|---|---|---|
| 58 | 5-Chloro-6-((1-methylcyclopropyl)methoxy)pyridin-3-ol | $^1$H NMR (400 MHz, CDCl$_3$): δ 0.40 (m, 2H), 0.60 (m, 2H), 1.20 (s, 3H), 4.10 (s, 2H), 4.80 (br, 1H), 7.30 (s, 1H), 7.65 (s, 1H). LCMS Rt = 3.07 min. MS m/z 212[M − H]$^-$ |
| 59 | 5-Chloro-6-(cyclopropylmethoxy)pyridin-3-ol | $^1$H NMR (400 MHz, CDCl$_3$): δ 0.30 (m, 2H), 0.55 (m, 2H), 1.25 (m, 1H), 4.10 (s, 2H), 4.85 (br, 1H), 7.30 (s, 1H), 7.60 (s, 1H). LCMS Rt = 2.86 min. MS m/z 200[MH]$^+$ |
| 60 | 5-Chloro-6-(2,2,3,3,3-pentafluoropropoxy)pyridin-3-ol | $^1$H NMR (400 MHz, CDCl$_3$): δ 4.80 (t, 2H), 5.20 (br, 1H), 7.30 (s, 1H), 7.65 (s, 1H). LCMS Rt = 2.60 min. MS m/z 278[MH]$^+$ |

The following examples were prepared according to the method described for Preparation 42, using the corresponding boronic acid ester.

| Prep | Name | Data |
|---|---|---|
| 61 | 5-Chloro-6-(trifluoromethyl)pyridin-3-ol | $^1$H NMR (400 MHz, d$_6$-DMSO): δ 7.48-7.49 (d, 1H), 8.17-8.18 (d, 1H), 11.42 (s, 1H). LCMS Rt = 1.10 min. MS m/z 198[MH]$^+$ |
| 62 | 6-tert-Butyl-5-chloropyridin-3-ol | $^1$H NMR (400 MHz, d$_6$-DMSO): δ 1.37 (s, 9H), (d, 1H), 7.99 (d, 1H), 10.13 (s, 1H). LCMS Rt = 1.29 min. MS m/z 186[MH]$^+$ |
| 63 | 5-Chloro-6-(1,1-difluoro-2-methylpropyl)pyridin-3-ol | $^1$H NMR (400 MHz, d$_6$-DMSO): δ 0.96-0.97 (d, 6H), 2.69-2.84 (m, 1H), 7.35 (d, 1H), 8.13 (d, 1H), 10.99 (s, 1H). LCMS Rt = 1.41 min. MS m/z 222[MH]$^+$ |
| 64 | 5-Chloro-6-(difluoromethoxy)pyridin-3-ol | $^1$H NMR (400 MHz, CDCl$_3$): δ 7.32 (t, 1H), 7.38 (d, 1H), 7.73 (d, 1H). LCMS Rt = 1.30 min. MS m/z 196[MH]$^+$ |
| 65 | 5-Chloro-6-d1-isopropoxypyridin-3-ol | $^1$H NMR (400 MHz, CDCl$_3$): δ 1.36 (s, 6H), 7.28 (d, 1H), 7.69 (d, 1H). LCMS Rt = 1.24 min. MS m/z 187[M − H]$^-$ |
| 66 | 5-Chloro-6-d7-isopropoxypyridin-3-ol | $^1$H NMR (400 MHz, CDCl$_3$): δ 4.77 (s, 1H), 7.28 (d, 1H), 7.68-7.69 (d, 1H). LCMS Rt = 1.19 min. MS m/z 193[M − H]$^-$ |

The following examples were prepared according to the method described for preparation 46, using the corresponding boronic acid ester.

| Prep | Name | Data |
|---|---|---|
| 67 | 5-Chloro-6-(3,3,3-trifluoropropoxy)pyridin-3-ol | $^1$H NMR (400 MHz, CDCl$_3$): δ 2.7 (m, 2H), 4.5 (t, 2H), 5.24 (br, 1H), 7.3 (s, 1H), 7.7 (s, 1H). LCMS Rt = 2.11 min. MS m/z 242[MH]$^+$ |
| 68 | 6-tert-Butoxy-5-chloropyridin-3-ol | $^1$H NMR (400 MHz, CDCl$_3$): δ 1.60 (s, 9H), 6.9 (br, 1H), 7.25 (s, 1H), 7.65 (s, 1H). LCMS Rt = 2.64 min. Molecular ion not observed. |
| 69 | 5-Chloro-6-(2-fluoro-2-methylpropoxy)pyridin-3-ol | $^1$H NMR (400 MHz, CDCl$_3$): δ 1.45 (s, 3H), 1.50 (s, 3H), 4.30 (d, 2H), 4.95 (br, 1H), 7.30 (s, 1H), 7.65 (s, 1H). LCMS Rt = 2.81 min. MS m/z 220[MH]$^+$ |
| 70 | 5-Chloro-6-(2,2,2-trifluoro-1-methylethoxy)pyridin-3-ol | $^1$H NMR (400 MHz CDCl$_3$): δ 1.4 (d, 3H), 5.1 (br, 1H), 5.6 (m, 1H), 7.3 (s, 1H), 7.65 (s, 1H). LCMS Rt = 2.61 min. MS m/z 240[M − H]$^-$ |
| 71 | 5-Chloro-6-(1,1,1,3,3,3-hexafluoropropan-2-yloxy)pyridin-3-ol | $^1$H NMR (400 MHz, d$_6$-DMSO): δ 6.95 (m, 1H), 7.50 (s, 1H), 7.75 (s, 1H). LCMS Rt = 3.06 min. MS m/z 294[M − H]$^-$ |

The following examples were prepared according to the method described for preparation 33, using the corresponding pyridine.

| Prep | Name | Data |
| --- | --- | --- |
| 72 | 3-Chloro-5-(4,4,5,5-tetramethyl-1,3,2-dioxaborolan-2-yl)-2-(trifluoromethyl)pyridine | Reaction mixture evaporated to dryness and taken to next step without purification. |
| 73 | 2-tert-Butyl-3-chloro-5-(4,4,5,5-tetramethyl-1,3,2-dioxaborolan-2-yl)pyridine | $^1$H NMR (400 MHz, d$_6$-DMSO): δ 1.29 (s, 12H), 1.43 (s, 9H), 7.85-7.86 (d, 1H), 8.58 (d, 1H). LCMS Rt = 1.13 min. Molecular ion not observed. |
| 74 | 3-Chloro-2-(1,1-difluoro-2-methylpropyl)-5-(4,4,5,5-tetramethyl-1,3,2-dioxaborolan-2-yl)pyridine | Reaction mixture evaporated to dryness and taken to next step without purification. |
| 75 | 3-Chloro-2-(difluoromethoxy)-5-(4,4,5,5-tetramethyl-1,3,2-dioxaborolan-2-yl)pyridine | LCMS Rt = 1.82 min. MS m/z 305 [M H]$^+$ |
| 76 | 2-d9-tert-Butoxy-3-chloro-5-(4,4,5,5-tetramethyl-1,3,2-dioxaborolan-2-yl)pyridine | $^1$H NMR (400 MHz, CDCl$_3$): δ 1.32 (s, 12H), 7.92 (d, 1H), 8.36 (d, 1H). LCMS Rt = 2.00 min. Molecular ion not observed. |
| 77 | 3-Chloro-5-(4,4,5,5-tetramethyl-1,3,2-dioxaborolan-2-yl)-2-(3,3,3-trifluoropropoxy)pyridine | $^1$H NMR (400 MHz CDCl$_3$): 1.3 (s, 12H), 2.7 (m, 2H), 4.7 (m, 2H), 8.0 (s, 1H), 8.4 (s, 1H). LCMS = 4.03 min. MS m/z 352 [MH]$^+$ |
| 78 | 3-Chloro-2-d7-isopropoxy-5-(4,4,5,5-tetramethyl-1,3,2-dioxaborolan-2-yl)pyridine | $^1$H NMR (400 MHz, CDCl$_3$): δ 1.34 (s, 12H), 7.95-7.96 (d, 1H), 8.38 (d, 1H). LCMS Rt = 1.81 min. MS m/z 305 [MH]$^+$ |
| 79 | 3-Chloro-2-d1-isopropoxy-5-(4,4,5,5-tetramethyl-1,3,2-dioxaborolan-2-yl)pyridine | $^1$H NMR (400 MHz, CDCl$_3$): δ 1.34 (s, 12H), 1.39 (s, 6H), 7.95-7.96 (d, 1H), 8.38 (d, 1H). LCMS Rt = 1.83 min. Molecular ion not observed. |

-continued

| Prep | Name | Data |
|---|---|---|
| 80 | 3-Chloro-2-((1-methylcyclopropyl)methoxy)-5-(4,4,5,5-tetramethyl-1,3,2-dioxaborolan-2-yl)pyridine | $^1$H NMR (400 MHz CDCl$_3$): δ 0.42 (m, 2H), 0.60 (m, 2H), 1.39-1.24 (m, 15H), 4.22 (s, 2H), 7.97 (d, 1H), 8.35 (d, 1H). |
| 81 | 2-tert-Butoxy-3-chloro-5-(4,4,5,5-tetramethyl-1,3,2-dioxaborolan-2-yl)pyridine | $^1$H NMR (400 MHz, CDCl$_3$): δ 1.25 (s, 12H), 1.60 (s, 9H), 7.80 (s, 1H), 8.4 (s, 1H). |
| 82 | 3-Chloro-2-(cyclopropylmethoxy)-5-(4,4,5,5-tetramethyl-1,3,2-dioxaborolan-2-yl)pyridine | $^1$H NMR (400 MHz, CDCl$_3$): δ 0.41-0.38 (m, 2H), 0.64-0.59 (m, 2H), 1.38-1.24 (m, 13H), 4.27 (d, 2H), 7.97 (d, 1H), 8.37 (d, 1H). |
| 83 | 3-Chloro-2-(2,2,3,3,3-pentafluoropropoxy)-5-(4,4,5,5-tetramethyl-1,3,2-dioxaborolan-2-yl)pyridine | $^1$H NMR (400 MHz, CDCl$_3$): δ 1.30 (s, 12H), 4.85 (t, 2H), 8.00 (s, 1H), 8.30 (s, 1H). |
| 84 | 3-Chloro-2-(2-fluoro-2-methylpropoxy)-5-(4,4,5,5-tetramethyl-1,3,2-dioxaborolan-2-yl)pyridine | $^1$H NMR (400 MHz, CDCl$_3$): δ 1.35 (s, 12H), 1.50 (s, 3H), 1.55 (s, 3H), 4.40 (d, 2H), 8.00 (s, 1H), 8.40 (s, 1H). MS m/z 330 [MH]$^+$ |
| 85 | 3-Chloro-5-(4,4,5,5-tetramethyl-1,3,2-dioxaborolan-2-yl)-2-(2,2,2-trifluoro-1-methylethoxy)pyridine | $^1$H NMR (400 MHz, CDCl$_3$): δ 1.4 (s, 12H), 1.5 (d, 3H), 5.8 (m, 1H), 8.0 (s, 1H), 8.4 (s, 1H). LCMS Rt = 2.80 min. Molecular ion not observed. |
| 86 | 3-Chloro-5-(4,4,5,5-tetramethyl-1,3,2-dioxaborolan-2-yl)-2-(2,2,2-trifluoroethoxy)pyridine | $^1$H NMR (400 MHz, CDCl$_3$): δ 1.35 (s, 12H), 4.86 (m, 2H), 8.05 (d, 1H), 8.38 (d, 1H). |

The following examples were prepared according to the method described for Preparation 32 above, using the corresponding pyridine and alcohol precursors.

| Prep | Name | Data |
|---|---|---|
| 87 | 2-d9-tert-Butoxy-3-chloropyridine | $^1$H NMR (400 MHz, CDCl$_3$): δ 6.72-6.80 (m, 1H), 7.55-7.61 (m, 1H), 8.00 (m, 1H). LCMS Rt = 1.49 min. |
| 88 | 3-Chloro-2-(3,3,3-trifluoropropoxy)pyridine | $^1$H NMR (400 MHz, CDCl$_3$): δ 2.7 (m, 2H), 4.6 (t, 2H), 6.9 (m, 1H), 7.6 (d, 1H), 8.0 (s, 1H). |
| 89 | 3-Chloro-2-d1-isopropoxypyridine | $^1$H NMR (400 MHz, CDCl$_3$): δ 1.39 (s, 6H), 6.78-6.81 (m, 1H), 7.60-7.62 (m, 1H), 8.02-8.04 (m, 1H). LCMS Rt = 1.44 min. MS m/z 173 [MH]$^+$ |
| 90 | 3-Chloro-2-((1-methylcyclopropyl)methoxy)pyridine | $^1$H NMR (400 MHz, CDCl$_3$): δ 0.43 (m, 2H), 0.60 (m, 2H), 1.26 (s, 3H), 4.17 (s, 2H), 6.82 (m, 1H), 7.63 (m, 1H), 8.01 (m, 1H). LCMS Rt = 1.75 min. Molecular ion not observed. |
| 91 | 3-Chloro-2-(cyclopropylmethoxy)pyridine | $^1$H NMR (400 MHz, CDCl$_3$): δ 0.03-0.01 (m, 2H), 0.26-0.21 (m, 2H), 0.96 (m, 1H), 3.85 (d, 2H), 6.44 (m, 1H), 7.24 (m, 1H), 7.64 (m, 1H). LCMS Rt = 1.64 min. MS m/z 184[MH]$^+$ |
| 92 | 2-tert-Butoxy-3-chloropyridine | $^1$H NMR (400 MHz, CDCl$_3$): δ 1.6 (s, 9H), 6.80 (m, 1H), 7.60 (d, 1H), 8.0 (s, 1H). LCMS Rt = 2.01 min. MS m/z 186[MH]$^+$ |
| 93 | 3-Chloro-2-(2,2,3,3,3-pentafluoropropoxy)pyridine | $^1$H NMR (400 MHz, CDCl$_3$): δ 4.95 (t, 2H), 6.95 (m, 1H), 7.70 (s, 1H), 8.05 (d, 1H). LCMS Rt = 3.51 min. Molecular ion not observed. |
| 94 | 3-Chloro-2-(2-fluoro-2-methylpropoxy)pyridine | $^1$H NMR (400 MHz, CDCl$_3$): δ 1.50 (s, 3H), 1.55 (s, 3H), 4.40 (d, 2H), 6.85 (m, 1H), 7.65 (d, 1H), 8.00 (d, 1H). LCMS Rt = 3.20 min. MS m/z 204[MH]$^+$ |
| 95 | 3-Chloro-2-(2,2,2-trifluoro-1-methylethoxy)pyridine | $^1$H NMR (400 MHz, CDCl$_3$): δ 1.6 (d, 3H), 5.8 (m, 1H), 6.85 (m, 1H), 7.6 (m, 1H), 8.0 (m, 1H). LCMS Rt = 3.69 min. Molecular ion not observed. |
| 96 | 3-Chloro-2-(2,2,2-trifluoroethoxy)pyridine | $^1$H NMR (400 MHz, CDCl$_3$): δ 4.83 (m, 2H), 6.96 (m, 1H), 7.70 (m, 1H), 8.05 (m, 1H). LCMS Rt = 3.21 min. Molecular ion not observed. |

Preparation 97 tert-Butyl 2,4,5-trifluorobenzoate

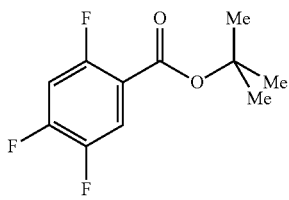 [SMILES: CC(C)(C)OC(=O)c1cc(F)c(F)cc1F]

2,4,5-Trifluorobenzoic acid (10.0 g, 56.8 mmol) was dissolved in tert-butanol (280 mL). Di-tert-butyl dicarbonate (24.8 g, 114 mmol) was added portionwise followed by DMAP (0.694 g, 5.68 mmol) and the mixture stirred at 30° C. under nitrogen for 16 hours. EtOAc (400 mL) was added and the mixture washed with an aqueous solution of HCl (1.0 M, 2×50 mL), then with a saturated aqueous solution of sodium hydrogen carbonate (2×50 mL), and finally with brine (2×50 mL). The organic layer was dried over sodium sulfate, filtered, and concentrated in vacuo to afford the title compound as a colourless oil (12.31 g, 93%):
$^1$H NMR (400 MHz, CDCl$_3$): δ 1.58 (s, 9H), 6.93-6.99 (m, 1H), 6.68-6.74 (m, 1H).

Preparation 98

2,3-Dicyclopropylpyridine

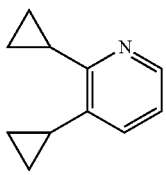 [SMILES: c1cnc(C2CC2)c(C2CC2)c1]

3-Chloro-2-bromopyridine (5.0 g, 26.0 mmol) and potassium phosphate tribasic (19.3 g, 90.9 mmol) were suspended in toluene (40 mL) and water (2 mL). The reaction mixture was sonicated for 10 minutes, and then cyclopropylboronic acid (1.12 g, 13.0 mmol), palladium acetate (0.093 g, 0.414 mmol) and tricyclohexylphosphine (0.243 g, 0.867 mmol) were added to the reaction mixture, which was then placed in a pre heated DrySyn® bath at 100° C. The reaction mixture was then left to stir under nitrogen for two hours. Additional cyclopropylboronic acid (1.12 g, 13.0 mmol), palladium acetate (0.093 g, 0.414 mol) and tricyclohexylphosphine (0.243 g, 0.867 mmol) were added to the reaction mixture which was stirred for a further two hours. Additional cyclopropylboronic acid (1.12 g, 13.0 mmol), palladium acetate (0.093 g, 0.414 mmol) and tricyclohexylphosphine (0.243 g, 0.867 mmol) were again added to the reaction mixture which was stirred for a further two hours. The mixture was then left to stir at room temperature for 16 hours. The reaction mixture was diluted in ethyl acetate (40 mL) and water (40 mL) and was filtered on a pad of Arbocel® under a stream of nitrogen. The organic layer was then separated and washed three times with a 10% solution of aqueous citric acid (25 mL). The organic layer was discarded and the aqueous layer brought back to basic pH with careful addition of a saturated aqueous solution of sodium hydrogen carbonate (100 mL). The product was extracted three times with tert-butyl methyl ether (20 mL). The organic layers were combined, then dried over sodium sulfate, filtered, and concentrated in vacuo. The title compound was isolated as an orange oil (0.66 g, 16%):
$^1$H NMR (400 MHz, DMSO-d$_6$): δ 0.60-0.64 (m, 2H), 0.88-0.96 (m, 6H), 2.06-2.14 (m, 1H), 2.45-2.52 (m, 1H), 6.99 (d, 1H), 7.27 (d, 1H), 8.17 (d, 1H)
LCMS Rt=0.74 minutes MS m/z 160 [MH]+

Preparation 99

5,6-Dicyclopropylpyridin-3-ol

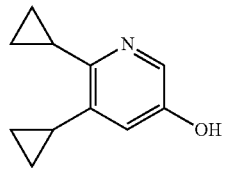 [SMILES: Oc1cnc(C2CC2)c(C2CC2)c1]

A round bottom flask was charged with the compound from preparation 98 (0.660 g; 4.15 mmol), bis(pinacolato)diboron (1.3 g, 5.1 mmol) and 4,4-di-tert-butyl-2,2-dipyridyl (0.033 g; 0.12 mmol) in heptane (10 mL). The reaction mixture was cycled between vacuum and nitrogen 3 times over 15 minutes. Di-μ-methanolatodiiridium(Ir—Ir)-cycloocta-1,5-diene (1:2) (0.084 g; 0.12 mmol) was then added and the reaction left to stir at 85° C. for 18 hours under nitrogen. The reaction mixture was evaporated to dryness to afford a red viscous oil. The crude material was dissolved in acetone (10 mL) and cooled to 0° C. with an ice bath. Oxone (3.40 g, 5.53 mmol) in water (10 mL) was then added dropwise to the mixture, which was stirred at this temperature for 1 hour. The reaction was then diluted in tert-butyl methyl ether (25 mL) and washed three times with an aqueous solution of saturated brine (25 mL). The organic layer was discarded and the aqueous layer was brought to basic pH with careful addition of a saturated aqueous solution of sodium hydrogen carbonate (100 mL). The product was extracted three times with tert-butyl methyl ether (20 mL). The organic layers were combined, dried over sodium sulfate, filtered, and concentrated in vacuo. The resulting crude product was purified by silica gel chromatography (ISCO® 12 g cartridge) eluting with 0 to 50% EtOAc in heptane to yield the title compound as a pale yellow solid (0.21 g, 29%):
$^1$H NMR (400 MHz, DMSO-d$_6$): δ 0.55-0.59 (m, 2H), 0.80 (d, 4H), 0.90-0.95 (m, 2H), 2.03-2.08 (m, 1H), 2.29-2.35 (m, 1H), 6.65 (m, 1H), 7.74-7.75 (m, 1H), 9.35 (s, 1H)
LCMS Rt=0.91 minutes MS m/z 176 [MH]+

Preparation 100

2-Isopropoxy-5-(4,4,5,5-tetramethyl-1,3,2-dioxaborolan-2-yl)pyrimidine

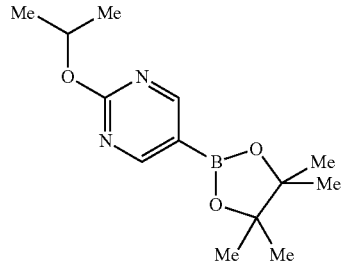 [SMILES: CC(C)Oc1ncc(B2OC(C)(C)C(C)(C)O2)cn1]

5-Bromo-2-isoproxypyrimidine (171 g, 787.8 mmol), bis(pinacolato)diboron (290 g, 1.14 mol), potassium acetate (237 g, 2.36 mol) and 1,1'-bis(diphenylphosphino)ferrocene palladium dichloride (9.10 g, 12.44 mmol) were mixed under nitrogen at room temperature in dioxane (1 L). The mixture was heated at 95° C. for 30 minutes and then at 105° C. until the reaction was complete. The solution was diluted with water (1 L) and dichloromethane (2 L) and filtered through celite. The layers were separated and the organic layer was washed with water (1 L), dried over sodium sulfate, filtered and evaporated to give an oil. The oil was purified by silica gel chromatography eluting with 0 to 5% EtOAc in hexane to yield the title compound as a white solid (162 g, 54%).

$^1$H NMR (400 MHz, DMSO-$d_6$): δ 1.30-1.32 (m, 18H), 5.22-5.28 (m, 1H), 8.70 (s, 2H). Molecular ion not observed.

Preparation 101

2-Isopropoxypyrimidin-5-ol

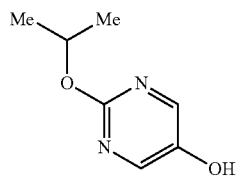

An aqueous solution (5 mL) of potassium peroxymonosulfate (1.40 g, 2.27 mmol) was added dropwise to a solution of 2-isopropoxy-5-(4,4,5,5-tetramethyl-1,3,2-dioxaborolan-2-yl)pyrimidine (Preparation 100, 500 mg, 1.89 mmol) in acetone (5 ml) under a nitrogen atmosphere at 0° C. The mixture was stirred at room temperature for 2 hours, then filtered, the filtrate diluted with water (30 mL) and extracted with EtOAc (1×20 mL). The organic layer was washed with brine (2×20 mL), dried over sodium sulfate, filtered and evaporated in vacuo. The resulting oil was dissolved in dichloromethane and purified by silica gel chromatography eluting with 0 to 5% MeOH (with 10% aqueous ammonia) in dichloromethane to yield a solid. The solid was suspended in diethyl ether and evaporated to yield the title compound as a white solid (100 mg, 34%):

$^1$H NMR (400 MHz; CDCl$_3$): δ 1.37 (d, 6H), 1.97 (br s, 1H), 5.14-5.31 (m, 1H), 8.20 (s, 2H).

LCMS Rt=10 minutes. Ms m/z 153 [M-H]$^-$

Preparation 102

2-Bromo-3-difluoromethoxypyridine

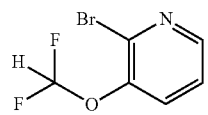

To a solution of 2-bromo-3-pyridinol (1.26 g, 7.23 mmol) in DMF (35 mL) and water (5 mL) was added sodium chlorodifluoroacetate (2.93 g, 18.1 mmol) followed by cesium carbonate (4.71 g, 14.5 mmol). The reaction was heated to 100° C. for 36 hours before partitioning between EtOAc and water. The organic layer was collected, dried over magnesium sulfate and concentrated in vacuo. The residue was purified using silica gel column chromatography eluting with EtOAc:heptane 1:3 to afford the title compound as a colourless oil (570 mg, 35%).

$^1$H NMR (400 MHz; DMSO-$d_6$): δ 7.15-7.55 (t, 1H), 7.55 (m, 1H), 7.80 (m, 1H), 8.25 (m, 1H).

LCMS Rt=1.91 minutes MS m/z 226 [M$^{79}$BrH]$^+$

Preparation 103

2-Cyclopropyl-3-(difluoromethoxy)pyridine

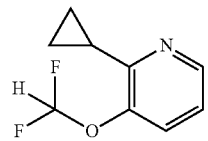

Cyclopropylboronic acid (383 mg, 4.5 mmol) and potassium phosphate tribasic (1.89 g, 8.9 mmol) were added to a solution of 2-bromo-3-difluoromethoxypyridine (Preparation 102, 570 mg, 2.5 mmol). The mixture was heated to 80° C. and degassed thoroughly by bubbling nitrogen through the mixture. After 30 minutes, the reaction was heated to 95° C. and tricyclohexylphosphine (84 mg, 0.30 mmol) was added followed by palladium acetate (32 mg, 0.14 mmol). The reaction was stirred at 95° C. for 18 hours then cooled to room temperature. The mixture was filtered through arbocel, washing with EtOAc and the filtrate concentrated in vacuo. The residue was then purified by flash column chromatography eluting with EtOAc:heptane 1:5 to afford the title compound as a colourless oil (273 mg, 58%).

$^1$H NMR (400 MHz; DMSO-$d_6$): δ 0.95 (m, 4H), 2.30 (m, 1H), 7.05-7.42 (t, 1H), 7.15 (m, 1H), 7.5 (m, 1H), 8.25 (m, 1H).

LCMS Rt=2.09 minutes MS m/z 186 [MH]$^+$

Preparation 104

2-Cyclopropyl-3-difluoromethoxy-5-(4,4,5,5-tetramethyl-1,3,2-dioxaborolan-2-yl)pyridine

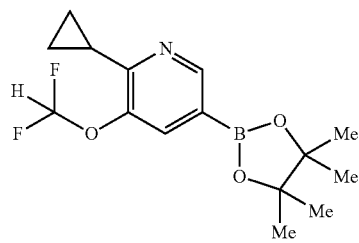 [SMILES: CC1(C)OB(c2cnc(C3CC3)c(OC(F)F)c2)OC1(C)C]

Bis(pinacolato)diboron (444 mg, 1.8 mmol) was added to a solution of 2-cyclopropyl-3-(difluoromethoxy)pyridine (270 mg, 1.5 mmol) in dioxane (5 mL). The solution was de-gassed by bubbling N$_2$ through the solution for 30 minutes. The solution was then heated to 90° C., and 4,4-di-tert-butyl-2,2-dipyridyl (4 mg, 0.015 mmol) and cyclooctadiene (dimethoxy) Iridium (I) dimer (10 mg, 0.015 mmol) were added. The flask was de-gassed with N$_2$ (×3), and left at 90° C. for 18 hours. The reaction was cooled then quenched by slow addition of methanol (20 mL) and concentrated to dryness to afford the title compound as a red-brown oil (454 mg). This was used in the subsequent reaction without further purification.
LCMS Rt=1.55 minutes MS m/z 230 [MH]+

Preparation 105

6-Cyclopropyl-5-(difluoromethoxy)pyridin-3-ol

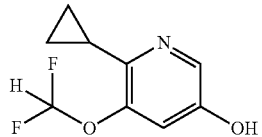

Methanol (5 mL) was added to the crude 2-cyclopropyl-3-difluoromethoxy-5-(4,4,5,5-tetramethyl-1,3,2-dioxaborolan-2-yl)pyridine (Preparation 103, 450 mg, 1.5 mmol) and the resulting solution cooled to 0° C. with stirring. Hydrogen peroxide solution (35% in water, 0.70 mL) was added over 20 minutes. The reaction mixture was then allowed to warm to room temperature and stirred for 5 hours. The reaction was quenched by addition of 1M aqueous sodium thiosulfate solution (10 mL), and rapidly stirred for 15 minutes at room temperature. The mixture were evaporated in vacuo, and brine (50 mL) was added. The residue was extracted into ethyl acetate (3×50 mL) and the combined extracts were dried over magnesium sulfate, filtered and the solvent removed to leave a brown oil. The oil was purified by flash silica gel column chromatography eluting with EtOAc:heptane 1:1 to provide the title compound as a white solid (168 mg, 58% yield).
$^1$H NMR (400 MHz; DMSO-$d_6$): δ 0.80 (m, 4H), 2.10-2.20 (m, 1H), 6.95 (m, 1H), 7.00-7.40 (t, 1H), 7.85 (m, 1H), 10.00 (br s, 1H).
LCMS Rt=1.68 minutes MS m/z 202 [MH]+

Preparation 106

2-(4-Bromobenzyloxy)-5-chloro-4-(trifluoromethyl)pyridine

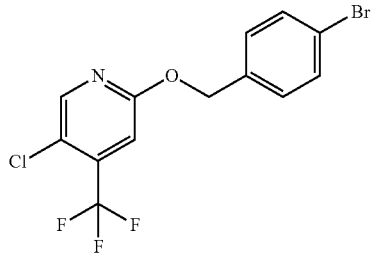 [SMILES: FC(F)(F)c1cc(OCc2ccc(Br)cc2)ncc1Cl]

To a solution of 4-bromobenzylbromide (0.43 g, 2.3 mmol) in tetrahydrofuran (8 mL) at 0° C. was added sodium hydride (60% w/w dispersion in oil; 138 mg, 3.45 mmol). The mixture was stirred for 1 hour at room temperature, then 2,5-dichloro-4-trifluoromethylpyridine (0.5 g, 2.3 mmol) was added in one portion and the reaction heated under reflux for 4 hours. The reaction mixture was cooled and partitioned between ethyl acetate (30 mL) and water (10 mL). The organic layer was dried over magnesium sulfate, filtered and evaporated in vacuo to give the crude title compound (0.61 g, 71%). This was used without further purification.
$^1$H NMR (400 MHz, MeOD-$d_4$): δ 5.25 (s, 2H), 7.05 (s, 1H), 7.30 (d, 2H), 7.50 (d, 2H), 8.12 (s, 1H).

Preparation 107

2-(4-Bromobenzyloxy)-5-chloropyridine

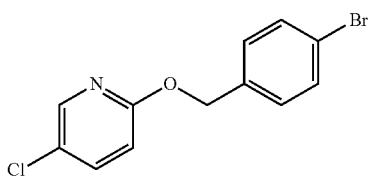 [SMILES: Clc1ccc(OCc2ccc(Br)cc2)nc1]

To a solution of 4-bromobenzylbromide (1.26 g, 6.7 mmol) in tetrahydrofuran (10 mL) at 0° C. was added a sodium hydride (60% w/w dispersion in oil; 0.40 g, 10 mmol). The mixture was stirred for 1 hour at room temperature, then 2,5-dichloro pyridine (1 g, 6.7 mmol) was added in one portion and the reaction mixture was heated under reflux overnight. TLC The reaction mixture was cooled and partitioned between ethyl acetate (40 mL) and cold water (10 mL). The organic layer was dried over magnesium sulfate, filtered and evaporated in vacuo to give the crude title compound (1.54 g, 76%). This was used without further purification.
$^1$H NMR (400 MHz, MeOD-$d_4$): δ 5.15 (s, 2H), 7.18 (d, 2H), 7.35 (d, 2H), 7.38 (m, 1H), 8.05 (s, 2H).

Preparation 108

2,4,5-Trifluoro-N-(methylsulfonyl)benzamide

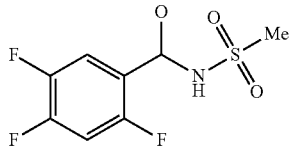 [SMILES: CS(=O)(=O)NC(O)c1cc(F)c(F)cc1F]

2,4,5-Trifluorobenzoic acid (3.00 g, 17.0 mmol), N-ethyl-N-isopropylpropan-2-amine (8.9 mL, 6.6 g, 51.1 mmol), 2,4,6-tripropyl-1,3,5,2,4,6-trioxatriphosphorinane-2,4,6-trioxide 50% solution in EtOAc/DMF (12.7 mL, 13.6 g, 42.6 mmol) and methanesulfonamide (3.24 g, 34.1 mmol) were suspended in THF (40 mL) and stirred under a nitrogen atmosphere at reflux for 18 hours. The reaction mixture was cooled, concentrated in vacuo and the residue suspended in water (pH=4). The mixture was acidified to pH=2 with an aqueous solution of potassium hydrogen sulfate (0.5 M). The mixture was extracted with EtOAc (1×100 mL). The organic layer was washed with brine (2×50 mL), dried over sodium sulfate, filtered and evaporated to yield the crude solid. The crude solid was triturated with hexane to yield the title compound as an off-white crystalline solid (3.08 g, 72%).

¹H NMR (400 MHz, CDCl₃): δ 3.45 (s, 3H), 7.10-7.13 (m, 1H), 7.97-8.02 (m, 1H), 8.74 (br, 1H). ¹⁹FNMR (400 MHz, CDCl₃): δ −112.4, −121.9, −138.5.

Preparation 109

4-tert-butoxy-2,5-difluoro-N-(methylsulfonyl)benzamide

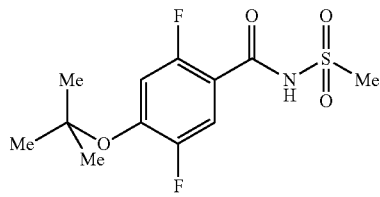 [SMILES: CC(C)(C)Oc1cc(F)c(C(=O)NS(C)(=O)=O)cc1F]

Potassium tert-butoxide (1.46 g, 13.0 mmol) was added to a solution of 2,4,5-trifluoro-N-(methylsulfonyl)benzamide (Preparation 108, 1.5 g, 5.924 mmol) in DMSO (10 mL) and stirred at room temperature. After 3 hours, potassium tert-butoxide (140 mg, 1.3 mmol) was further added and stirred for 18 hours more. The reaction mixture was diluted with EtOAc and 10% aqueous citric acid solution. The pH of the water layer was acidic. The organic layer was washed with more 10% aqueous citric acid and brine, then dried over magnesium sulfate, filtered and concentrated in vacuo to yield the title compound as a cream solid (1.76 g, 100%).

Preparation 110

2,5-Difluoro-4-hydroxy-N-(methylsulfonyl)benzamide

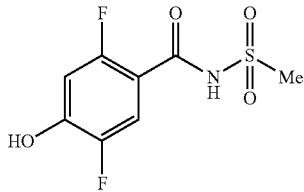 [SMILES: CS(=O)(=O)NC(=O)c1cc(F)c(O)cc1F]

Hydrochloric acid solution in dioxane (4 M, 30 mL) was added to the 4-tert-butoxy-2,5-difluoro-N-(methylsulfonyl) benzamide (Preparation 109, 1.76 g, 5.73 mmol) and the resulting solution stirred at room temperature. After 3 hours the reaction mixture was concentrated in vacuo and the residue azeotroped repeatedly with DCM to yield the title compound as a white solid (1.49 g, 100%).

¹H NMR (400 MHz; CDCl₃): δ 3.25 (s, 3H), 6.60-6.68 (m, 1H), 7.45-7.55 (m, 1H), 9.80-9.95 (br, 1H), 10.50-10.65 (br, 1H)

LCMS Rt=0.72 minutes. MS m/z 250 [M-H]⁻, 252 [MH]⁺

The ability of the compounds of formula (I) to block the Nav1.7 (or SCN9A) channel were measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 µg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 µg/ml G-418 in an incubator at 37° C. with a humidified atmosphere of 10% $CO_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM $CaCl_2$, 5.4 mM KCl, 1 mM $MgCl_2$, 10 mM glucose, and 10 mM HEPES, pH 7.4, with NaOH. Pipettes were filled with an intracellular solution of the following composition: 135 mM CsF, 5 mM CsCl, 2 mM $MgCl_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V1/2). Compounds were tested for their ability to inhibit hSCN9A sodium channels by activating the channel with a 20 msec voltage step to 0 mV following an 8 second conditioning prepulse to the empirically determined V1/2. Compound effect (% inhibition) was determined by difference in current amplitude before and after application of test compounds. For ease of comparison, "estimated IC-50" ($EIC_{50}$) values were calculated from single point electrophysiology data by the following equation, (tested concentration, uM)×(100-% inhibition % inhibition). Inhibition values <20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of $1 \times 10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V1/2 and current was activated by a 20 msec voltage step to 0 mV.

Electrophysiological assays may also be conducted using the Ionworks Quattro automated electrophysiology platform (Molecular Devices Corp). Intracellular and extracellular solutions were as described above with the following changes, 100 μg/ml amphotericin was added to the intracellular solution to perforate the membrane and allow electrical access to the cells. hSCN9A cells were grown and harvested as for PatchXpress and cells were resuspended in extracellular solution at a concentration of $3-4 \times 10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Compounds of the Examples were tested in the assay described above using the PatchXpress platform and found to have the Nav1.7 $EIC_{50}$ (uM) values specified in the table below.

| Ex. | $EIC_{50}$ |
|---|---|
| 1 | 0.0139 |
| 2 | 0.2853 |
| 3 | 0.3235 |
| 4 | 2.5966 |
| 5 | 0.2809 |
| 6 | 3.5766 |
| 7 | 35.6920 |
| 8 | >3 |
| 9 | >1 |
| 10 | 8.4603 |
| 11 | 0.0392 |
| 12 | 0.8430 |
| 13 | 0.0814 |
| 14 | 0.0668 |
| 15 | 0.0308 |
| 16 | 0.1500 |
| 17 | 0.1562 |
| 18 | 0.0806 |
| 19 | 0.7298 |
| 20 | >3 |
| 21 | 0.1610 |
| 22 | 0.0092 |
| 23 | NT |
| 24 | 0.1405 |
| 25 | 0.0186 |
| 26 | 4.9769 |
| 27 | 0.042 |
| 28 | 7.4364 |
| 29 | 0.8376 |
| 30 | <0.1 |
| 31 | <0.1 |
| 32 | 0.0110 |
| 33 | 0.3801 |
| 34 | 0.0822 |
| 35 | 0.0280 |

-continued

| Ex. | $EIC_{50}$ |
|---|---|
| 36 | 0.0527 |
| 37 | 0.0091 |
| 38 | 0.0215 |
| 39 | 0.0399 |
| 40 | NT |
| 41 | 0.0623 |
| 42 | 0.0518 |
| 43 | 0.0425 |
| 44 | 0.0258 |
| 45 | 0.0582 |
| 46 | 0.0180 |
| 47 | 4.3858 |
| 48 | >3 |
| 49 | 0.0097 |
| 50 | >3 |
| 51 | 6.2326 |
| 52 | >3 |
| 53 | >3 |
| 54 | NT |
| 55 | >1 |
| 56 | 6.7244 |
| 57 | 0.1526 |
| 58 | 6.8546 |
| 59 | 0.3561 |
| 60 | >3 |
| 61 | 1.8404 |
| 62 | 3.4130 |
| 63 | 6.6 |
| 64 | >1 |

NT = Not tested

The ability of compounds of formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the $EIC_{50}$ value at the Nav1.7 channel to determine the selectivity of a given compound for Nav1.7 vs Nav1.5.

The invention claimed is:
1. A compound of formula (I):

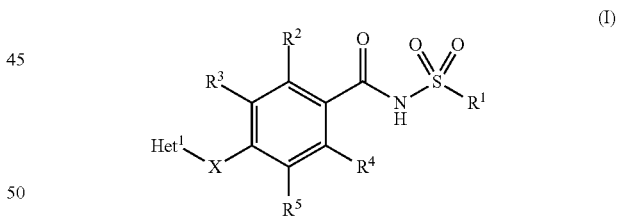

or a pharmaceutically acceptable salt thereof, wherein
X is —OCH$_2$— or —CH$_2$O—;
Het$^1$ is (i) a 9- or 10-membered heteroaryl comprising one to three nitrogen atoms;
or (ii) a 6-, 9- or 10-membered heteroaryl comprising one to three nitrogen atoms which heteroaryl is independently substituted by one to three substituents selected from Y$^1$ and Y$^2$;
Y$^1$ and Y$^2$ are independently selected from F; Cl; CN; (C$_1$-C$_8$)alkyl, optionally substituted by (C$_3$-C$_8$)cycloalkyl or one to three F; (C$_3$-C$_8$)cycloalkyl, optionally substituted by one to three F; NR$^7$R$^8$; (C$_1$-C$_8$)alkyloxy, optionally independently substituted by one to three R$^9$; (C$_3$-C$_8$)cycloalkyloxy; phenyl, optionally independently substituted by one to three R$^{10}$; Het$^2$ and Het$^3$;

wherein (C₃-C₈)cycloalkyloxy may be optionally fused to a phenyl ring or may be independently substituted by one to three R¹⁰;

R¹ is (C₁-C₆)alkyl or (C₃-C₈)cycloalkyl, each of which is optionally substituted by one to three F;

R², R³, R⁴ are independently H, F, Cl or —OCH₃;

R⁵ is H, CN, F, Cl or R⁶;

R⁶ is a group selected from (C₁-C₆)alkyl and (C₁-C₆)alkyloxy, wherein each group is optionally substituted, valency permitting, by one to five F;

R⁷ and R⁸ are independently H; (C₁-C₈)alkyl, optionally independently substituted by one to three R¹¹; (C₃-C₈)cycloalkyl; or 'C-linked' Het²; wherein (C₃-C₈)cycloalkyl may be optionally fused to a phenyl ring or may be independently substituted by one to three R¹⁰; or R⁷ and R⁸, taken together with the nitrogen atom to which they are attached, form a saturated, bridged, 7- to 9-membered ring;

R⁹ is F; (C₁-C₆)alkyloxy; (C₃-C₈)cycloalkyl, optionally substituted by one to three F;

Het²; or phenyl, optionally independently substituted by one to three R⁶;

R¹⁰ is F, Cl or R⁶;

R¹¹ is F; (C₁-C₆)alkyloxy; (C₃-C₈)cycloalkyl, optionally substituted by one to three F; 'C-linked' Het²; or phenyl, optionally independently substituted by one to three R⁶;

Het² is a 3- to 8-membered saturated monoheterocycloalkyl comprising one or two ring members selected from —NR¹²— and —O—, said monoheterocycloalkyl being optionally substituted on a ring carbon atom by one to three substituents independently selected from F, (C₁-C₆)alkyl, (C₁-C₄)alkyloxy(C₀-C₄)alkylene and (C₃-C₈)cycloalkyl;

Het³ is a 5- or 6-membered heteroaryl comprising one to three nitrogen atoms, said heteroaryl being optionally substituted by one to three substituents selected from F, Cl, CN and R⁶; and R¹² is H, (C₁-C₆)alkyl or (C₃-C₈)cycloalkyl, wherein (C₁-C₆)alkyl and (C₃-C₈)cycloalkyl are optionally substituted by one to three F; or, when Het² is 'N-linked', is absent.

2. A compound according to claim 1 wherein X is —OCH₂—.

3. A compound according to claim 1 wherein X is —CH₂O—.

4. A compound according to claim 1 wherein Het¹ is a 6-membered heteroaryl comprising one or two nitrogen atoms which heteroaryl is independently substituted by one to three substituents selected from Y¹ and Y².

5. A compound according to claim 1 wherein Het¹ is a 6-membered heteroaryl comprising one or two nitrogen atoms which heteroaryl is independently substituted by one or two substituents selected from Y¹ and Y².

6. A compound according to claim 1 wherein Het¹ is pyridyl independently substituted by one or two substituents selected from Y¹ and Y².

7. A compound according to claim 1 wherein Het¹ is pyridyl independently substituted by one or two Y and wherein said pyridyl is attached to the rest of the molecule at the 5-position as depicted below:

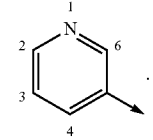

8. A compound according to claim 7 wherein said pyridyl is 2-substituted by Y¹, 3-substituted by Y² or, where di-substituted, 2-substituted by Y¹ and 3-substituted by Y².

9. A compound according to claim 1 wherein Y¹ is (C₁-C₈)alkyl, optionally substituted by (C₃-C₈)cycloalkyl or one to three F; (C₃-C₈)cycloalkyl, optionally substituted by one to three F; (C₁-C₆)alkyloxy, optionally substituted by one to three F; (C₃-C₈)cycloalkyloxy; or Het².

10. A compound according to claim 1 wherein Y² is F, Cl, CN, (C₁-C₈)alkyl, optionally substituted by (C₃-C₈)cycloalkyl or one to three F; (C₃-C₈)cycloalkyl, optionally substituted by one to three F; (C₁-C₆)alkyloxy, optionally substituted by one to three F; (C₃-C₈)cycloalkyloxy; or Het².

11. A compound according to claim 1 wherein R¹ is (C₁-C₄)alkyl or (C₃-C₆)cycloalkyl, such as methyl.

12. A compound according to claim 1 wherein R², R³ and R⁴ are independently H, F or Cl.

13. A compound according to claim 1 wherein R⁵ is H; CN; F; Cl; (C₁-C₄)alkyl, optionally substituted by one to three F; or (C₁-C₄)alkyloxy, optionally substituted by one to three F.

14. A compound according to claim 1 wherein R⁵ is H, CN, F, Cl, CH₃, C₂H₅, CF₃, —OCH₃, —OC₂H₅ or —OCF₃.

15. A pharmaceutical composition comprising a compound of formula (I) or a pharmaceutically acceptable salt thereof together, as defined in claim 1, with one or more pharmaceutically acceptable excipients.

16. A pharmaceutical composition according to claim 15 including one or more additional therapeutic agents.

17. A method for treating pain in a mammal comprising administering to a mammal in need thereof an effective amount of a compound according to claim 1, or a pharmaceutically acceptable salt thereof.

18. A method according to claim 17 is which said pain is selected from the group consisting of neuropathic, nociceptive and inflammatory pain.

* * * * *